(12) United States Patent
Shim

(10) Patent No.: US 7,876,917 B2
(45) Date of Patent: Jan. 25, 2011

(54) GENERIC ELECTROMAGNETICALLY-COUNTERED SYSTEMS AND METHODS

(76) Inventor: Youngtack Shim, 155 Aspenwood Drive, Port Moody (CA) V3H 5A5

( * ) Notice: Subject to any disclaimer, the term of this patent is extended or adjusted under 35 U.S.C. 154(b) by 1006 days.

(21) Appl. No.: 11/510,667

(22) Filed: Aug. 28, 2006

(65) Prior Publication Data

US 2008/0085021 A1 Apr. 10, 2008

(51) Int. Cl.
*H04R 25/00* (2006.01)
(52) U.S. Cl. .................................. 381/189; 381/191
(58) Field of Classification Search ................. 381/189, 381/96, 386, 394, 400, 401, 413, 414, 433, 381/71.8, 71.2, 191
See application file for complete search history.

(56) References Cited

U.S. PATENT DOCUMENTS 6,466,679 B1 * 10/2002 Husung ...................... 381/324

2004/0208337 A1 * 10/2004 Anciant ...................... 381/410

* cited by examiner

*Primary Examiner*—Tuan D Nguyen
(74) *Attorney, Agent, or Firm*—Rabin & Berdo, P.C.

(57) ABSTRACT

The present invention relates to an electromagnetically-countered system including at least one wave source irradiating harmful electromagnetic waves and at least one counter unit emitting counter electromagnetic waves for countering the harmful waves by such counter waves. More particularly, the present invention relates to generic counter units of electromagnetically-countered systems and to various mechanisms for countering the harmful waves by the counter units such as, e.g., by matching configurations of the counter units with those of the wave sources, matching shapes of such counter waves with shapes of the harmful waves, and the like. The present invention also relates to various methods of countering the harmful waves with the counter waves by such source matching or wave matching and various methods of providing the counter units as well as counter waves. The present invention further relates to various processes for providing such systems, such counter units thereof, and the like. The present invention relates to various electric and/or magnetic shields which may be used alone or in conjunction with such counter units to minimize irradiation of the harmful waves from the system.

20 Claims, 7 Drawing Sheets

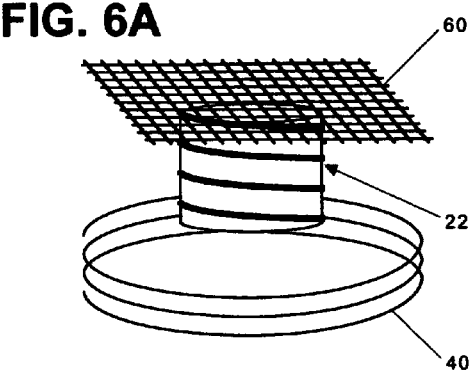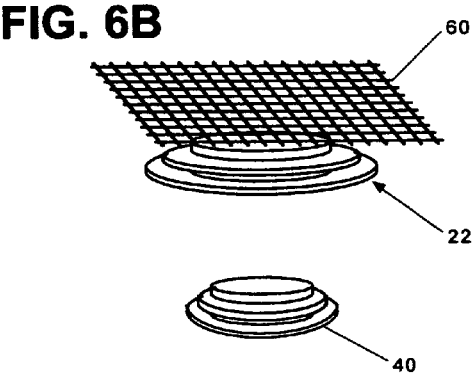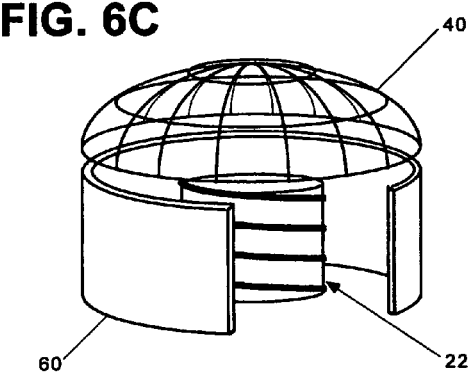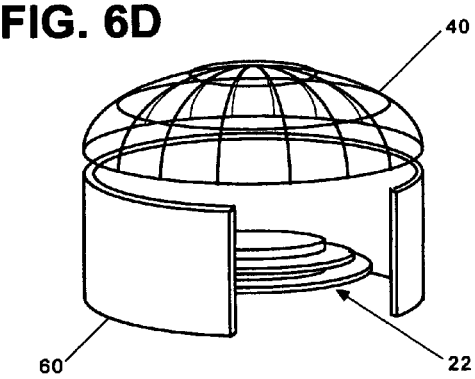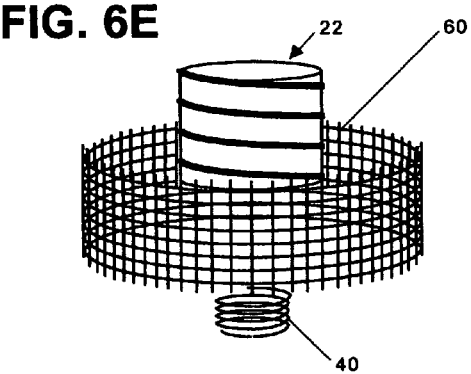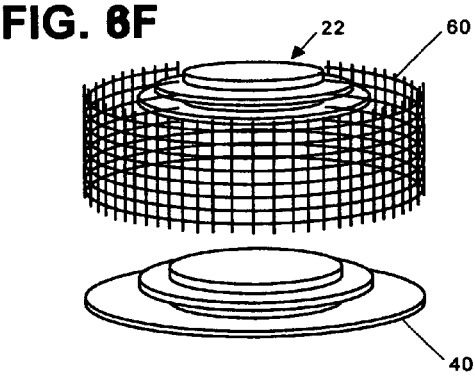

GENERIC ELECTROMAGNETICALLY-COUNTERED SYSTEMS AND METHODS

CROSS-REFERENCES TO RELATED APPLICATIONS

The present application is related to various patent applications which have been filed by the same Applicant. The first is the U.S. Utility patent application entitled "Shunted Magnet Systems and Methods," filed on Aug. 30, 2005, and bearing a Ser. No. 11/213,703. The second is the U.S. Utility patent application entitled "Magnet-Shunted Systems and Methods," filed on Aug. 30, 2005, and bearing a Ser. No. 11/213,686. The third is the U.S. Provisional Patent Application entitled "Electromagnetic Shield Systems and Methods," filed on Oct. 3, 2005, and bearing a Ser. No. 60/723,274, and the Disclosure Document entitled the same, deposited in the U.S. Patent and Trademark Office on Oct. 3, 2005 under the Disclosure Document Deposit Program of the Office, and bearing a Ser. No. 587,338. The fourth is the U.S. Utility Patent Application which is entitled "Electromagnetically-Shielded Air Heating Systems and Methods," which was filed on Dec. 22, 2005, and which bears a Ser. No. 11/313,921. The fifth is another U.S. Utility patent application entitled "Electromagnetically-Shielded Radiative Heating Systems and Methods," filed on Apr. 11, 2006, and bearing a Ser. No. 11/403,899. The sixth is another U.S. Utility Patent Application entitled, "Electromagnetically-Shielded Speaker Systems and Methods," filed on May 25, 2006, and bearing a U.S. Ser. No. 11/440,135. The seventh is another U.S. Provisional Patent Application entitled "Electromagnetically-Countered Speaker Systems and Methods," filed on Jun. 23, 2006, and bearing a U.S. Ser. No. 60/815,826. The eighth is another U.S. Provisional Patent Application entitled "Electromagnetically-Countered Actuator Systems and Methods," filed on Jul. 6, 2006, and bearing a U.S. Ser. No. 60/818,627. The last is another U.S. Utility Patent Application which is entitled "Electromagnetically-Shielded Heat Generating Systems and Methods," which is filed on Nov. 30, 2005, and which bears a U.S. Ser. No. 11/289,693. All of such Applications and Documents of this paragraph will be referred to as the "co-pending Applications" hereinafter, all of which are to be incorporated herein in their entirety by reference.

FIELD OF THE INVENTION

The present invention relates to an electromagnetically-countered system including at least one wave source irradiating harmful electromagnetic waves and at least one counter unit emitting counter electromagnetic waves for countering the harmful waves by such counter waves. More particularly, the present invention relates to generic counter units of electromagnetically-countered systems and to various mechanisms for countering the harmful waves by the counter units such as, e.g., by matching configurations of the counter units with those of the wave sources, matching shapes of such counter waves with shapes of the harmful waves, and the like. The present invention also relates to various methods of countering the harmful waves with the counter waves by such source matching or wave matching and various methods of providing the counter units as well as counter waves. The present invention further relates to various processes for providing such systems, such counter units thereof, and the like. The present invention relates to various electric and/or magnetic shields which may be used alone or in conjunction with such counter units to minimize irradiation of the harmful waves from the system.

BACKGROUND OF THE INVENTION

It is now well established in the scientific community that electromagnetic waves with varying frequencies irradiated by various devices may be hazardous to human health. In some cases, such electromagnetic waves in mega- and giga-hertz range may be the main culprit, whereas the 60-hertz electromagnetic waves may be the main health concern in other cases. It cannot be too emphasized that it is very difficult to shield against magnetic waves of the 60-hertz electromagnetic waves which have wavelengths amounting to thousands of kilometers and that such 60-hertz magnetic waves are omnipresent in any corner of the current civilization.

However, intensity of such electromagnetic waves typically decreases inversely proportional to a square of a distance from a source of such waves to a target. Accordingly, potentially adverse effects from such electromagnetic waves may be minimized by maintaining a safe distance from such a source. Some electrical devices, however, are intended to be used in a close proximity to an user, where typical examples of such devices are hair dryers, hair curlers, electric mattresses or blankets, heating pads, earphones, headphones, mobile phones, razors, toothbrushes, and the like. However, all prior art devices have failed to provide remedies to such potential hazards. For example, various prior art electric blankets and mattresses and their shortcomings have been provided in the above co-pending Application of U.S. Ser. No. 11/313,921 entitled "Electromagnetically-Shielded Air Heating Systems and Methods," and various radiative heaters and their shortcomings have been summarized in another co-pending Application of U.S. Ser. No. 11/403,899 entitled "Electromagnetically-Shielded Radiative Heating Systems and Methods." Various conventional speakers and their shortcomings have been itemized in two co-pending Applications of U.S. Ser. No. 11/440,135 entitled "Electromagnetically-Shielded Speaker Systems and Methods" and U.S. Ser. No. 60/815,826 entitled "Electromagnetically-Countered Speaker Systems and Methods," while various conventional electric actuators and their shortcomings have been described in the co-pending Application of U.S. Ser. No. 60/818,627 entitled "Electromagnetically-Countered Actuator Systems and Methods."

Therefore, there is an urgent need for a generic counter unit capable of being incorporated to various prior art devices and converting such devices into electromagnetically-countered systems for minimizing irradiation of the harmful electromagnetic waves therefrom. There also is a need to provide a feasible solution for countering the harmful waves irradiated by various waves sources of different shapes and/or sizes. There further is a need to provide another feasible solution for countering such harmful waves defining wavefronts of various characteristics.

SUMMARY OF THE INVENTION

The present invention relates to an electromagnetically-countered system including at least one wave source irradiating harmful electromagnetic waves and at least one counter unit emitting counter electromagnetic waves for countering the harmful waves by the counter waves, e.g., by canceling at least a portion of the harmful waves by the counter waves, by suppressing the harmful waves from propagating to a target space, and the like. More particularly, the present invention relates to generic counter units of the electromagnetically-countered systems and to various mechanisms for countering the harmful waves which are irradiated from various base units of the wave sources by the counter units. Accordingly, the counter unit may be shaped, sized, and/or arranged to match its configuration with configuration of the base unit of the wave source, thereby emitting such counter waves which automatically match characteristics of such harmful waves. In the alternative, the counter unit may be shaped, sized, and/or disposed in an arrangement which is defined along one or more wavefronts of the harmful waves, thereby emitting the counter waves which automatically match characteristics of the harmful waves. The present invention also relates to various counter units which are provided as analogs of the base unit of the wave source, where the analog may approximate the base unit which is more complex than such a counter unit, where the three- or two-dimensional base unit may also be approximated as the two- or one-dimensional analog, and the like. The present invention also relates to multiple simple counter units which are simpler than the base unit but disposed in an arrangement approximating such a shape and/or arrangement of the base unit. The present invention also relates to the counter unit which may be shaped and/or sized according to the configuration of the base unit and disposition thereof. In addition, the present invention relates to various countering modes where a single counter unit may counter a single base unit, at least two but not all of multiple base units or all of multiple base units, where multiple counter units may counter a single base unit, more base units or less multiple units, and the like. The present invention then relates to various electric and/or magnetic shields which may be used alone or in conjunction with the counter units to minimize irradiation of the harmful waves from the system.

The present invention also relates to various methods of countering the harmful waves by the counter waves by such source matching or wave matching. More particularly, the present invention relates to various methods forming the counter unit as an analog of the base unit and then emitting the counter waves matching such harmful waves, various methods of approximating the base unit by the simpler counter unit for the countering and various methods of approximating the base unit by multiple simpler counter units. The present invention also relates to various methods of disposing the counter unit along the wavefronts of the harmful waves and then emitting the counter waves for automatically matching such wavefronts of the harmful waves, various methods of disposing multiple counter units along the wavefronts of the harmful waves and then emitting the counter waves by the counter units for automatically matching such wavefronts, and the like. In addition, the present invention relates to various methods of manipulating the wavefronts of the counter waves by disposing the counter unit closer to and/or farther away from the target space with respect to the base unit, various methods of controlling radii of curvature of the wavefronts of the counter waves by incorporating one or multiple counter units emitting such counter waves of the same or opposite phase angles, various methods of adjusting the wavefronts of the counter waves by disposing one or multiple counter units defining the shapes similar to or different from the shapes of the base units, and the like. The present invention also relates to various methods of countering the harmful waves from one or multiple base units with the counter waves emitted by the single or multiple counter units. Accordingly, the present invention relates to various methods of emitting such counter waves from a single counter unit for the harmful waves irradiated by one or more base units, various methods of emitting such counter waves by two or more counter units for the harmful waves irradiated by a single or multiple base units, and the like. In addition, the present invention relates to various methods of minimizing irradiation of such harmful waves by incorporating such electric shields, by incorporating the magnetic shields, by incorporating one or both of such shields in conjunction with the above counter units, and the like.

The present invention further relates to various processes for providing various counter units and various systems incorporating one or multiple counter units therein. More particularly, the present invention relates to various processes for forming the counter units to emit the counter waves having the wavefronts similar to (or different from) such shapes of the counter units, various processes for forming the counter units as the above analogs of the base units, various processes for providing the counter units emitting such counter waves which define the similar or opposite phase angles, various processes for providing such counter units with the wavefronts shaped similar to the harmful waves, various processes for disposing the counter units in a preset arrangement and emitting therefrom the counter waves which have the wavefronts similar to such an arrangement, and the like. The present invention also relates to various processes for assigning the single counter unit to counter the harmful waves irradiated by the single base unit for a local countering or to counter such harmful waves from multiple base units for a global countering, various processes for assigning multiple counter units to counter the harmful waves irradiated by the single base unit for the global countering or to counter the harmful waves from multiple base units for the local or global countering depending on numbers of the counter and base units. The present invention further relates to various processes for incorporating the electric and/or magnetic shields for minimizing the irradiation of such harmful waves, and various processes for minimizing the irradiation of such harmful waves by employing such shields as well as the above counter units.

Accordingly, a primary objective of the present invention is to provide an electromagnetically-countered (to be abbreviated as an "EMC" hereinafter) system (to be abbreviated as an "EMC system" or simply a "system" hereinafter) which is capable of minimizing the irradiation of the harmful waves from at least one base unit of at least one wave source by countering the harmful waves with such counter waves. Therefore, a related objective of this invention is to provide an EMC system capable of countering the harmful waves by canceling at least a portion of the harmful waves by the counter waves and/or by suppressing the harmful waves from propagating toward a preset direction by the counter waves. Another related objective of this invention is to counter the harmful waves by such counter waves not all around the base unit of the EMC system but only in the target space (or area) which is defined on only one side of the system. In general, such a target space is defined between the base unit and an user of the system or a specific body part of the user. Another related objective of this invention is to arrange the counter waves to define the phase angles at least partially opposite to those of the harmful waves so that the counter waves cancel and/or suppress the harmful waves when propagated to the target space. Another related objective of this invention is to arrange such counter waves to define the phase angles at least partially similar to those of the harmful waves such that the counter waves cancel and/or suppress the harmful waves when propagated to such a target space from an opposite side of the base unit. Another related objective of this invention is to emit the counter waves from the same or opposite side of the base unit with respect to the target space while manipulating their phase angles such that the counter waves from different counter units counter the harmful waves in the target space.

Another objective of the present invention is to provide such an EMC system with at least one counter unit capable of emitting such counter waves. Therefore, a related objective of this invention is to match at least one feature or configuration (e.g., each meaning a shape, a size, an arrangement, and the like) of the counter unit with the feature or configuration of the base unit such that the counter waves emitted from the counter unit match the harmful waves irradiated from the base unit. Another related objective of this invention is to match the shape of a single counter unit defining the shape of a single base unit such that the counter waves emitted by the counter unit match the harmful waves by the base unit. Another related objective of this invention is to match the shape of a single counter unit with an arrangement of multiple base units such that the counter waves emitted from the counter unit match a sum of the harmful waves irradiated by multiple base units. Another related objective of this invention is to dispose multiple counter units in an arrangement which match the shape of a single base unit so that a sum of such counter waves emitted from multiple counter units match the harmful waves by the base unit. Another related objective of this invention is to arrange multiple counter units in an arrangement which matches another arrangement of multiple base units such that a sum of the counter waves emitted by multiple counter units match another sum of the harmful waves by multiple base units. Another related objective of this invention is to provide such counter units while using the least amount of electrically conductive, semiconductive, and/or insulative materials, while minimizing a total volume or a size of the counter units, while minimizing a total mass of such counter units, and the like. Another related objective of this invention is to emit the counter waves by the counter units while using the least electrical energy, while drawing the least amount of electric current or voltage from the base unit or other parts of the EMC system, and the like.

Another objective of the present invention is to provide an EMC system which includes therein at least one counter unit matching the shape of at least one base unit. Accordingly, a related objective of this invention is to form the counter unit as an one-, two- or three-dimensional analog of the three-dimensional base unit and to counter the single or multiple base units by the single or multiple analogs. Another related objective of this invention is to provide the counter unit as an one- or two-dimensional analog of the three-dimensional base unit and to counter the single or multiple base units by the single or multiple analogs. Another related objective of this invention is to provide the counter unit as an one- or two-dimensional analog of the two-dimensional base unit and then to counter the single or multiple base units with the single or multiple analogs. Another related objective of this invention is to form the counter unit as an one-dimensional analog of the two-dimensional base unit and to counter the single or multiple base units by the single or multiple analogs. Another related objective of this invention is to provide the counter unit as an one-dimensional analog of an one-dimensional base unit and to counter the single or multiple base units using the single or multiple analogs. Another related objective of this invention is to provide such counter units as one-, two-, and/or three-dimensional analogs of an one-, two-, and/or three-dimensional base units and then to counter the base units of the mixed dimension by the counter units of the mixed dimension. In these objectives, such counter units emit the counter waves capable of matching the harmful waves irradiated by the base units. Another related objective of this invention is to form the counter unit conforming to the shape of the base unit for matching such harmful waves with the counter waves emitted thereby. Another related objective of this invention is to form the counter unit which does not conform to the shape of the base unit but which is disposed in an arrangement for matching the harmful waves by such counter waves emitted thereby. Another related objective of this invention is to form the counter unit in a shape of one or multiple wires, strips, sheets, tubes, coils, spirals, meshes, mixtures thereof, combinations thereof, and/or arrays thereof in order to match the shape of the base unit and to emit the counter waves matching the harmful waves. Another related objective of this invention is to dispose any of the above counter units within a preset distance from the base unit in order to match at least some wavefronts of the counter waves emitted thereby to at least some wavefronts of the harmful waves. Another related objective of this invention is to dispose any of the above counter units in a preset arrangement with respect to the base unit so as to match at least some wavefronts of the counter waves with at least some of the harmful waves.

Another objective of the present invention is to provide an EMC system which includes therein at least one counter unit having a size which operatively matches a size of the base unit for matching the harmful waves irradiated by the base unit with the counter waves emitted thereby. Accordingly, a related objective of this invention is to provide the counter unit larger, wider, and/or longer than the base unit, where such a counter unit is preferably disposed between the base unit and target space (to be referred to as a "front arrangement" hereinafter) for such matching. Another related objective of this invention is to form the counter unit defining a size, a width, and/or a length similar (or identical) to those of the base unit, where the counter unit is preferably disposed laterally or side by side to the base unit with respect to the target space (to be referred to as a "lateral arrangement" hereinafter) for the matching. Another related objective of this invention is to form the counter unit smaller, narrower, and/or shorter than the base unit, where the counter unit is preferably disposed on an opposite side of the target space relative to the base unit (to be referred to as a "rear arrangement" hereinafter) for the matching. Another related objective of this invention is to enclose at least a portion of the counter unit by the base unit or, in the alternative, to enclose at least a portion of the base unit by the counter unit (to be referred to as a "concentric arrangement" hereinafter) for such matching. Another related objective of this invention is to dispose multiple counter units in such a front, lateral, rear or concentric arrangement with respect to the single base unit for such matching. Another related objective of this invention is to form the single or multiple counter units disposed in the front, lateral, rear or concentric arrangement with respect to multiple base units for such matching. Another related objective of this invention is to define multiple counter units all of which are disposed in only one of such front, lateral, rear, and concentric arrangements with respect to all of multiple base units or at least two of which are disposed in different (or mixed) arrangements with respect to at least two of multiple base units for such matching.

Another objective of the present invention is to provide an EMC system which incorporates at least one counter unit in a disposition (e.g., an orientation, an alignment, and a distance) matching that of the base unit. Thus, a related objective of this invention is to orient the counter unit in a direction of propagation of the harmful waves, in another direction in which the current flows in the base unit, in another direction in which the voltage is applied across the base unit, in a direction of the longitudinal axis of the base unit, and/or in a direction of the short axis thereof for the matching. Another related objective of this invention is to form multiple counter units all of which are oriented in one of the same directions or axes, at least two of which are oriented along different directions and/or axes, and all of which are oriented in different directions or axes for such matching. Another related objective of this invention is to axially align the counter unit with respect to the base unit (to be referred to as an "axial alignment" hereinafter) so that the counter waves emitted by the counter unit are to axially align with such harmful waves which are irradiated by the base unit for the matching. Another related objective of this invention is to axially misalign the counter unit with the base unit (to be referred to as an "off-axis alignment" hereinafter) but to dispose the counter unit in a preset arrangement for such matching. Another related objective of this invention is to provide multiple counter units disposed in such an axial or off-axis alignment with respect to the single base unit for such matching. Another related objective of this invention is to provide the single or multiple counter units which are disposed in the axial or off-axis alignment with respect to multiple base units for such matching. Another related objective of this invention is to define multiple counter units all of which are disposed in the axial or off-axis alignment with respect to all of multiple base units or at least two of which are disposed in different (or mixed) alignments relative to at least two of multiple base units for the matching. Another related objective of this invention is to dispose the counter unit at a preset distance from the base unit such that at least some wavefronts of the counter waves from the counter unit match at least some wavefronts of the harmful waves from the base unit for such matching. Another related objective of this invention is to dispose the single counter unit at preset distances from each (or at least two) of multiple base units for such matching. Another related objective of this invention is to dispose multiple counter units at preset distances from the single base unit or, alternatively, at preset distances from each (or at least two) of multiple base units for the matching.

Another objective of the present invention is to provide an EMC system which includes therein at least one counter unit for emitting the counter waves which have amplitudes matching those of the harmful waves. Therefore, a related objective of this invention is to provide the counter unit emitting the counter waves with amplitudes greater than those of the harmful waves, where this counter unit is preferably disposed farther away from the target space compared with the base unit or in the rear arrangement for such matching. Another related objective of this invention is to form the counter unit emitting the counter waves with amplitudes similar (or identical) to those of the harmful waves, where such a counter unit is preferably disposed side by side with the base unit relative to the target space or in the lateral arrangement for the matching. Another related objective of this invention is to form the counter unit emitting the counter waves with amplitudes less than those of the harmful waves, where this counter unit is preferably disposed closer to such a target space than the base unit or in the front arrangement for the matching. Another related objective of this invention is to provide multiple counter units emitting the counter waves a sum of which may define the amplitudes greater than, similar to or less than those of the single base unit, those of all of multiple base units, those of at least two but not all of multiple counter units, and the like.

Another objective of the present invention is to provide such an EMC system including at least one counter unit capable of emitting the counter waves which match at least a portion of the harmful waves and, therefore, counter the harmful waves. Therefore, a related objective of this invention is to provide the counter unit for emitting such counter waves defining multiple wavefronts which match at least one of of the wavefronts of the harmful waves in the target space. Another related objective of this invention is to dispose the counter unit along at least a portion of at least one of the wavefronts of the harmful waves and to emit the counter waves matching such a portion of the wavefront of the harmful waves. Another related objective of this invention is to dispose multiple counter units along at least a portion of at least one of the wavefronts of the harmful waves and to emit the counter waves a sum of which then matches such a portion of the wavefront of the harmful waves. Another related objective of this invention is to dispose the counter unit across at least two of such wavefronts of the harmful waves but to emit the counter waves capable of matching at least a portion of at least one of the wavefronts of the harmful waves. Another related objective of this invention is to provide multiple counter units at least two of which are disposed across at least two of the wavefronts of the harmful waves but to emit the counter waves capable of matching the portion of the wavefront of the harmful waves. Another related objective of this invention is to shape and size such a counter unit in order to emit the counter waves with radii of curvature which match those of at least a portion of the harmful waves. Another related objective of this invention is to dispose the counter unit in a preset position or at a preset distance from the base unit in which the counter waves emitted thereby define the radii of curvature which match those of at least a portion of the harmful waves. Another related objective of this invention is to shape and size multiple counter units emitting such counter waves a sum of which define the radii of curvature matching the harmful waves irradiated by the single base unit or multiple base units. Another related objective of this invention is to provide the counter unit in a shape of one or multiple wires, strips, sheets, tubes, coils, spirals, meshes, mixtures thereof, combinations thereof, and/or arrays thereof and to emit the counter waves capable of matching at least a portion of at least one wavefront of the harmful waves from the base unit. Another related objective of this invention is to fabricate the counter unit into a solid shape without forming any openings or holes thereacross for the matching. Another related objective of this invention is to fabricate the counter units as the arrays defining multiple holes or openings thereacross for such matching.

Another objective of the present invention is to provide an EMC system which includes therein at least one counter unit for emitting the counter waves and for locally countering the harmful waves irradiated from the base unit. Accordingly, a related objective of this invention is to provide the single counter unit for locally countering the harmful waves from the single base unit by the counter waves emitted thereby. Another related objective of this invention is to provide multiple counter units each of which locally counters the harmful waves from only one of the same (or less number) of base units with the counter waves emitted from each of multiple counter units. Another related objective of this invention is to provide the single counter unit (or multiple counter units) which defines the feature (or configuration) similar (or identical) to that of the single base unit (or multiple base units) for such local countering. Another related objective of this invention is to provide the single counter unit (or multiple counter units) emitting the counter waves which define the wavefronts matching at least one of the wavefronts of the harmful waves irradiated from the single base unit (or multiple base units) for such local countering. Another related objective of this invention is to provide multiple counter units at least one of which defines the feature (or configuration) similar (or identical) to that of the base unit and at least another of which defines the wavefronts matching at least one of the wavefronts of the harmful waves from the base unit for such local countering.

Another objective of the present invention is to provide an EMC system which includes therein at least one counter unit for emitting the counter waves and for globally countering the harmful waves irradiated from the base unit. Therefore, a related objective of this invention is to form one or multiple counter units each emitting the counter waves for globally matching the harmful waves irradiated from one or a less number of base units. Another related objective of this invention is to provide the single counter unit for globally countering a sum of the harmful waves irradiated by multiple base units by the counter waves emitted thereby. Another related objective of this invention is to form multiple counter units each of which globally counters the harmful waves irradiated by at least two base units by the counter waves emitted by each of multiple counter units. Another related objective of this invention is to define the single counter unit (or multiple counter units) which defines the feature (or configuration) which is similar (or identical) to those of at least two (or a greater number of) base units for the global countering. Another related objective of this invention is to provide the single counter unit (or multiple counter units) emitting the counter waves which define the wavefronts matching at least one of the wavefronts of the harmful waves irradiated from at least two (or a greater number of) base units for the global countering. Another related objective of this invention is to provide multiple counter units at least one of which defines the feature (or configuration) similar (or identical) to those of at least two base units and at least another of which defines the wavefronts matching at least one wavefront of the harmful waves irradiated by at least two of other base units for such local countering.

Another objective of the present invention is to provide an EMC system which includes therein at least one counter unit which is disposed in a preset position or location defined relative to the base unit and/or target space. Therefore, a related objective of this invention is to dispose the counter unit on (or over) an exterior surface of the base unit, to dispose the counter unit on (or below) an interior surface of the base unit, to embed at least a portion of the counter unit inside the base unit, and so on. Another related objective of this invention is to provide the system with a case member and to dispose the counter unit on (or over) an exterior surface of the case member, to dispose such a counter unit on (or below) an interior surface of the case member, to embed at least a portion of the counter unit inside the case member, to dispose the counter unit between the case member and base unit, and the like. Another related objective of this invention is to dispose the counter unit in a preset relation to the case member such as, e.g., exposing at least a (or entire) portion of the counter unit through the case member, enclosing the entire portion of the counter unit inside the case member, and the like.

Another objective of the present invention is to provide an EMC system which includes therein at least one counter unit emitting the counter waves propagating along preset directions. Therefore, a related objective of this invention is to arrange the counter unit to emit the counter waves always in a fixed direction with respect to the base unit such that the counter waves propagate along a direction defined based on a preset relation to a direction of propagation of the harmful waves, e.g., parallel to the harmful waves, perpendicular to the harmful waves, at a preset angle with respect to the harmful waves, and so on. Another related objective of this invention is to arrange the counter unit to emit the counter waves in variable directions with respect to a direction of propagation of the harmful waves, where such a counter unit is arranged to change its arrangement and/or orientation and/or to receive the current and/or voltage along variable directions for changing the direction of such counter waves. Another related objective of this invention is to arrange the counter unit to emit the counter waves in a direction which is adaptively determined by variable directions of propagation of the harmful waves, where such a counter unit may change the direction of the counter waves as described hereinabove. Therefore, such a counter unit may change an extent of countering based on its arrangement and/or orientation. Another related objective of this invention is to synchronize a propagation direction of the counter waves with that of such harmful waves based on the preset relation disclosed hereinabove. Another related objective of this invention is to arrange the counter unit to manipulate the amplitudes of the counter waves in various mechanisms similar to those for manipulating the directions thereof.

Another objective of the present invention is to provide an EMC system with at least one of the above counter units and to supply the electric current or voltage thereto for countering such harmful waves by such counter waves emitted thereby. Accordingly, a related objective of this invention is to provide the counter unit with the electric current or voltage which is supplied to the above base unit or at least one of multiple base units. Another related objective of this invention is to provide the counter unit with at least a portion but not an entire portion of the electric current or voltage supplied to such a base unit or at least one of multiple base units. Another related objective of this invention is to provide the counter unit with such a portion of the current or voltage of which the amplitudes and/or direction are modified before being supplied thereto. In all of these examples, the current or voltage supplied to the counter unit is automatically synchronized with such current or voltage supplied to the base unit or at least one of multiple base units. Another related objective of this invention is to supply the counter unit with electric current or voltage which is not the current or voltage supplied to the base unit or at least one of multiple base units but which is at least partially synchronized with the current or voltage supplied to such base units. Another related objective of this invention is to manipulate the amplitudes or directions of the current or voltage depending upon configuration and/or disposition of the counter unit. Another related objective of this invention is to electrically couple the counter unit with the base unit in a parallel, series or hybrid mode. Another related objective of this invention is to supply such electric current or voltage based upon various sequences such as, e.g., first to the base unit and then to the counter unit, first to the counter unit then to the counter unit, first to one of multiple counter units and then to the rest of the counter units or base unit, first to one of multiple base units and then to the rest of the base units or counter unit, simultaneously to the counter and base units, and the like.

It is to be understood in all of such objectives that the counter units are preferably arranged to not adversely affect other intended operations of the systems. For example, the counter units of the EMC speaker systems may effectively counter the harmful waves irradiated by their sound generating base units but may not adversely affect the quality of acoustic sounds generated thereby. In another example, the counter units of the EMC actuator systems may effectively counter such harmful waves irradiated by their electromotive base units but may not adversely affect the amplitude of electromotive force generated thereby. In another example, the counter units of the EMC heating systems may also effectively counter the harmful waves irradiated by their heating base units but may neither adversely affect the amount of thermal energy generated thereby. In another example, the counter units of the EMC transformer systems may effectively counter the harmful waves irradiated by their transforming coils but may not adversely affect voltage levels obtained thereby. It is also appreciated in all of such objectives that the counter units are preferably arranged to emit the counter waves which define the phase angles at least partially opposite to those of the harmful waves for such countering but that the counter units may also emit the counter waves which define the phase angles at least partially similar to those of the harmful waves when disposed on an opposite side of the base unit with respect to the target space or when the system includes multiple counter units and it is desirable to modify the radii of curvature of the wavefronts of the counter waves. It is further appreciated that the electric and/or magnetic shields disclosed in the co-pending Applications may be incorporated into any of the above EMC systems either alone or in combination with the above counter units for maximally countering the harmful waves.

The basic principle of the counter units of the generic electromagnetically-countered systems of this invention is to emit the counter waves which form the wavefronts similar (or identical) to those of the harmful waves but define the phase angles at least partially opposite to those of such harmful waves. Therefore, by propagating such counter waves to the target space, the counter waves can effectively counter the harmful waves in the target space by, e.g., canceling at least a portion of such harmful waves therein and/or suppressing the harmful waves from propagating theretoward. To this end, the counter units are arranged to emit the counter waves which define the wavefronts matching those of the harmful waves by various mechanisms. In one example, such counter units are shaped similar (or identical) to the base units of the waves sources, or arranged similar (or identical) to such base units and, therefore, emit the counter waves which can counter the harmful waves in the target space. In another example, such counter units are disposed along one or more of the wavefronts of the harmful waves and emit the counter waves which are similar (or identical) to the harmful waves and, accordingly, counter the harmful waves in the target space. In these two examples, the counter units are to emit the counter waves with the wavefronts which are similar (or identical) to the shapes of such counter units themselves, and such counter waves are to define the phase angles which are at least partially opposite to the phase angles of the harmful waves. In another example, the counter units are shaped differently from the base units, but are rather disposed in an arrangement in which the counter waves emitted therefrom may match such harmful waves in the target space. In another example, the counter units are disposed across different wavefronts of the harmful waves but are to emit the counter waves which are similar (or identical) to the harmful waves and, therefore, counter the harmful waves in the target space. In the last two examples, the counter units may be arranged to emit the counter waves with the wavefronts may or may not be similar (or identical) to the shapes of the counter units themselves, while the counter waves are to define the phase angles which are at least partially opposite to those of the harmful waves.

The basic principle of the counter units of the generic electromagnetically-countered system of this invention may be implemented into various prior art devices for minimizing irradiation of the harmful waves therefrom. For example, the counter units may be implemented to any base units of electrically conductive wires, coils, and/or sheets or, in the alternative, into any electrically semiconductive and/or insulative wires, coils, and/or sheets for minimizing the irradiation of the harmful waves by countering such harmful waves by the counter waves, e.g., by canceling at least a portion of the harmful waves in the target space and/or suppressing the harmful waves from propagating toward the target space, where the counter units may be made of and/or include at least one electrically conductive, insulative or semiconductive material. The counter units may be implemented into any of such base units which define the shapes which may be formed by incorporating one or multiple wires, coils, and/or sheets, by modifying the shapes of one or multiple wires, coils, and/or sheets, where a few examples of the modified shapes may include a solenoid and toroid each formed by modifying the shape of such a coil. Therefore and in one example, such counter units may be implemented into various speakers such as cone-drive speakers, electrostatic speakers, and piezoelectric speakers for minimizing the irradiation of the harmful waves. Accordingly, any prior art devices including the electromagnetically-countered speakers such as earphones, headphones, wired phones, mobile phones, and audiovisual devices may be converted into the electromagnetically countered systems. Similarly, the counter units may be implemented into various microphones which are inverse examples of such speakers, and any prior art devices including such electromagnetically-countered microphones such as wired phones, mobile phones, audio and/or audiovisual sound systems, and an assembly of the earphone and microphone may be converted into the electromagnetically countered systems. In another example, such counter units may be implemented into various motors such as DC motors, universal motors, AC synchronous motors, AC induction motors, linear motors, and the like, for minimizing the irradiation of such harmful waves. Therefore, any prior art actuator devices including the electromagnetically-countered motors such as kitchen appliances (e.g., a food processor, a mixer, a juicer, a grinder, a blender, a squeezer, a can opener, a dishwasher, a refrigerator, a freezer, a cooler, and so on), cooking appliances (e.g., an electric grill, an electric oven, an electric stove, an electric range, an electric toaster, an electric fan for such, and the like), household appliances (e.g., a cloth washer, a cloth dryer, an air conditioner, a garage opener, a dry or wet vacuum cleaner, and so on), tools (e.g., an electric drill, an electric saw, an electric screwdriver, an electric nail or staple gun, an electric sander, and the like), and personal hygiene devices (e.g., an electric razor, an electric toothbrush, an electric hair dryer, and the like) may be converted into the electromagnetically countered systems. Similarly, the counter units may also be implemented to various generators, and any prior art generating devices with the electromagnetically-countered generators such as AC generators, DC generators, and (automobile) alternators may also be converted into the electromagnetically countered systems. In another example, such counter units may be implemented into various transformers which include therein at least two coils, and any prior art devices including the electromagnetically-countered transformers such as step-up transformers, step-down transformers, and AC/DC adaptors of various electric devices may be converted into the electromagnetically countered systems. In another example, such counter units may be implemented to various heating unit including at least one resistive heating wire, heating strip, heating sheet, and/or heating coil for minimizing the irradiation of the harmful waves during heating. Accordingly, any prior art heating devices such as personal heating appliances (e.g., an electric mattress or mat, an electric blanket, an electric heating pad, and so on), cooking appliances (e.g., an electric grill, an electric oven, an electric stove, an electric range, an electric toaster, an electric toaster oven, and the like), and/or beauty-related appliances (e.g., a hair dryer, a hair setter, a hair curler, a hair steamer, and the like), may be converted into the electromagnetically countered systems. In another example, such counter units may be implemented into various light emitting units for minimizing the irradiation of such harmful waves during lighting. Accordingly, any prior art display devices such as a cathode ray tube, a light emitting device, an organic light emitting device, an inorganic light emitting device, and a plasma display panel may be converted into the electromagnetically countered systems.

It is appreciated that various counter units of the generic EMC systems of this invention may be incorporated into any electrical and/or electronic devices each of which may include at least one base unit and, accordingly, may irradiate the harmful waves including electric waves (to be abbreviated as "EWs" hereinafter) and magnetic waves (to be abbreviated as "MWs" hereinafter) having frequencies of about 50 to 60 Hz and/or other EWs and MWs of higher frequencies. It is also appreciated that the generic EMC systems of this invention may also be incorporated into any portable or stationary electric and/or electronic devices which include at least one base unit detailed examples of which have been provided heretofore and will be provided hereinafter. It is further appreciated that such counter units may be provided in a micron-scale and incorporated to semiconductor chips and circuits such as LSI and VLSI devices and that such counter units may be provided in a nano-scale and incorporated into various nano devices including at least one base unit which in this case may be a single molecule or a compound or may be a cluster of multiple molecules or compounds.

Various system, method, and/or process aspects of the generic electromagnetically-countered systems and various embodiments thereof are now enumerated. It is to be understood, however, that following system, method, and/or process aspects of the present invention may be embodied in many other different forms and, accordingly, should not be limited to such aspects and/or their embodiments which are to be set forth herein. Rather, various exemplary aspects and their embodiments described hereinafter are provided such that this disclosure will be thorough and complete, and fully convey the scope of the present invention to one of ordinary skill in the relevant art.

In one aspect of the present invention, an exemplary system may be provided for countering harmful electromagnetic waves irradiated from a base unit of at least one wave source by canceling the harmful waves in a target space and/or suppressing the harmful waves from propagating toward the target space, where such a base unit includes only portions of the wave source responsible for irradiating the harmful waves and for affecting paths of the harmful waves therethrough and where the target space is defined between the system and an user.

In one exemplary embodiment of this aspect of the invention, a system may include at least one counter unit which is arranged to define a shape identical (or similar) to the base unit, and then to emit counter electromagnetic waves, where such counter waves are arranged to define phase angles at least partially opposite to those of the harmful waves, to define wave characteristics at least partially similar to those of the harmful waves due to the shape and, therefore, to counter such harmful waves due to the opposite phase angles in the target space. It is appreciated that those counter waves are to be referred to as the "counter waves of the first type" or "first counter waves" hereinafter.

In another exemplary embodiment of this aspect of the invention, a system may include a single counter unit which is arranged to have a shape of an one-dimensional (or 1-D), a two-dimensional (or 2-D) or three-dimensional (or 3-D) analog of the base unit and to emit the first counter electromagnetic waves. Alternatively, such a single counter unit may be arranged to define a shape of an 1-D (or 2-D, 3-D) analog of at least two of multiple base units and to emit the first counter electromagnetic waves.

In another exemplary embodiment of this aspect of the invention, a system may include multiple counter units at least two of which are arranged to define shapes of 1-D (or 2-D, 3-D) analogs of the base unit, and to emit counter electromagnetic waves which are arranged to define phase angles at least partially opposite to those of the harmful waves, to define wave characteristics at least partially similar to those of the harmful waves due to the shapes and, therefore, to counter the harmful waves due to such opposite phase angles in the target space. In the alternative, at least two of such multiple units may instead be arranged to define shapes of 1-D (or 2-D, 3-D) analogs of at least two of multiple base units and to emit the counter electromagnetic waves described above in this paragraph.

In another aspect of the present invention, an exemplary system may be provided to counter harmful electromagnetic waves irradiated from a base unit of at least one wave source by matching a shape and/or an arrangement of the base unit with another shape and/or arrangement of at least one part of the system and by canceling the waves in a target space and/or suppressing the waves from propagating to the target space, where the base unit is arranged to include only portions of the wave source responsible for irradiating such harmful waves and affecting paths of the waves therethrough and where the target space is defined between the system and an user.

In one exemplary embodiment of this aspect of the invention, a system may include at least one counter unit which is arranged to have a shape similar to (or identical) to (or to conform to) that of the base unit and to emit the first counter electromagnetic waves.

In another exemplary embodiment of this aspect of the invention, a system may include at least one counter unit which is arranged to have a shape different from (or not conforming to) that of such a base unit, to be in a preset arrangement relative to the base unit, and to emit counter electromagnetic waves which are arranged to define phase angles at least partially opposite to those of such harmful waves, to have wave characteristics at least partially similar to those of the harmful waves due to the arrangement and, accordingly, to counter such harmful waves in the target space due to the opposite phase angles. It is appreciated that such counter waves are to be referred to as the "counter waves of the second type" or "second counter waves" hereinafter.

In another exemplary embodiment of this aspect of the invention, a system may include at least one counter unit which is provided in various arrangements but emits the above first counter waves. In one example, the counter unit is arranged to define a shape of an 1-D analog of an 1-D, 2-D or 3-D base unit and to emit the first counter waves. In another example, the counter unit arranged to define a shape of at least one 1-D analog of multiple 1-D, 2-D or 3-D base units and to emit such first counter waves. In another example, the counter unit is arranged to define a shape of a 2-D analog of an 1-D, 2-D or 3-D base unit and to emit the above first counter waves. In another example, the counter unit is arranged to have a shape of at least one 2-D analog of multiple 1-D, 2-D or 3-D base units and then to emit the first counter waves. In another example, the counter unit is arranged to define a shape of a 3-D analog of an 1-D, 2-D or 3-D base unit and to emit the first counter waves. In another example, such a counter unit is arranged to have a shape of at least one 3-D analog of multiple 1-D, 2-D or 3-D base units and to emit the first counter waves.

In another exemplary embodiment of this aspect of the invention, a system may be provided in various arrangements. In one example, such a system may include at least one counter unit which is arranged to define a shape matching that of the base unit and to also emit the first counter waves. In another example, a system may include at least one counter unit which is arranged to define a shape matching shapes of multiple base units and then to emit the first counter waves. In another example, a system may also have multiple counter units which are arranged to form an overall shape matching a shape of the base unit and to emit the first counter waves. In another example, a system may have multiple counter units which are arranged to form an overall shape matching another overall shape of multiple base units and to emit the first counter waves.

In another exemplary embodiment of this aspect of the invention, a system may be provided in various arrangements. In one example, such a system may include at least one counter unit which is arranged to be disposed between the base unit and target space, to have a width longer than that of the base unit, and then to emit counter electromagnetic waves which are arranged to define phase angles at least partially opposite to those of the harmful waves, to have wave characteristics at least partially similar to those of the harmful waves due to the width and, therefore, to counter the harmful waves in the target space due to the opposite phase angles. In another example, a system may have at least one counter unit which is arranged to be incorporated between the target space and multiple base units, to have a width longer than a contour formed by all of the base units, and then to emit the counter waves described above in this paragraph. In another example, a system may include multiple counter units which are also arranged to be disposed between the base unit and target space, to be disposed in an arrangement defined along a width longer than that of the base unit, and to emit such counter waves described above in this paragraph. In another example, a system may include multiple counter units which are arranged to be disposed between the target space and multiple base units, to be disposed in an arrangement defined along a width which is longer than a contour defined by all of the base units, and to emit the counter waves described above in this paragraph. In another example, a system may include at least one counter unit which is arranged to be disposed on an opposite side of the target space with respect to the base unit, to define a width shorter than that of the base unit, and to emit the counter waves described above in this paragraph. In another example, a system may include at least one counter unit which is arranged to be disposed on an opposite side of the target space with respect to multiple base units, to have a width shorter than a contour formed by the base units, and to emit the counter waves described above in this paragraph. In another example, another system may have multiple counter units which are arranged to be disposed on an opposite side of the target space with respect to the base unit, to be disposed into an arrangement defined along a width shorter than that of the base unit, and to emit the counter waves described above in this paragraph. In another example, such a system may instead have multiple counter units which are arranged to be disposed on an opposite side of the target space with respect to multiple base units, to be disposed in an arrangement along a width which is shorter than a contour formed by all of the base units, and to emit the counter waves described above in this paragraph.

In another exemplary embodiment of this aspect of the invention, a system may include at least one counter unit which is arranged to define a shape of a wire, a strip, a sheet, a tube, a coil, a spiral, a mesh, a mixture thereof, a combination thereof, and/or an array thereof while conforming its shape to a shape of the base unit, and to emit the first counter waves. In the alternative, such a counter unit may be arranged to define a shape of at least one of a wire, a strip, a sheet, a tube, a coil, a spiral, a mesh, a mixture thereof, a combination thereof, and/or an array thereof while conforming its shape to an overall shape of multiple base units, and to emit the first counter waves.

In another exemplary embodiment of this aspect of the invention, a system may include at least one counter unit which is arranged to be disposed in an arrangement which is similar (or identical) to a shape of the base unit and to emit the second counter waves.

In another exemplary embodiment of this aspect of the invention, a system may include at least one counter unit which is arranged to be disposed in an arrangement different from a shape of such a base unit and to emit the second counter waves.

In another exemplary embodiment of this aspect of the invention, a system may include at least one counter unit which is arranged to define a size which is greater than that of such a base unit, to be disposed between the base unit and target space, and then to emit counter electromagnetic waves which are arranged to define phase angles at least partially opposite to those of such harmful waves, to have wave characteristics at least partially similar to those of the harmful waves based on the size and, therefore, to counter the harmful waves in the target space due to the opposite phase angles. In the alternative, such a counter unit may be arranged to define a size which is greater than that of the base unit, to be disposed on an opposite side of the target space with respect to the base unit, and to emit the counter waves described above in this paragraph.

In another aspect of the present invention, an exemplary system may be provided to counter harmful electromagnetic waves irradiated from a base unit of at least one wave source by matching a disposition of the base unit with a disposition of at least one part of the system and by canceling such harmful waves in a target space and/or suppressing the harmful waves from propagating toward the target space, where the base unit includes only portions of the wave source which are responsible for irradiating the harmful waves and affecting paths of the harmful waves therethrough and where the target space is defined between the system and an user.

In one exemplary embodiment of this aspect of the invention, a system may include at least one counter unit which is arranged to be placed in an alignment which matches a direction of propagation of such harmful waves, which matches a direction of electric current flowing in the base unit, which matches a direction of electric voltage applied across the base unit, which matches a direction along a longitudinal axis of the base unit, and/or which matches a direction of a short axis of such a base unit normal to the longitudinal axis, and to emit counter electromagnetic waves, where the counter waves are arranged to define phase angles at least partially opposite to those of the harmful waves, to have wave characteristics at least partially similar to those of such harmful waves due the alignment and, therefore, to counter the harmful waves in the target space due to the opposite phase angles.

In another exemplary embodiment of this aspect of the invention, a system may include at least one counter unit which is arranged to be placed at a position between the target space and base unit and to emit counter electromagnetic waves defining amplitudes less than those of the harmful waves. In another example, the counter unit may be arranged to be disposed at a position on an opposite side of the target space with respect to the base unit and to emit counter electromagnetic waves which define amplitudes greater than those of the harmful waves. In either example, the counter waves are also arranged to define phase angles at least partially opposite to those of the harmful waves, to have wave characteristics at least partially similar to those of such harmful waves due to the position and, therefore, to counter the harmful waves in the target space due to the opposite phase angles.

In another exemplary embodiment of this aspect of the invention, a system may include at least one counter unit which is arranged to be in a disposition enclosing at least a (or an entire) portion of the base unit therein and to emit counter electromagnetic waves. In another example, the counter unit may be arranged to be in a disposition enclosed by at least a (or an entire) portion of the base unit and to emit counter electromagnetic waves. In another example, the counter unit may be arranged to be in a disposition lateral (or side by side) with respect to the base unit and to emit counter electromagnetic waves. In each of these examples, the counter waves are arranged to define phase angles at least partially opposite to those of the harmful waves, to have wave characteristics at least partially similar to those of the harmful waves due the disposition and, therefore, to counter the harmful waves in the target space due to the opposite phase angles.

In another exemplary embodiment of this aspect of the invention, a system may include at least one counter unit which is arranged to be in a disposition symmetric (or asymmetric) with respect to at least a portion of the base unit and then to emit counter electromagnetic waves which are arranged to have phase angles which are at least partially opposite to those of the harmful waves, to have wave characteristics at least partially similar to those of the harmful waves due the disposition and, thus, to counter the harmful waves in the target space due to the opposite phase angles.

In another exemplary embodiment of this aspect of the invention, a system may include at least one counter unit which is arranged to be in a stationary disposition with respect to the base unit, and to emit counter electromagnetic waves which are arranged to define phase angles at least partially opposite to those of the harmful waves, to have wave characteristics at least partially similar to those of the harmful waves due the stationary disposition and, accordingly, to counter the harmful waves in the target space due to the opposite phase angles.

In another exemplary embodiment of this aspect of the invention, a system may include at least one counter unit which is arranged to be in a mobile disposition with respect to the base unit, and then to emit counter electromagnetic waves which are arranged to define phase angles which are at least partially opposite to the harmful waves, to have wave characteristics at least partially similar to those of the harmful waves while moving with respect to such a base unit and, accordingly, to counter the harmful waves in the target space due to the opposite phase angles.

In another aspect of the present invention, an exemplary system may be provided to counter harmful electromagnetic waves irradiated from a base unit of at least one wave source with counter electromagnetic waves by matching the harmful waves with such counter waves along wavefronts thereof and by canceling the harmful waves in a target space and/or suppressing the harmful waves with the counter waves from propagating toward the target space, where the base unit is arranged to include only portions of the wave source which are responsible for irradiating the harmful waves and affecting paths of the harmful waves therethrough, while the target space is formed between the system and an user.

In one exemplary embodiment of this aspect of the invention, a system may include at least one counter unit which is arranged to be disposed based on a preset arrangement along (or relative to) at least one of the above wavefronts, and to emit the counter waves which are arranged to have phase angles which are at least partially opposite to those of such harmful waves, to at least partially match the wavefronts of the harmful waves due to such an arrangement in the target space and, therefore, to counter such harmful waves due to the opposite phase angles in the target space. It is appreciated that such counter waves will be referred to as the "counter waves of the third type" or simply "third counter waves" hereinafter.

In another exemplary embodiment of this aspect of the invention, a system may be provided in various arrangements. In one example, a system may include a single counter unit which is arranged to be disposed in a front arrangement defined along at least one of such wavefronts, and then to emit the counter waves defining amplitudes less than those of the harmful waves, where the counter unit is disposed between the base unit and the target space in the arrangement. In another example, such a system may include multiple counter units each of which is arranged to be disposed in such a front arrangement along at least one of the wavefronts and to emit the counter waves defining amplitudes less than those of the harmful waves, where the counter unit is disposed between the base unit and the target space in the arrangement. In both examples, the counter units are arranged to emit the third counter waves.

In another exemplary embodiment of this aspect of the invention, a system may be provided in various arrangements. In one example, a system may include a single counter unit which is arranged to be disposed in a rear arrangement and to emit the counter waves defining amplitudes greater than those of the harmful waves, where such a counter unit is disposed on an opposite side of the target space relative to the base unit in the arrangement. In another example, a system may include multiple counter units each of which is arranged to be disposed in a rear arrangement and to emit the counter waves defining amplitudes greater than those of the harmful waves, where the counter units may be disposed on an opposite side of the target space with respect to the base unit in the arrangement. In both examples, the counter units are arranged to emit the third counter waves.

In another exemplary embodiment of this aspect of the invention, a system may be provided in various arrangements. In one example, a system may include a single counter unit which is arranged to be disposed in a front arrangement along one of such wavefronts, and to emit the counter waves defining amplitudes less than those of the harmful waves, where the wavefronts are defined by the harmful waves irradiated by multiple base units and where the counter unit is disposed between the base unit and target space in such an arrangement. In another example, a system may have multiple counter units each of which is arranged to be disposed in a front arrangement along one of the above wavefronts and to emit the counter waves defining amplitudes less than those of the harmful waves, where the wavefronts are defined by the harmful waves irradiated by multiple base units and where all of the counter units are disposed between the base unit and target space in such an arrangement. In both examples, the counter units are arranged to emit the third counter waves.

In another exemplary embodiment of this aspect of the invention, a system may be provided in various arrangements. In one example, a system may include a single counter unit which is arranged to be disposed in a rear arrangement and then to emit the counter waves with amplitudes greater than those of the harmful waves, where such harmful waves are defined by such harmful waves which are irradiated by multiple base units and where such a counter unit is disposed on an opposite side of the target space with respect to the base unit in such an arrangement. In another example, a system may include multiple counter units which are arranged to be disposed in a rear arrangement and to emit the counter waves defining amplitudes greater than those of the harmful waves, where the wavefronts are formed by such harmful waves which are irradiated by multiple base units and where the counter units are disposed on an opposite side of the target space relative to the base unit in the arrangement. In both examples, the counter units are arranged to emit the third counter waves.

In another aspect of the present invention, an exemplary system may be provided to counter harmful electromagnetic waves irradiated from a base unit of at least one wave source with counter electromagnetic waves by matching the harmful waves along their wavefronts by the counter waves and by canceling the harmful waves in a target space by the counter waves and/or suppressing the harmful waves from propagating to the target space with the counter waves, where the base unit is arranged to include only portions of the wave source which are responsible for irradiating the harmful waves and for affecting paths of the harmful waves therethrough, while the target space is defined between the system and an user.

In one exemplary embodiment of this aspect of the invention, such a system may be provided in various arrangements. In one example, such a system may include a single counter unit which is arranged to emit the counter waves and to be incorporated in a preset arrangement which is defined along at least one of the wavefronts. In another example, a system may include a single counter unit which is arranged to emit the counter waves and to be incorporated in a preset arrangement which is defined along at least one of the wavefronts which are formed by multiple base units of multiple wave sources. In another example, a system may include multiple counter units which are arranged to emit the counter waves and to be disposed in a preset arrangement which is defined along at least one of the wavefronts. In another example, a system may include multiple counter units which are arranged to emit the counter waves and to be disposed in a preset arrangement which is defined along at least one of the wavefronts which are defined by multiple base units of multiple wave sources. In all of the examples, the counter units are arranged to emit the third counter waves.

In another exemplary embodiment of this aspect of the invention, a system may be provided in various arrangements. In one example, a system may include a single counter unit which is arranged to emit the counter waves and to be disposed between the target space and base unit based upon an arrangement which is in turn arranged to be defined along at least one of such wavefronts and to be wider than the base unit. In another example, such a system may include multiple counter units each of which is arranged to emit the counter waves and to be disposed between the base unit and target space in an arrangement which is in turn arranged to be formed along at least one of the wavefronts and which is also arranged to be wider than the base unit. In both examples, such counter units are arranged to emit the third counter waves.

In another exemplary embodiment of this aspect of the invention, a system may be provided in various arrangements. In one example, a system may include a single counter unit which is arranged to emit the counter waves and to be disposed between the target space and base unit based upon an arrangement which is in turn arranged to be defined along at least one of such wavefronts and to be narrower than the base unit. In another example, a system may include multiple counter units each of which is arranged to emit such counter waves and to be disposed between the base unit and target space in an arrangement which is in turn arranged to be defined along at least one of the wavefronts and which is also arranged to be narrower than the base unit. In both examples, such counter units are arranged to emit the third counter waves.

In another exemplary embodiment of this aspect of the invention, a system may be provided in various arrangements. In one example, a system may include a single counter unit which is arranged to emit the counter waves and to be disposed between the base unit and target space based upon an arrangement which is in turn arranged to be similar (or identical, conforming) to that of at least one of the wavefronts. In another example, a system may include a single counter unit which is arranged to emit such counter waves and to be disposed on an opposite side of the target space with respect to the base unit in an arrangement which is arranged to be similar (or identical, conforming) to that of at least one of the wavefronts. In another example, a system may include multiple counter units each of which is arranged to emit such counter waves and to be disposed between the base unit and target space in an arrangement which is arranged to be similar (or identical, conforming) to at least one of the wavefronts. In yet another example, a system may include multiple counter units each of which is arranged to emit the counter waves and to be disposed on an opposite side of the target space with respect to the base unit in an arrangement which is arranged to be similar (or identical, conforming) to at least one of the wavefronts. In all of these examples, such counter units are arranged to emit the third counter waves.

In another exemplary embodiment of this aspect of the invention, a system may be provided in various arrangements. In one example, such a system may include at least one counter unit which is arranged to emit the counter waves, to define a shape not similar (or identical, conforming) to that of at least one of the wavefronts, and to be placed between the base unit and target space based on an arrangement which is arranged to not be similar (or identical, conforming) to that of at least one of the wavefronts. In another example, a system may include at least one counter unit which is arranged to emit such counter waves, to define a shape not similar (or identical, conforming) to that of at least one of the wavefronts, and to be disposed on an opposite side of the target space relative to the base unit in an arrangement which is arranged to not be similar (or identical, conforming) to that of at least one of the wavefronts. In both examples, such counter waves are arranged to have phase angles which are at least partially opposite to those of the harmful waves, to at least partially match the wavefronts of such harmful waves due to the shape in the target space and, accordingly, to counter the harmful waves due to the opposite phase angles in the target space.

In another exemplary embodiment of this aspect of the invention, a system may be provided in various arrangements. In one example, such a system may include at least one counter unit which is arranged to emit the counter waves and to be disposed in an arrangement enclosing therein at least a portion (or an entire portion) of such wavefronts. In another example, a system may include at least one counter unit which is arranged to emit the counter waves and to be disposed in an arrangement enclosed by at least a portion (or an entire portion) of the wavefronts. In another example, a system may include at least one counter unit which is arranged to emit the counter waves and to be disposed in a lateral (or side-by-side) arrangement relative to at least a (or an entire) portion of the wavefronts. In all of these examples, the counter units are arranged to emit the third counter waves.

In another exemplary embodiment of this aspect of the invention, a system may be provided in various arrangements. In one example, such a system may include at least one counter unit which is arranged to emit the counter waves while being disposed along at least one of the wavefronts in an arrangement which defines a wire, a strip, a sheet, a tube, a coil, a spiral, a mesh, a mixture thereof, a combination thereof, and/or an array thereof and being disposed between the base unit and target space. In another example, a system may include at least one counter unit which is arranged to emit the counter waves while being disposed along at least one of the wavefronts in an arrangement of a wire, a strip, a sheet, a tube, a coil, a spiral, a mesh, a mixture thereof, a combination thereof, and/or an array thereof and being disposed on an opposite side of the target space with respect to the base unit. In both examples, the counter units are arranged to emit the third counter waves.

In another exemplary embodiment of this aspect of the invention, a system may include at least two counter units each of which is arranged to disposed in an arrangement defined on a far side of the target space with respect to the base unit and to emit the counter waves such that a sum of the counter waves individually emitted by the counter units defines the wavefronts having greater radii of curvature than the wavefronts of the individual counter waves. At least one or both of such counter units may then be arranged to emit the third counter waves.

In another aspect of the present invention, an exemplary system may be provided to counter harmful electromagnetic waves irradiated from a base unit of at least one wave source with counter electromagnetic waves by matching the harmful waves along their wavefronts by the counter waves and by canceling the harmful waves in a target space by the counter waves and/or suppressing the harmful waves from propagating to the target space with the counter waves, where the base unit is arranged to include only portions of the wave source which are responsible for irradiating the harmful waves and for affecting paths of the harmful waves therethrough, while the target space is defined between the system and an user.

In one exemplary embodiment of this aspect of the invention, such a system may be provided in various arrangements. In one example, such a system may include a single counter unit which may be arranged to define a shape matching that of a single base unit and to emit such counter waves. In another example, a system may include multiple counter units which are arranged to define an overall shape matching that of a single base unit and to emit the counter waves. In both example, the counter waves are arranged to define phase angles at least partially opposite to those of the harmful waves, to at least partially match the wavefronts of the harmful waves due to the shapes in the target space and, therefore, to counter the harmful waves due to the opposite phase angles in the target space.

In another exemplary embodiment of this aspect of the invention, a system may be provided in various arrangements. In one example, a system may include a single counter unit which is arranged to define a shape matching an overall shape and/or arrangement of at least one but not all of multiple base units and to emit the counter waves. In another example, a system may include a single counter unit which is arranged to define a shape matching an overall shape and/or an overall arrangement of all of multiple base units and to emit such counter waves. In another example, a system may include multiple counter units which are arranged to define an overall shape which matches an overall shape and/or an overall arrangement of at least one but not all of multiple base units, and to emit the counter waves. In another example, a system may include multiple counter units which are arranged to define an overall shape which matches an overall shape and/or arrangement of all of multiple base units and to emit the counter waves. In all of these examples, the counter waves are further arranged to have phase angles at least partially opposite to those of such harmful waves, to at least partially match the wavefronts of such harmful waves due to such a shape and/or arrangement in the target space and, accordingly, to counter the harmful waves due to the opposite phase angles in the target space.

In another exemplary embodiment of this aspect of the invention, a system may be provided in various arrangements. In one example, a system may include a single counter unit which is arranged to define a preset shape, to be disposed based on a preset arrangement with respect to a single base unit, and to emit the counter waves, where such a shape and/or arrangement may then be arranged to match at least one of such wavefronts. In another example, a system may include multiple counter units which are arranged to define a preset overall shape, to be placed in a preset arrangement with respect to multiple base units, and to emit such counter waves, where the shape and/or arrangement may be arranged to match at least one of the wavefronts. In both examples, the counter waves are arranged to have wavefronts similar (or identical) to such a shape and/or arrangement, to have phase angles at least partially opposite to those of the harmful waves while matching their wavefronts with those of the harmful waves in the target space and, accordingly, to counter the harmful waves due to the opposite phase angles in the target space.

In another exemplary embodiment of this aspect of the invention, a system may be provided in various arrangements. In one example, a system may include a single counter unit shaped, sized, and disposed to emit the counter waves matching at least one of such wavefronts of the harmful waves from a single base unit. In another example, such a system may include multiple counter units which are shaped, sized, and disposed to emit such counter waves a sum of which is arranged to match at least one of the wavefronts of the harmful waves emitted by a single base unit. In another example, a system may have a single counter unit which also is shaped, sized, and disposed to emit the counter waves matching at least one of such wavefronts of a sum of the harmful waves irradiated by multiple base units of multiple sources. In another example, a system may include multiple counter units which are shaped, sized, and disposed to emit the counter waves matching at least one of such wavefronts of a sum of the harmful waves irradiated from multiple base units of multiple sources. In all examples, the counter waves are arranged to form wavefronts which are similar (or identical) to such a shape, size, and/or disposition of the counter unit, to have phase angles at least partially opposite to those of the sum of the harmful waves while matching the wavefronts in the target space and, accordingly, to counter the harmful waves due to the opposite phase angles therein.

In another aspect of the present invention, an exemplary system may be provided to counter harmful electromagnetic waves irradiated from a base unit of at least one wave source with counter electromagnetic waves emitted by another part of the system and by canceling the harmful waves in a target space and/or suppressing the harmful waves by the counter waves from propagating to the target space, where the base unit is arranged to include only portions of the wave source which are responsible for irradiating the harmful waves and affecting paths of the harmful waves therethrough, where the harmful waves are arranged to propagate while defining multiple wavefronts, and where the target space is formed between the system and an user.

In one exemplary embodiment of this aspect of the invention, a system may include at least one counter unit which is arranged to define a preset shape and/or size, to be disposed in an arrangement defined along at least a portion of at least one of the wavefronts, and then to emit the counter waves propagating along the wavefronts in the target space, where the counter waves may be arranged to define phase angles at least partially opposite to those of such harmful waves while matching at least one of the wavefronts of the harmful waves and, therefore, to counter the harmful waves due to the opposite phase angles in the target space.

In another exemplary embodiment of this aspect of the invention, a system may be provided in various arrangements. In one example, a system may include multiple counter units each of which is arranged to define a preset shape and size and which are arranged to be disposed in an arrangement defined along at least a portion of at least one of the wavefronts and then to emit the counter waves propagating along the wavefronts in the target space. In another example, such a system may have multiple counter units each of which is arranged to define a preset shape and/or size and which are arranged to be disposed in an arrangement not conforming to any of such wavefronts but to emit the counter waves propagating along the wavefronts in the target space. In both examples, a sum of the counter waves which are emitted by at least two of the counter units may be arranged to have phase angles at least partially opposite to those of the harmful waves while matching the wavefonts of the harmful waves and, therefore, to counter the harmful waves due to the opposite phase angles in the target space.

In another aspect of the present invention, an exemplary speaker system may be provided to include at least one speaker with multiple base units irradiating harmful electromagnetic waves when electric currents flows therein and to be capable of countering the harmful waves by canceling such harmful waves in a target space and/or suppressing the harmful waves from propagating toward the target space, where the base units are arranged to include only portions of the speaker responsible for irradiating the harmful waves and affecting paths of the harmful waves therethrough and where the target space is defined between an user and the system.

In one exemplary embodiment of this aspect of the invention, a system may include at least one cone, at least one voice coil, at least one permanent magnet, and at least one counter unit. The cone is arranged to define at least two ends, while the voice coil is arranged to form or include at least one electromagnet formed around one of the ends of the cone, to flow therein a source signal, to serve as one of such base units, and to emit such harmful waves while defining therearound dynamic magnetic fields and serving as one of the base units in response to the source signal. The permanent magnet is arranged to form static dynamic fields therearound, to magnetically couple with the voice coil, and to serve as another of such base units for transmitting the harmful waves therethrough. An interaction between such static and dynamic magnetic fields is then arranged to vibrate the cone and to generate audible sound in response to the source signal. In one example, the counter unit is arranged to define a shape identical (or similar) to the voice coil and/or magnet, and then to emit counter electromagnetic waves defining phase angles at least partially opposite to those of the harmful waves, defining wave characteristics at least partially similar to those of the harmful waves due to the shape and, therefore, countering the harmful waves based upon the opposite phase angles in the target space. In another example, the counter unit is arranged to be disposed in an arrangement defined along at least one of multiple wavefronts of the harmful waves formed by the voice coil and permanent magnet and to emit counter electromagnetic waves defining phase angles which are at least partially opposite to those of the harmful waves, defining wave characteristics which are also at least partially similar to those of the harmful waves due to the arrangement and, accordingly, countering the harmful waves due to the opposite phase angles in the target space.

In another exemplary embodiment of this aspect of the invention, a system may include at least one diaphragm, at least two grids, and at least one counter unit. Such a diaphragm is arranged to be electrically charged and to define static electric fields therearound while serving as one of such base units when vibrating. Such grids are arranged to be disposed on opposite sides of the diaphragm, to flow therein a source signal while forming therebetween dynamic electric fields as a response to the source signal, to vibrate the diaphragm while generating audible sound due to an interaction between the static and dynamic electric fields, and to emit the harmful waves in response to the source signal while serving as another of the base units. In one example, such a counter unit is arranged to define a shape identical (or similar) to the diaphragm and/or grids and to emit counter electromagnetic waves having phase angles which are at least partially opposite to those of the harmful waves, having wave characteristics at least partially similar to those of the harmful waves due to the shape and, therefore, countering the harmful waves based upon the opposite phase angles in the target space. In another example, the counter unit is arranged to be disposed in an arrangement defined along at least one of multiple wavefronts of the harmful waves defined by the diaphragm and/or grids, and to emit counter electromagnetic waves having phase angles at least partially opposite to those of the harmful waves, defining wave characteristics at least partially similar to those of the harmful waves based on such an arrangement and, accordingly, countering the harmful waves due to the opposite phase angles in the target space.

In another exemplary embodiment of this aspect of the invention, a system may include at least one piezoelectric plate, at least two electrodes, at least one counter unit, and so on. The piezoelectric plate is arranged to convert source voltage into vibration thereof while functioning as one of the base units when vibrating, whereas the electrodes are arranged to be electrically coupled to opposite sides of the piezoelectric plate, to apply such source voltage across such a plate, and then to vibrate along with the plate in response to the source voltage while emitting such harmful waves as a response to the source signal while functioning as another of the base units. In one example, the counter unit may be arranged to define a shape identical (or similar) to the piezoelectric plate and/or electrodes and to emit counter electromagnetic waves which define phase angles at least partially opposite to those of the harmful waves, which define wave characteristics at least partially similar to those of the harmful waves due to the shape and, therefore, which counter the harmful waves due to the opposite phase angles in the target space. In another example, the counter unit is disposed in an arrangement along at least one of multiple wavefronts of the harmful waves defined by at least one of the piezoelectric plate and electrodes, and to emit counter electromagnetic waves having phase angles at least partially opposite to those of the harmful waves, defining wave characteristics at least partially similar to those of the harmful waves due to the arrangement and, accordingly, countering the harmful waves due to the opposite phase angles in the target space.

In another exemplary embodiment of this aspect of the invention, a system may include at least one body, the speaker, and at least one counter unit. Such a body is arranged to be disposed over an ear of the user and/or into an ear canal thereof, while the speaker is arranged to be supported by the body and to include the base units for emitting the harmful waves. In one example, the counter unit is arranged to define a shape identical (or similar) to at least one of the base units of the speaker and to emit counter electromagnetic waves defining phase angles at least partially opposite to those of such harmful waves, having wave characteristics which are at least partially similar to those of the harmful waves due to the shape and, accordingly, countering such harmful waves due to the opposite phase angles in the target space. In another example, the counter unit is instead arranged to be disposed in an arrangement defined along at least one of multiple wavefronts of the harmful waves formed by the base units, and to emit counter electromagnetic waves which define phase angles at least partially opposite to those of the harmful waves, defining wave characteristics at least partially similar to those of the harmful waves due to the arrangement and, accordingly, countering the harmful waves due to the opposite phase angles in the target space.

In another aspect of the present invention, a communication system may be provided to include multiple base units irradiating harmful electromagnetic waves and to be also capable of countering the harmful waves by canceling the waves in a target space and/or suppressing the harmful waves from propagating toward the target space, where such base units are arranged to include only portions of the system responsible for irradiating the harmful waves and affecting paths of such harmful waves therethrough and where the target space is defined between an user and system.

In one exemplary embodiment of this aspect of the invention, such a system may have a main body, a handset, at least one input module, at least one output module, and at least one counter unit. The handset is arranged to electrically connected to the main body by wire, while the input module is arranged to be disposed in the handset, to have at least one microphone serving as one of the base units, and then to convert an audible sound of the user into an output signal. Such an output module is arranged to be disposed in the handset, to have at least one speaker serving as another of the base units, and to convert an external source signal into audible sound while irradiating the harmful waves from the base unit. In one example, the counter unit is arranged to be disposed inside the handset, to define a shape identical (or similar) to at least one of the base units of the input and/or output modules, and then to emit counter electromagnetic waves which define phase angles at least partially opposite to those of the harmful waves, which include wave characteristics at least partially similar to those of the harmful waves due to the shape and, thus, which counter the harmful waves due to the opposite phase angles in the target space. In another example, the counter unit is arranged to be disposed in an arrangement formed along at least one of multiple wavefronts of the harmful waves formed by the base units of the output module, and to emit counter electromagnetic waves defining phase angles at least partially opposite to those of the harmful waves, defining wave characteristics at least partially similar to those of the harmful waves due to the arrangement and, accordingly, countering the harmful waves due to the opposite phase angles in the target space.

In another exemplary embodiment of this aspect of the invention, such a system may include a handset, at least one input module, at least one transmitting module, at least one receiving module, at least one output module, and at least one counter unit. The input module is arranged to be disposed in the handset, to include at least one microphone serving as one of such base units, and to convert an audible sound of the user into an output signal, while the transmitting module is arranged to wirelessly transmit the output signal. Such a receiving module is arranged to wirelessly receive a source signal, and the output module is arranged to be disposed in the handset, to have at least one speaker serving as another of the base units, and then to convert the source signal into audible sound while irradiating the harmful waves from the base unit. In one example, the counter unit is arranged to be disposed in the handset, to also define a shape identical to (or similar to) at least one of the base units of the input and/or output modules, and then to emit counter electromagnetic waves defining phase angles at least partially opposite to those of the harmful waves, defining wave characteristics at least partially similar to those of the harmful waves due to the shape and, therefore, countering the harmful waves due to the opposite phase angles in the target space. In another example, the counter unit is arranged to be disposed in an arrangement defined along at least one of multiple wavefronts of such harmful waves formed by the base units of the output module and then to emit counter electromagnetic waves which define phase angles at least partially opposite to those of the harmful waves, which also have wave characteristics at least partially similar to those of such harmful waves due to the arrangement and, accordingly, countering the harmful waves due to the opposite phase angles in the target space.

In another aspect of the present invention, an exemplary system may be provided to include at least one motor including multiple base units irradiating harmful electromagnetic waves and to be also capable of countering the harmful waves by suppressing such harmful waves from propagating to a target space and/or canceling the harmful waves in the target space, where such base units include only portions of the motor responsible for irradiating the harmful waves and for affecting paths of the harmful waves therethrough and where the target space is defined between an user and system.

In one exemplary embodiment of this aspect of the invention, a system may include at least one body, at least one stator, at least one rotor, and at least one counter unit. The stator includes at least one permanent magnet which is arranged to fixedly couple with the body, to generate static magnetic fields therearound, and to serve as one of the above base units while transmitting the harmful waves therethrough. The rotor has at least one electromagnet which is arranged to be movably disposed in the stator, to define dynamic magnetic fields therearound when electric current flows therein, and to rotate due to an interaction between such static and dynamic magnetic fields when the current flows therein while emitting the harmful waves and serving as another of such base units. In one example, the counter unit is arranged to define a shape identical (or similar) to the stator and/or rotor and to emit counter electromagnetic waves which define phase angles at least partially opposite to those of such harmful waves, which also have wave characteristics at least partially similar to those of the harmful waves due to the shape and, therefore, which counter the harmful waves due to the opposite phase angles in the target space. This counter unit is to be referred to as the "counter unit of the first type" or "first counter unit" hereinafter. In another example, the counter unit is arranged to be disposed in an arrangement formed along at least one of multiple wavefronts of the harmful waves formed by the rotor and/or stator and to emit counter electromagnetic waves defining phase angles at least partially opposite to those of the harmful waves, defining wave characteristics at least partially similar to those of the harmful waves due to the arrangement and, accordingly, countering the harmful waves due to the opposite phase angles in the target space. Such a counter unit is to be referred to as the "counter unit of the second type" or "second counter unit" hereinafter.

In another exemplary embodiment of this aspect of the invention, a system may include at least one body, at least one stator, at least one rotor, and then at least one first counter unit or at least one second counter unit. The stator includes at least one first electromagnet which is arranged to fixedly couple to the body, to generate first dynamic magnetic fields therearound when electric current flows therein, and to serve as one of the above base units while transmitting the harmful waves. The rotor includes at least one second electromagnet which is arranged to be movably disposed in the stator, to define second dynamic magnetic fields therearound when electric current flows therein, and to rotate due to an interaction between such first and second dynamic magnetic fields when the current flows therein while emitting the harmful waves and serving as another of the base units. Therefore, such a first or second counter unit may counter the harmful waves by the counter waves.

In another exemplary embodiment of this aspect of the invention, a system may include at least one body, at least one stator, at least one rotor, and then at least one first counter unit or at least one second counter unit. Such a stator forms or includes at least one electromagnet which is arranged to fixedly couple with the body, to generate dynamic magnetic fields therearound when electric current flows therein, and to serve as one of the base units while transmitting the harmful waves. The rotor includes at least one permanent magnet which is arranged to movably couple with the stator, to define static magnetic fields therearound, and to rotate due to an interaction between the static and dynamic magnetic fields as the current flows in the stator while transmitting such harmful waves therethrough and serving as another of the base units. Therefore, such a first or second counter unit may counter the harmful waves by the counter waves.

In another exemplary embodiment of this aspect of the invention, a system may include at least one body, at least one stator, at least one rotor, and then at least one first counter unit or at least one second counter unit. The stator has at least one electromagnet which is arranged to fixedly couple to the body, to generate dynamic magnetic fields therearound when electric current flows therein, and to serve as one of the base units while transmitting such harmful waves. The rotor includes at least one electric conductor which is arranged to movably couple with such a stator, to induce electric current in response to the dynamic magnetic fields, and to rotate due to an interaction between such dynamic magnetic fields and counterbalancing magnetic fields defined by the induced current while transmitting the harmful waves therethrough and serving as another of the base units. Therefore, such a first or second counter unit may counter the harmful waves by the counter waves.

In another exemplary embodiment of this aspect of the invention, a system may include at least one body, at least one stator, at least one rotor, and then at least one first counter unit or at least one second counter unit. The stator includes or forms at least one electromagnet which is arranged to be fixedly coupled to the body, to generate dynamic magnetic fields therearound as electric current flows therein, and to serve as one of the base units while transmitting the harmful waves. The rotor has at least one permanent magnet which is arranged to movably couple to the stator, to form static magnetic fields therearound, and then to linearly translate due to an interaction between the static and dynamic magnetic fields as the current flows in the stator while transmitting such harmful waves therethrough and serving as another of the base units. Therefore, such a first or second counter unit may counter the harmful waves by the counter waves.

In another aspect of the present invention, a system may be fabricated to include multiple base units emitting harmful electromagnetic waves and to counter the harmful waves irradiated from such base units by suppressing the harmful waves from propagating to a target space and/or canceling the harmful waves in the target space, where the base units are arranged to include only portions of the system responsible for irradiating the harmful waves and for affecting paths of such harmful waves therethrough and where the target space is also defined between an user and system.

In one exemplary embodiment of this aspect of the invention, such a system may have a main body, at least one electric motor, at least one shaft, and then at least one first counter unit or at least one second counter unit. Such an electric motor is arranged to be supported by the body, to include at least one rotor and at least one stator both serving as the base units, and to rotate (or translate) the rotor when electric current flows therein. The shaft is arranged to be movably retained by the body, to movably couple with the rotor, and to rotate along with such a rotor while generating electromotive force. Therefore, such a first or second counter unit may counter the harmful waves by the counter waves.

In another exemplary embodiment of this aspect of the invention, such a system may have a main body with at least one mesh, at least one blade, at least one electric motor, and then at least one first counter unit or at least one second counter unit. The blade is arranged to be movably disposed under the mesh and to cut hair protruding through the mesh, while the electric motor is arranged to be supported by the body, to include at least one rotor and at least one stator both serving as such base units, to be mechanically coupled to the blade, and to rotate (or translate) the blade as electric current flows therein, thereby cutting the hair. Therefore, such a first or second counter unit may counter the harmful waves by the counter waves.

In another exemplary embodiment of this aspect of the invention, a system may have a handle, a brush, at least one electric motor, and then at least one first (or second) counter unit. The brush is arranged to be movably disposed on one end of the handle, while the electric motor is arranged to be supported by the body, to include at least one rotor and at least one stator both serving as the base units, to mechanically couple to the brush, and to rotate (or translate) the brush when electric current flows therein. Therefore, such a first or second counter unit may counter the harmful waves by the counter waves.

In another exemplary embodiment of this aspect of the invention, a system may include a main body, at least one fan, at least one electric motor, at least one heating unit, and then at least one first counter unit or at least one second counter unit. The main body includes an air pathway with at least one air inlet and at least one air outlet, while the fan is disposed along the air pathway. The electric motor is arranged to be supported by such a body, to include at least one rotor and at least one stator both serving as the base units, to mechanically couple with the fan, and to rotate (or translate) the fan for taking air in through the air inlet, moving the air through the air pathway, and then discharging such air through the air outlet as electric current flows therein. The heating unit is arranged to be disposed along the air pathway and to heat the air flowing through the air pathway, thereby discharging heated air from the air outlet to one of hair of the user and cloth stored in the body. Therefore, such a first or second counter unit may counter the harmful waves by the counter waves.

In another exemplary embodiment of this aspect of the invention, a system may include a main body, a chamber, at least one fan, at least one electric motor, and then at least one first counter unit or at least one second counter unit. The main body includes an air pathway with at least one air inlet and at least one air outlet, the chamber is arranged to be disposed along the pathway, and the fan is disposed along the air pathway. The electric motor is arranged to be supported by the body, to have at least one rotor and at least one stator both serving as the base units, to be mechanically coupled to the fan, to rotate the fan for taking air in through the air inlet, moving such air through the air pathway while creating vacuum inside the chamber, and discharging the air through the air outlet when electric current flows therein, and to collect undesirable particles in the chamber. Accordingly, such a first or second counter unit may counter the harmful waves by the counter waves.

In another exemplary embodiment of this aspect of the invention, a system may include a main body, at least one applicator, at least one electric motor, and then at least one first counter unit or at least one second counter unit. The applicator is arranged to movably couple with the body, while the electric motor is arranged to be supported by the body, to have therein at least one rotor and at least one stator both of which serve as the base units, to be mechanically coupled to the applicator, and to rotate (or translate) the applicator as electric current flows therein. Therefore, such a first or second counter unit may counter the harmful waves by the counter waves. Such a system is arranged to be used as an electric can opener where the applicator is arranged to hold and rotate a can, an electric drill including a shaft where the applicator is arranged to angularly rotate the shaft, an electric screw driver with a shaft where the applicator is arranged to rotate the shaft, a sander with a shaft where the applicator is arranged to move (or translate) the shaft, a dish washer where the motor is arranged to transport water from one to another location inside the body and where the applicator is arranged to squirt (or spray) the water in the body, a cloth washer where the applicator is arranged to rotate at least one of the shaft and at least a portion of the body, and the like.

In another exemplary embodiment of this aspect of the invention, a system may include a main body, at least one electric motor, at least one compressor, and then at least one first counter unit or at least one second counter unit. The main body includes at least one chamber, and the electric motor is arranged to be supported by the body, to have at least one rotor and at least one stator both of which serve as the base units, to be mechanically coupled to the applicator, and to rotate (or translate) such an applicator when electric current flows therein. The compressor is arranged to compress and then expand at least one gas while generating cold air and supplying the cold air into or out of the chamber. Therefore, such a first or second counter unit may counter the harmful waves by the counter waves. Such a system is arranged to be used as a refrigerator, a cooler, a freezer, and/or an air conditioner each capable of generating the cold air.

In another aspect of the present invention, an exemplary generating system may be fabricated to include multiple base units emitting harmful electromagnetic waves while generating AC and/or DC electricity and to also counter the harmful waves irradiated by the base units by canceling the harmful waves in a target space and/or suppressing the harmful waves from propagating to the target space, where the base units are arranged to include only portions of the system responsible for irradiating the harmful waves and for affecting paths of the harmful waves therethrough and where the target space is defined between an user and system.

In one exemplary embodiment of this aspect of the invention, such a system may have at least one body, at least one stator, at least one rotor, and then at least one first counter unit or at least one second counter unit. Such a stator is arranged to couple with the body and to generate first magnetic fields therearound, while the rotor is arranged to be movably coupled to the body, to generate second magnetic fields therearound, to rotate in response to external force, and to generate such electricity in response to the force due to an interaction between the first and second magnetic fields. Therefore, such a first or second counter unit may counter the harmful waves by the counter waves.

In another exemplary embodiment of this aspect of the invention, a system may include at least one body of an automobile or aircraft, at least one stator, at least one rotor and then at least one first counter unit or at least one second counter unit. The stator is arranged to be disposed inside such an automobile or aircraft and to generate first magnetic fields therearound, while the rotor is arranged to movably couple with the stator, to generate second magnetic fields therearound, to rotate in response to external force, and to generate electricity in response to such force due to an interaction between the first and second magnetic fields. Therefore, such a first or second counter unit may counter the harmful waves by the counter waves.

In another aspect of the present invention, an exemplary system may be provided to include at least one coil of conductive wire irradiating harmful electromagnetic waves as electric current flows therein and to counter the harmful waves irradiated from the coil by suppressing such harmful waves from propagating to a target space and/or canceling the harmful waves in the target space, where the base units are arranged to include only portions of the system responsible for irradiating such harmful waves and affecting paths of the harmful waves therethrough and where the target space is defined between an user and system.

In one exemplary embodiment of this aspect of the invention, a system may include at least one insert, the coil, and then at least one first counter unit or at least one second counter unit. The insert is arranged to include at least one ferromagnetic, paramagnetic material, and/or ferrimagnetic material therein, while the coil is arranged to be wound along a preset portion of the insert in a preset direction and in a preset number of turns and to emit the harmful waves when the current flows therein. In one example, such a counter unit is arranged to define a shape identical (or similar) to the coil and to emit counter electromagnetic waves which define phase angles at least partially opposite to those of such harmful waves, which also have wave characteristics at least partially similar to those of the harmful waves due to the shape and, therefore, which counter the harmful waves due to the opposite phase angles in the target space. In another example, the counter unit is instead arranged to be disposed in an arrangement formed along at least one of multiple wavefronts of the harmful waves formed by the coil and to emit counter electromagnetic waves which define phase angles at least partially opposite to those of the harmful waves, which have wave characteristics at least partially similar to those of the harmful waves due to the arrangement and, accordingly, which counter the harmful waves due to the opposite phase angles in the target space.

In another exemplary embodiment of this aspect of the invention, a system may include at least one insert, at least two coils, and at least one counter unit. The insert is arranged to include therein at least one ferromagnetic, paramagnetic, and/or diamagnetic material and to define thereon at least two sides. One of the coils is arranged to be wound around a first side of the insert in a preset direction and in a preset number of turns, another of the coils is arranged to be wound around a second side of the insert in another preset direction and in another preset number of turns, and both of such coils are arranged to be spaced away from each other and to emit the harmful waves as the current flows therein. In one example, the counter unit is arranged to define a shape identical (or similar) to at least one of the coils and to emit counter electromagnetic waves which have phase angles at least partially opposite to those of the harmful waves, which include wave characteristics at least partially similar to those of the harmful waves due to the shape and, therefore, which counter such harmful waves due to the opposite phase angles in the target space. This counter unit is to be referred to as the "counter unit of the third type" or "third counter unit" hereinafter. In another example, the counter unit is further arranged to be disposed in an arrangement formed along at least one of multiple wavefronts of such harmful waves formed by the coils and to emit counter electromagnetic waves defining phase angles at least partially opposite to those of the harmful waves, having wave characteristics at least partially similar to those of the harmful waves due to the arrangement and, accordingly, countering the harmful waves due to the opposite phase angles in the target space. Such a counter unit is to be referred to as the "counter unit of the fourth type" or "fourth counter unit" hereinafter.

In another exemplary embodiment of this aspect of the invention, a system may include a body, at least one insert, at least two coils, and at least one third counter unit or at least one fourth counter unit. The body is arranged to terminate in at least two electric couplers one of which couples with a source of electricity and another of which couples with an electric device. The insert is arranged to be disposed in the body and to include at least one ferromagnetic, paramagnetic, and/or ferrimagnetic material and to define at least two sides thereon. One of the coils is arranged to be wound around a first side of the insert in a preset direction and in a preset number of turns, another of the coils is then arranged to be wound around a second side of the insert along another preset direction as well as in another preset number of turns, and both of such coils are arranged to be spaced away from each other and to emit the harmful waves as the current flows therein. Accordingly, such a third or fourth counter unit may counter the harmful waves by the counter waves.

In another aspect of the present invention, a wave emitting system may be provided to include at least one base unit irradiating harmful electromagnetic waves and to counter the harmful waves by suppressing the harmful waves from propagating toward a target space and/or canceling the harmful waves in the target space, where such a base unit is arranged to include only portions of the system responsible for irradiating the harmful waves and affecting paths of the harmful waves therethrough and where the target space is defined between an user and system.

In one exemplary embodiment of this aspect of the invention, a system may have a main body, at least one emitting unit, and at least one counter unit. The emitting unit is arranged to be retained in or inside such a body and to emit visible light waves while serving as the base unit for irradiating the harmful waves when electric current flows therein, where at least a portion of such an emitting unit is arranged to be exposed through the body for propagating such light waves to an exterior of the body. In one example, the counter unit is arranged to define a shape identical (or similar) to the emitting unit and to emit counter electromagnetic waves defining phase angles at least partially opposite to those of the harmful waves, defining wave characteristics at least partially similar to those of such harmful waves due to the shape and, accordingly, countering such harmful waves due to the opposite phase angles in the target space. This counter unit is to be referred to as the "counter unit of the fifth type" or "fifth counter unit" hereinafter. In another example, the counter unit is arranged to be disposed in an arrangement defined along at least one of multiple wavefronts of the harmful waves formed by the emitting unit and to emit counter electromagnetic waves having phase angles at least partially opposite to those of the harmful waves, defining wave characteristics at least partially similar to those of such harmful waves due to the arrangement and, accordingly, countering such harmful waves due to the opposite phase angles in the target space. This counter unit is to be referred to as the "counter unit of the sixth type" or "sixth counter unit" hereinafter.

In another exemplary embodiment of this aspect of the invention, a system may include a main body, at least one emitting unit, and then at least one fifth (or sixth) counter unit. Such an emitting unit may correspond to a cathode ray tube, a light emitting diode, an organic light emitting diode, and/or a plasma display panel and may be arranged to be supported by the body and to emit visible light waves while serving as the base unit for irradiating such harmful waves as electric current flows therein. At least a portion of the emitting unit is also arranged to be exposed through the body for propagating the light waves to an exterior of the body. Accordingly, such a fifth or sixth counter unit may counter the harmful waves by the counter waves.

In another exemplary embodiment of this aspect of the invention, a system may include a main body, at least one emitting unit, and at least one fifth (or sixth) counter unit. The emitting unit includes at least one magnetron and at least one wave guide. The magnetron is arranged to generate therein micro waves, while the wave guide is arranged to guide the micro waves therethrough, where such a magnetron and/or wave guide may be arranged to serve as the base unit for irradiating the harmful waves. Accordingly, such a fifth or sixth counter unit may counter the harmful waves by the counter waves.

In another aspect of the present invention, an exemplary heating system may be fabricated to include at least one base unit irradiating harmful electromagnetic waves and to counter such harmful waves by canceling the harmful waves in a target space and/or suppressing the harmful waves from propagating toward the target space, where the base unit is arranged to include only portions of such a system responsible for irradiating the harmful waves and also affecting paths of the harmful waves therethrough and where the target space is defined between an user and system.

In one exemplary embodiment of this aspect of the invention, a system may have a main body, at least one heating unit, and at least one counter unit. The heating unit is arranged to be supported by the body and to irradiate heat waves (or waves of infrared ray) while serving as the base unit for irradiating the harmful waves when electric current flows therein. Such a heating unit is arranged to include at least one straight resistive wire and/or coiled resistive wire and at least a portion of such a heating unit is arranged to be exposed through the body for propagating the heat waves to an exterior of the body. In one example, the counter unit is arranged to define a shape identical (or similar) to the heating unit, and then to emit counter electromagnetic waves defining phase angles at least partially opposite to those of the harmful waves, having wave characteristics at least partially similar to those of the harmful waves due to the shape and, accordingly, countering such harmful waves due to the opposite phase angles in the target space. Thus counter unit is to be referred to as the "counter unit of the seventh type" or "seventh counter unit" hereinafter. In another example, such a counter unit is arranged to be disposed in an arrangement defined along at least one of multiple wavefronts of such harmful waves formed by the heating unit and to emit counter electromagnetic waves defining phase angles at least partially opposite to those of the harmful waves, having wave characteristics at least partially similar to those of the harmful waves due to the arrangement and, accordingly, countering the harmful waves due to the opposite phase angles in such a target space. Such a counter unit is to be referred to as the "counter unit of the eighth type" or "eighth counter unit" hereinafter.

In another exemplary embodiment of this aspect of the invention, a system may include a main body, at least one heating unit, and then at least one seventh (or eighth) counter unit. The main body is arranged to be formed as an electric blanket, an electric mat (or mattress), an electric heating pad, a hair setter or a hair curler, and to physically contact at least a part of user during use. Such a heating unit is arranged to be retained in the body, to generate heat, and to deliver the heat to the user by heat conduction while serving as the base unit for irradiating such harmful waves as electric current flows therein, where the heating unit is arranged to have at least one straight resistive wire and/or at least one coiled resistive wire. Accordingly, such a seventh or eighth counter unit may counter the harmful waves by the counter waves.

In another exemplary embodiment of this aspect of the invention, a system may include a main body, at least one heating unit, at least one actuator, and at least one seventh (or eighth) counter unit. The main body is arranged to be formed as a hair dryer or a convection heater and to include at least one air pathway with at least one air inlet and at least one air outlet. Such a heating unit is arranged to be disposed along the air pathway and to heat air in the air pathway while serving as the base unit and irradiating such harmful waves when electric current flows therein. The actuator is arranged to fluidly couple with the pathway and to discharge the heated air through the air outlet. Therefore, such a seventh or eighth counter unit may counter the harmful waves by the counter waves.

In another exemplary embodiment of this aspect of the invention, a system may include a main body, at least one heating unit, and then at least one seventh (or eighth) counter unit. The main body is arranged to form an area on which (or a chamber in which) food is to be disposed for cooking. The heating unit is arranged to include at least one straight resistive wire and/or a coiled resistive wire, to be mechanically supported by or on the body, to be exposed through at least a portion of the area (or thermally coupled to at least a portion of the chamber), to generate heat while serving as the base unit and irradiating such harmful waves when electric current flows therein, and to deliver the heat to the food. Accordingly, the seventh or eighth counter unit may counter the harmful waves by the counter waves.

Embodiments of such system aspects of the present invention may include one or more of the following features, and configurational and/or operational variations and/or modifications of the above systems also fall within the scope of the present invention.

At least a portion (or an entire portion) of such a base unit may be exposed through the wave source or the base unit may be disposed inside the wave source, where the base unit may include a conductive wire, sheet, and/or plate of the system.

Such a system may be any electric devices including at least one coil of an electric conductor, where the device including the coil may be an electromagnet, a solenoid, a toroid, a speaker, a motor, a generator, a transformer, and the like. The base unit of such a device may include the coil, an insert made of at least one ferromagnetic material, any parts of the device in which unsteady current flows, any parts of the device across which unsteady voltage applies, and the like.

The system may be any electric devices including at least one speaker capable of converting acoustic sounds into electric and/or optical signals, where examples of such devices may include, but not be limited to earphones, headphones, handsets or main bodies of phones, mobile phones, and the like. Such a speaker may include a cone-drive speaker, electrostatic speaker, piezoelectric speaker, and the like, and the base unit of the speaker may include the coil, a permanent magnet, a piezoelectric unit, an electrode, any parts of the device in which unsteady current flows, any parts of the device in or across which unsteady voltage applies, and the like. The device with the speaker may include at least two identical (or similar, different) speakers enclosed inside a single case member, at least two identical (or similar, different) speakers separately enclosed inside different case members, a pair of earphones, a pair of headphones, an assembly of at least one speaker and at least one microphone, and the like. Such signals may be electrical signals, optical signals, magnetic signals, and the like.

The system may be any electric devices including at least one mechanism which may convert electric and/or optical signals into acoustic sounds, where examples of such devices may include, but not be limited to, microphones, where such signals may be electrical signals, optical signals, magnetic signals, and the like. The system may be any electric devices which may include therein at least one motor for generating mechanical energy from electrical energy. Such a motor may include a DC motor including a stator which is made of a permanent magnet and a rotor which includes an electromagnet, an universal motor including a stator made of an electromagnet and a rotor made of an electromagnet, a synchronous AC motor including a stator which is made of an electromagnet and a rotor made of a permanent magnet, an induction AC motor including a stator which is made of an electromagnet and a rotor made of an electric conductor, a linear motor including a stator made of an electromagnet and a rotor made of a permanent magnet, and the like. Such a base unit may include the rotor, the stator, a permanent magnet, any part of the device along which unsteady current flows, any part of the device across which unsteady voltage applies, and the like. Such a device having the motor may include any kitchen appliances examples of which may include, but not be limited to, a food processor, a mixer, a can opener, an electric grill (or oven, range) having a fan, a dish washer, a refrigerator, a freezer, a cooler, and the like. The device with the motor may be household appliances examples of which may include, but not be limited to, a washer, a dryer, an air conditioner, a dry (or wet) vacuum cleaner, and the like. The device with the motor may be tools including an electric drill, a screwdriver, a nail gun, a stapler, a sander, and so on. The device including such a motor may be personal hygiene appliances including a razor, an electric toothbrush, a hair dryer, and the like.

The system may be any electric devices which may include at least one generator capable of generating electrical energy from mechanical energy. The device with the generator may include an AC generator, a DC generator, an alternator of an automobile, and the like. The base unit of the device may be an electromagnet, a permanent magnet, any parts of the device along which unsteady current flows, any parts of the device across which unsteady voltage applies, and the like.

The system may be any electric devices which may include at least one transformer capable of increasing or decreasing electric voltage from a source. The device with the transformer may be a step-up transformer, a step-down transformer, an adaptor for changing voltage for an electric device, and the like. The base unit of such a device may also include the coil, an insert made of at least one ferromagnetic material, any parts of the device along which unsteady current flows, any parts of the device across which unsteady voltage applies, and the like.

The system may be any electric devices which may include at least one heating unit capable of generating thermal energy from electrical energy. The heating unit may include a straight heating wire, a coiled heating wire, the coiled wire in a shape of the solenoid, the coiled wire in a shape of the toroid, and the like. The base unit of such a device may be the coil, a support which includes at least one ferromagnetic material, any parts of the device in which unsteady current flows, any parts of the device across which unsteady voltage applies, and the like. The device with the heating unit may be any personal heating appliances including an electric heating mattress, an electric heating blanket, an electric heating pad, and the like. The device with the heating unit may be cooking appliances such as an electric grill (or oven, range), a toaster oven, and the like. The device with the heating unit may be hair treating appliances including a hair dryer, a hair setter, a hair curler, a hair steamer, and the like.

Such a system may be any electric devices including at least one light emitting unit. The device with the light emitting unit may include a CRT, a LED, an OLED, a PDP, and the like. The system may be any electric devices including at least one wave emitting units. The device with the wave emitting unit may include a microwave oven, a radar, and the like.

The harmful waves may include carrier-frequency waves having frequencies less than from about 50 Hz to 60 Hz, extremely low-frequency waves of frequencies less than 300 Hz, and the like, and the counter waves may have similar frequencies. Alternatively, the harmful waves may include ultra low-frequency waves defining frequencies less than 3 kHz, very low-frequency waves having frequencies less than 30 kHz, low-frequency waves having frequencies less than 300 kHz, and the like, and the counter waves may have similar frequencies. The target space may be formed on one side of the counter and base units, about a preset angle about the counter unit, between the counter and base units, and the like. When desirable, the harmful waves may define the frequencies greater than 300 kHz, 1 MHz, 10 MHz, 100 MHz, 1 GHz, 10 GHz, 100 GHz, 1 THz, and the like.

The countering may include the above canceling and/or suppressing. Such a counter unit may include an electric conductor along which the current may flow, an electric conductor and/or insulator across which the voltage may be applied, and the like. The counter unit may be disposed side by side with (or with respect to) the base unit, may wind about a preset portion of the base unit, may instead be disposed in a concentric arrangement with respect to the base unit, may be disposed axially with respect to the base unit, and the like. Such a counter unit may be retained by at least one support and maintain its shape or may change a shape thereof while emitting the counter waves. The counter unit may include at least one ferromagnetic insert disposed therethrough.

The shape of the counter unit may be determined based upon whether the counter unit may be arranged to match the shape of the base unit or to match the (shapes of) harmful waves. The shape of the counter unit may be identical to, similar to or different from that of the base unit and/or source. Such a counter unit may define a shape of the wire, strip, sheet, tube, coil, spiral, mesh, mixture of at least one of the shapes, combination thereof, array thereof, and the like. The array may have a shape of a bundle, a braid, a coil, a mesh, and the like. The shape of the counter unit may (or not) conform to that of the base unit and/or source. The counter unit may form the 1-D, 2-D, and/or 3-D analogs of the base units and/or source, may define only one of such analogs of the base units and/or source, may define at least two of the analogs of the base units and/or source, may define only one of the analogs of the base units and/or source, may instead form at least two of the analogs of the base units and/or source, and the like. The analog may be arranged to maintain a similarity with such base units and/or source. The analogs may be arranged to maintain a similarity with such base units and/or source. At least two portions of the counter unit and/or at least two counter units may define the same shape of different sizes, different shapes of similar or different sizes, and the like. The counter unit may have at least substantially uniform shape and/or size along at least a substantial portion thereof along its longitudinal axis, may have the shape and/or size varying along the portion and/or axis, and the like.

The size of the counter unit may (or not) conform to that of the base unit and/or source. Such counter units may be disposed in the arrangement identical to, similar to or different from that of such a base unit and/or source. The counter units may be disposed in an arrangement conforming (or not) to that of the base unit and/or source. The counter units may further be disposed in a symmetric (or asymmetric) arrangement with respect to each other or with respect to the base units and/or source. The counter unit may be aligned with (or misaligned from) the direction of propagation of the harmful waves, the direction of the current and/or voltage, the longitudinal axis of the base unit or source, the short axis of the base unit or source, and the like. All of, only some of, one of or none of the counter units may be aligned with (or misaligned from) at least one of the directions and/or axes. The counter and base units may also be disposed at identical (or similar) distances from the target space. At least a portion of the counter and/or base units may be disposed in another of the units or, alternatively, the counter and base units may be axially disposed along a single common axis of the units, and the like. Such counter units may be disposed angularly around the longitudinal axis of the base unit or source. The counter unit may be movably or stationarily disposed closer (or farther from) such a target space than the base unit (or source). The counter and base units may be disposed on the same side of the target space or, in the alternative, such counter and base units may be disposed on opposite sides of the target space. The counter unit may conform to the base unit (or units) or, in the alternative, such counter units may conform to the base unit (or units), and the like.

The counter unit may be disposed on an exterior, disposed on an interior, and/or embedded in the base unit and/or source. The counter unit may be disposed on, in or inside a case member of the system. Such counter and base units may be made of and/or include at least one common material, may be made of and/or include identical materials, may not include any common material. The counter and base units may be separated from each other by a preset distance, may be mechanically coupled to each other, may form an unitary article, and the like. The counter unit may be directly coupled to the case member, base unit, and/or other parts of the system, may be indirectly coupled thereto through at least one coupler, and the like. The counter unit may be arranged to emit the counter waves with a least amount of material, while consuming a least amount of the current and/or voltage, and the like.

The base unit may be supplied with source current and/or voltage, where the source current or voltage may be supplied to the counter unit as counter current or voltage, where only a portion of the source current or voltage may be supplied to the counter unit as the counter current or voltage, where amplitude and/or direction of at least a portion of the source current or voltage may be altered and supplied to the counter unit as the counter current or voltage, where external current or voltage may be formed, synchronized with the source current or voltage, and supplied to the counter unit as the counter current or voltage, and the like. The counter units may be supplied with identical counter currents or voltages, with different counter currents or voltages, and the like. The counter and base units may also be electrically coupled to each other in a series mode, in a parallel mode or in a hybrid mode or, alternatively, may not be directly coupled to each other. The counter units may be electrically coupled to each other in a series mode, in a parallel mode or in a hybrid mode or, alternatively, may not be directly coupled to each other. All (or only some) of the counter units may electrically couple with the base unit in the same mode or, alternatively, none of the counter units may be electrically coupled to the base unit in the same mode. The counter waves may define amplitudes greater than, similar to or less than those of the harmful waves depending on the disposition thereof with respect to the base unit. The counter and base units may also define substantially identical, similar or different resonance frequencies or, alternatively, may define identical, similar or different resonance frequencies. At least a portion of the counter unit and/or at least one of the counter units may have resonance frequencies different from those of the rest thereof.

Such a system may also include at least one of the magnetic shields described hereinabove or in the co-pending Applications. Such magnetic shields may be disposed in, on, over, around, inside or through at least one of the counter and/or base units. The magnetic shields may define shapes which may at least partially conform to the shapes of the counter and/or base units or, in the alternative, may define shapes which may be at least partially different from shapes of the counter and/or base units. The magnetic shield may have at least one path member with a relative magnetic permeability greater than 1,000, 10,000, 100,000, 1,000,000, and the like. Such a magnetic shield may include at least one magnet member defining at least one South pole. The magnetic shield may include at least one shunt member which may be directly or indirectly coupled to the magnet member. Such a shunt member may have the relative magnetic permeability which may be greater than 1,000, 10,000, 100,000, 1,000,000, and the like. The magnetic shield described hereinabove or disclosed in the co-pending Applications may be incorporated into any of the devices described hereinabove.

The system may include at least one of the electric shields described hereinabove or in the co-pending Applications. Such electric shields described hereinabove and/or disclosed in the co-pending Applications may be included into any of the devices described hereinabove. Such magnetic and/or electric shields may form shapes and/or sizes which may be maintained uniform along the longitudinal axis of the counter and/or base units or which may vary therealong. The shapes and/or sizes of the magnetic and/or electric shields may be identical to, similar to or different from those of such counter and/or base units. The system may include multiple magnetic and/or electric shields. At least two of the magnetic and/or electric shields may shield against the magnetic waves and/or electric waves of the harmful waves with same or different frequencies in the same or different extents. The magnetic and/or electric shields may be disposed over at least a portion (or entire portion) of the counter and/or base units.

In another aspect of the present invention, a method may be provided for countering harmful electromagnetic waves irradiated from at least one base unit of at least one wave source by emitting counter electromagnetic waves, by adjusting shapes of the counter waves, and by at least one of suppressing the harmful waves from propagating to a target space and canceling the harmful waves in the target space, where such a base unit is configured to include only portions of the wave source which are responsible for irradiating the harmful waves and for affecting paths of the harmful waves therethrough and where the target space is defined between the source and an user.

In one exemplary embodiment of this aspect of the invention, a method may include the steps of: providing at least one counter unit (to be referred to as the "first providing" hereinafter); extending the counter unit to be wider than the source; disposing the counter unit between the source and user while aligning its width with at least a portion of a wavefront of the harmful waves; and then emitting by the counter unit the counter waves which are similar to the harmful waves and, thus, countering the harmful waves in the target space. The above extending and disposing may be replaced by the steps of: extending the counter unit to be narrower than the wave source; and disposing the counter unit on an opposite side of the target space with respect to the wave source while aligning its width with at least a portion of a wavefront of the harmful waves.

In another exemplary embodiment of this aspect of the invention, such a method may include the steps of: providing a single counter unit; emitting by the counter unit the counter waves having a first set of multiple wavefronts; identifying a second set of multiple wavefronts of the harmful waves; assessing at least one location along the second set of the wavefronts in which the first set of such wavefronts match the second set thereof in the target space; and disposing the counter unit in such a location, thereby countering the harmful waves with the counter waves in the target space.

In another exemplary embodiment of this aspect of the invention, such a method may include the steps of: providing at least two counter units; emitting from such counter units the counter waves having similar (or identical) phase angles and forming a first set of multiple wavefronts each of which is a sum of at least two wavefronts generated by such at least two counter units; finding a relation between a distance between such counter units and an increase in a radius of curvature of each of the wavefronts of the first set; identifying a second set of multiple wavefronts of the harmful waves; selecting the distance between such counter units in which the first set of the wavefronts match the second set thereof; assessing at least two positions for such counter units in the second set of the wavefronts in which the first set of the wavefronts match the second set thereof; and disposing the counter units in the positions separated by the distance, thereby countering the harmful waves with the counter waves in the target space. The above emitting and finding may be replaced by the steps of: emitting by the counter units the counter waves having at least partially opposite phase angles and defining a first set of multiple wavefronts each representing a sum of at least two wavefronts which are generated by such at least two counter units; and finding a relation between a distance between the counter units and a decrease in a radius of curvature of each of the wavefronts of the first set.

In another aspect of the present invention, a method may be provided for countering harmful electromagnetic waves which are irradiated from at least one base unit of at least one wave source by matching at least one feature of the base unit and then by at least one of suppressing the harmful waves from propagating toward a target space and canceling the harmful waves in the target space. The base unit is configured to include only portions of the wave source responsible for irradiating the harmful waves and also affecting paths of the harmful waves therethrough, where the target space is defined between the source and an user, and where the feature includes a shape, a size, and/or an arrangement.

In one exemplary embodiment of this aspect of the invention, a method may include the steps of: the first providing; configuring the counter unit to match the feature of the base unit; emitting by the counter unit counter electromagnetic waves similar to the harmful waves due to the configuring; and then disposing the counter unit in a location for matching the harmful waves in the target space by the counter waves. The configuring may be replaced by one of the steps of configuring the counter unit to define a configuration which is simpler than that of the base unit while at least minimally maintaining the feature; configuring the counter unit to define a configuration more complex than that of the base unit while at least minimally maintaining the feature; configuring the counter unit to define a dimension which is defined by a less number of unit axes than the base unit while at least minimally maintaining the feature; and configuring the counter unit to have a dimension defined by a greater number of unit axes than that of the base unit while at least minimally maintaining the feature.

In another exemplary embodiment of this aspect of the invention, such a method may include the steps of: providing a single counter unit; configuring the counter unit to have a configuration which is simpler than that of a single base unit while maintaining the feature; emitting by such a counter unit counter electromagnetic waves similar to the harmful waves due to the configuring; and disposing the counter unit in a location for matching such harmful waves in the target space by the counter waves, thereby countering the harmful waves by the counter waves therein. The above configuring may be replaced by one of the steps of configuring the counter unit to define a configuration which is similar (or identical) to an arrangement of multiple base units while maintaining the feature; configuring such a counter unit to have a dimension formed by less mutually orthogonal unit axes than an arrangement of multiple base units while maintaining the feature; and configuring the counter unit to have a dimension which is formed by more mutually orthogonal unit axes than a dimension of multiple base units while maintaining the feature.

In another exemplary embodiment of this aspect of the invention, such a method may include the steps of: providing multiple counter units; arranging at least two of the above counter units in a configuration which is simpler than that of a single base unit while maintaining the feature; emitting by the counter units counter electromagnetic waves similar to the harmful waves due to the configuring; and disposing the counter units in locations for matching the harmful waves in the target space by the counter waves, thereby countering the harmful waves by the counter waves therein. The arranging may be replaced by one of the steps of: arranging at least two of the counter units in a configuration which is similar or identical to an arrangement of multiple base units while maintaining such a feature; arranging such counter units in an arrangement defining a dimension which is formed by less mutually orthogonal unit axes than another dimension of a single base unit while maintaining such a feature; and arranging the counter units in an arrangement with a dimension which is formed by more mutually orthogonal unit axes than a dimension of multiple base units while maintaining the feature;

In another exemplary embodiment of this aspect of the invention, such a method may include the steps of: providing a smaller number of such counter units for a greater number of the base units; arranging the counter units while approximating an arrangement of the base units and maintaining the feature; emitting by the counter units counter electromagnetic waves which are similar to the harmful waves due to the disposing; and then disposing the counter unit in a location for matching the harmful waves in the target space by the counter waves, thereby countering such harmful waves with such counter waves therein. Such providing and arranging may be replaced by the steps of providing a greater number of the counter units for a smaller number of the base units; and arranging the counter units while disposing at least two of the counter units around at least one of the base units and while maintaining the feature.

In another exemplary embodiment of this aspect of the invention, such a method may have the steps of the first providing; configuring the counter unit to move with respect to the base unit; emitting by the counter unit counter electromagnetic waves; finding a relationship between a distance from the counter unit to the base unit and an extent (or degree) of matching between the counter and harmful waves; assessing a location in which the counter waves best match the harmful waves; and moving the counter unit to the location for best matching the harmful waves in the target space by the counter waves, thereby countering the harmful waves by the counter waves therein.

In another aspect of the present invention, a method may be provided for countering harmful electromagnetic waves irradiated from at least one base unit of at least one wave source by matching the harmful waves and by at least one of suppressing the harmful waves from propagating to a target space and canceling the harmful waves in the target space. Such a base unit is configured to include only portions of the wave source responsible for irradiating such harmful waves and affecting paths thereof therethrough, and the target space is defined between the source and an user.

In one exemplary embodiment of this aspect of the invention, a method may include the steps of: identifying a first set of multiple wavefronts of the harmful waves; disposing at least one counter unit along at least one of such wavefronts; and emitting by the counter unit counter electromagnetic waves forming a second set of multiple wavefronts which are similar (or identical) to the first set of the wavefronts in the target space due to the disposing, thereby countering the harmful waves by the counter waves therein.

In another exemplary embodiment of this aspect of the invention, such a method may have the steps of: identifying multiple wavefronts of the harmful waves; providing at least one counter unit for emitting counter electromagnetic waves which define multiple wavefronts similar to a shape and/or an arrangement of the counter unit; disposing the counter unit along at least one of the wavefronts of the harmful waves; and then emitting the counter waves while aligning their wavefronts with those of the harmful waves in the target space due to the providing and disposing, thereby countering the harmful waves with the counter waves therein. The above providing and disposing may also be replaced by the steps of: providing at least one counter unit for emitting counter electromagnetic waves defining multiple wavefronts different from a shape and/or an arrangement of the counter unit; and disposing the counter unit across (or along) at least two of the wavefronts of the harmful waves based on the providing.

In another exemplary embodiment of this aspect of the invention, such a method may have the steps of: identifying multiple wavefronts of the harmful waves; disposing multiple counter units in an arrangement which is defined along at least one of such wavefronts; configuring the counter units to emit counter electromagnetic waves which define multiple wavefronts similar to the arrangement of the counter units; and emitting the counter waves while aligning their wavefronts with those of such harmful waves in the target space due to the configuring, thereby countering the harmful waves with the counter waves therein. The above disposing and configuring may also be replaced by the steps of: disposing multiple counter units in an arrangement across or along at least two of the wavefronts; and configuring the counter units to emit counter electromagnetic waves defining multiple wavefronts different from the arrangement of the counter units.

In another exemplary embodiment of this aspect of the invention, a method may have the steps of: the first providing; identifying multiple wavefronts of the harmful waves; emitting by such a counter unit counter electromagnetic waves having multiple wavefronts; locating the counter unit between the base unit and target space; comparing shorter radii of curvature of the wavefronts of such counter waves to longer radii of curvature of the harmful waves; and disposing the counter unit into a location in which the radii of curvature of such counter and harmful waves are configured to best match each other in the target space, thereby countering the harmful waves by the counter waves therein. Such locating and comparing may be replaced by the steps of: locating the counter unit on an opposite side of the target space with respect to the base unit; and then comparing longer radii of curvature of the wavefronts of the counter waves to shorter radii of curvature of the harmful waves.

In another exemplary embodiment of this aspect of the invention, such a method may have the steps of: the first providing; configuring the counter unit to move with respect to the base unit; emitting by the counter unit counter electromagnetic waves; finding a relationship between a distance from the counter unit to the base unit and an extend (or degree) of matching between radii of curvature of the counter waves and those of the harmful waves; assessing a location where the counter waves best match the harmful waves; and moving the counter unit to the location for matching the harmful waves in such a target space by the counter waves, thereby countering the harmful waves by the counter waves therein.

In another aspect of the present invention, a method may be provided for countering harmful electromagnetic waves irradiated from at least one base unit of at least one wave source by emitting counter electromagnetic waves by at least one counter unit and by propagating the counter waves in a preset direction toward the harmful waves. The base unit is configured to include only portions of the source responsible for irradiating the harmful waves and for affecting paths of the harmful waves therethrough, while the target space is defined between the wave source and an user.

In one exemplary embodiment of this aspect of the invention, a method may include the steps of: configuring the counter waves to define shapes similar to those of the harmful waves and at least partially opposite phase angles (will be referred to as the "first configuring" hereinafter); enclosing at least a portion of the base unit by the counter unit; and emitting the counter waves while enclosing the harmful waves in such a target space, thereby countering the harmful waves by the counter waves therein. The above enclosing may be replaced by the step of: disposing multiple counter units around at least a portion of the base unit.

In another exemplary embodiment of this aspect of the invention, such a method may have the steps of: the first configuring; disposing at least a portion of the counter unit inside the base unit; and emitting the counter waves while being enclosed by the harmful waves in the target space, thereby countering the harmful waves by the counter waves therein. The above disposing may be replaced by the step of: enclosing at least a portion of the counter unit by multiple base unit.

In another exemplary embodiment of this aspect of the invention, such a method may have the steps of: the first configuring; disposing the counter unit lateral to the base unit; and then emitting the counter waves to the target space with the harmful waves, thereby countering the harmful waves by the counter waves therein. The above disposing may be replaced by one of the steps of: disposing the counter unit along a longitudinal axis of the base unit and away therefrom; and enclosing at least a portion of one of the counter and base units by another of the units.

In another exemplary embodiment of this aspect of the invention, such a method may have the steps of: the first configuring; aligning the counter unit with a direction of propagation of such harmful waves; and emitting the counter waves toward the target space with such harmful waves, thereby countering the harmful waves by the counter waves therein. The above aligning may be replaced by one of the steps of: aligning the counter unit with a direction of electric current and/or voltage applied to the base unit; aligning the counter unit with a longitudinal axis of the base unit; aligning the counter unit with a short axis of the base unit, and the like.

In another exemplary embodiment of this aspect of the invention, such a method may include the steps of: the first configuring; disposing the counter unit between the base unit and target space; emitting by the counter unit the counter waves with amplitudes less than those of the harmful waves; and propagating the counter waves toward the target space along with the harmful waves, thereby countering the harmful waves by the counter waves therein. The above disposing and emitting may be replaced by the steps of: disposing the counter unit on an opposite side of the target space relative to the base unit; and emitting by the counter unit the counter waves defining amplitudes greater than those of the harmful waves.

In another exemplary embodiment of this aspect of the invention, such a method may have the steps of: the first configuring; disposing the counter unit between the base unit and the target space; extending the counter unit to have a width greater than that of the base unit in a direction normal to a direction of propagation of the harmful waves; and then emitting the counter waves toward the target space with the harmful waves, thereby countering the harmful waves by the counter waves therein. The above disposing and extending may be replaced by the steps of: disposing the counter unit on an opposite side of the target space relative to the base unit; and extending the counter unit to a width less than that of the base unit in a direction normal to a direction of propagation of the harmful waves.

In another aspect of the present invention, a method may be provided for countering harmful electromagnetic waves irradiated from at least one base unit of at least one wave source by emitting counter electromagnetic waves and by at least one of canceling the harmful waves with the counter waves in a target space and suppressing the harmful waves from propagating to the target space by the counter waves. The base unit is configured to include only portions of the source responsible for irradiating the harmful waves and also affecting paths thereof therethrough, while the target space is defined between the wave source and an user.

In one exemplary embodiment of this aspect of the invention, a method may include the steps of: providing a single counter unit emitting the counter waves; the first configuring; and countering the harmful waves irradiated by a single base unit by the counter waves.

In another exemplary embodiment of this aspect of the invention, such a method may have the steps of: providing a single counter unit which emits such counter waves; the first configuring; and countering a sum of the harmful waves irradiated by all of multiple base units with the counter waves. The above countering may be replaced by the step of: countering the harmful waves irradiated by at least one but not all of multiple base units by the counter waves.

In another exemplary embodiment of this aspect of the invention, such a method may have the steps of: providing multiple counter units emitting such counter waves; the first configuring; and then countering the harmful waves irradiated from a single base unit by a sum of all of the counter waves emitted by all of the counter units.

In another exemplary embodiment of this aspect of the invention, such a method may have the steps of: providing multiple counter units emitting such counter waves; the first configuring; and then countering a sum of the harmful waves irradiated by all of multiple base units with another sum of the counter waves emitted by at least two of the counter units. The above countering may be replaced by the step of: countering the harmful waves irradiated by at least one but not all of multiple base units by another sum of the counter waves emitted by at least two of the counter units.

In another exemplary embodiment of this aspect of the invention, such a method may have the steps of: providing at least two counter units each emitting a set of the counter waves; configuring at least one of the counter units to move with respect to another thereof; the first configuring; and then moving such at least one of the counter units with respect to such a base unit in the emitting, thereby countering the harmful waves irradiated from a single base unit with a different number of the sets of the counter waves.

In another aspect of the present invention, a method may be provided for countering harmful electromagnetic waves which are irradiated from at least one wave source which is shaped into at least one curvilinear wire by emitting counter electromagnetic waves.

In one exemplary embodiment of this aspect of the invention, a method may include the steps of: the first providing; shaping the counter unit as one of a wire, a strip, and a sheet; disposing such a counter unit along and close to the wire; and supplying electric current in the wave source of the wire and the counter unit in opposite directions while emitting such counter waves from the counter unit for countering the harmful waves by the counter waves (which will be referred to as the "first supplying" hereinafter). The above disposing may be replaced by the step of: braiding the counter unit around and close to the wire.

In another exemplary embodiment of this aspect of the invention, such a method may have the steps of: providing multiple counter units each shaped as a wire, a strip, and/or a sheet; disposing the counter units around and close to the wire; and the first supplying. Such disposing may be replaced by the step of: braiding each of the counter units around and close to the wire in the same or different directions.

In another exemplary embodiment of this aspect of the invention, such a method may have the steps of: the first providing; shaping the counter unit as at least one coil or spiral; winding the counter unit around the wire; and the first supplying. The above shaping and winding may be replaced by the steps of: shaping the counter unit into a sheet or a mesh; and winding such a counter unit around the wire. The above shaping and winding may also be replaced by the steps of: shaping the counter unit into an annular tube with a lumen; and disposing the wire inside the lumen of the counter unit.

In another exemplary embodiment of this aspect of the invention, such a method may have the steps of: identifying multiple wavefronts of the harmful waves formed around the wire; disposing at least one counter unit along at least one of the above wavefronts; and emitting by the counter unit the counter waves of multiple wavefronts which are similar (or identical) to the wavefronts of the wire, thereby countering the harmful waves with the counter waves.

In another aspect of the present invention, a method may be provided for countering harmful electromagnetic waves which are irradiated from at least one wave source shaped into at least one curvilinear strip (or sheet) by emitting counter electromagnetic waves.

In one exemplary embodiment of this aspect of the invention, a method may include the steps of: the first providing; shaping the counter unit as a wire, a strip or a sheet; disposing the counter unit along and close to the strip (or sheet); and supplying electric current in the wave source of the strip (or sheet) and the counter unit in opposite directions while emitting the counter waves by the counter unit in order to counter such harmful waves by the counter waves (to be referred to as the "second supplying" hereinafter). Such disposing may also be replaced by the step of: braiding the counter unit around and close to the strip (or sheet).

In another exemplary embodiment of this aspect of the invention, such a method may have the steps of: providing multiple counter units each shaped as a wire, a strip or a sheet; disposing such a counter units around and close to the strip (or sheet); and the second supplying. Such disposing may be replaced by the step of: braiding each of the counter units around and close to the strip (or sheet) in one of same and different directions.

In another exemplary embodiment of this aspect of the invention, such a method may have the steps of: the first providing; shaping the counter unit as one of at least one coil and at least one spiral; winding the counter unit around the strip (or sheet); and then the second supplying. The shaping and winding may be replaced by the steps of: shaping the counter unit as a sheet or a mesh; and winding the counter unit around the strip (or sheet). The above shaping and winding may also be replaced by the steps of: shaping the counter unit as a pair of strips (or sheets); and disposing the wire between the strips (or sheets).

In another exemplary embodiment of this aspect of the invention, such a method may have the steps of: identifying multiple wavefronts of the harmful waves around the strip (or sheet); disposing at least one counter unit along at least one of the wavefronts; and emitting from the counter unit such counter waves with multiple wavefronts similar (or identical) to the wavefronts of the strip (or sheet), thereby countering the harmful waves with the counter waves.

In another aspect of the present invention, a method may be provided for countering harmful electromagnetic waves which are irradiated from at least one wave source shaped as at least one curvilinear tube with a lumen by emitting counter electromagnetic waves.

In one exemplary embodiment of this aspect of the invention, a method may include the steps of: the first providing; shaping the counter unit as a wire, a strip or a sheet; disposing the counter unit along and close to the tube; and supplying electric current in the wave source of the tube and counter unit along opposite directions while emitting the counter waves by the counter unit for countering the harmful waves by the counter waves (which will be referred to as the "third supplying" hereinafter). Such disposing may be replaced by the step of: braiding the counter unit around and close to the tube In another exemplary embodiment of this aspect of the invention, such a method may have the steps of: providing multiple counter units each shaped as a wire, strip or sheet; disposing the counter units around and dose to the tube; and the third supplying. The above disposing may be replaced by the step of: braiding each counter unit around and close to the tube in the same or different directions.

In another exemplary embodiment of this aspect of the invention, a method may have the steps of: the first providing; shaping the counter unit as at least one wire or strip; disposing the counter unit inside the lumen of the tube; and the third supplying.

In another exemplary embodiment of this aspect of the invention, such a method may have the steps of the first providing; shaping the counter unit as at least one coil or spiral; winding the counter unit around the tube; and the third supplying. The above shaping and winding may be replaced by the steps of shaping the counter unit into one of a sheet and a mesh and then winding the counter unit around the tube; shaping the counter unit into a bigger tube with a lumen and then disposing the tube inside the lumen of the counter unit; and shaping the counter unit into a smaller tube with a lumen and then disposing the counter unit inside the lumen of the tube.

In another exemplary embodiment of this aspect of the invention, such a method may have the steps of: identifying multiple wavefronts of the harmful waves formed around the tube; disposing at least one counter unit along at least one of the wavefronts; and then emitting by the counter unit the counter waves having multiple wavefronts similar (or identical) to the wavefronts of the tube, thereby countering the harmful waves with the counter waves.

In another aspect of the present invention, a method may be provided for countering harmful electromagnetic waves which are irradiated from at least one wave source shaped into at least one curvilinear coil by emitting counter electromagnetic waves.

In one exemplary embodiment of this aspect of the invention, a method may include the steps of the first providing; shaping the counter unit into a toroid by disposing opposing ends of such a coil adjacent to each other; supplying electric current in the coil; and supplying electric current in the wave source of the coil and the counter unit in opposite directions while emitting the counter waves by the counter unit for countering the harmful waves by the counter waves (to be referred to as the "fourth supplying" hereinafter).

In another exemplary embodiment of this aspect of the invention, such a method may have the steps of: the first providing; shaping the counter unit as a wire, a strip or a spiral smaller than the coil of the base unit; winding such a coil of the base unit around the counter unit; and the fourth supplying. The above shaping and winding may be replaced by the steps of shaping the counter unit as another coil smaller than the coil of the base unit; and winding the coil of the base unit around the counter unit.

In another exemplary embodiment of this aspect of the invention, a method may include the steps of: the first providing; shaping the counter unit as another coil; disposing the coils of the counter and base units adjacent to each other; and the fourth supplying. Such disposing may be replaced by the step of: braiding the coils of the counter and base units.

In another exemplary embodiment of this aspect of the invention, such a method may have the steps of identifying multiple wavefronts of the harmful waves formed around such a coil; disposing at least one counter unit along at least one of the wavefronts; and then emitting by the counter unit such counter waves having multiple wavefronts similar (or identical) to the wavefronts of the tube, thereby countering the harmful waves with the counter waves.

Embodiments of such method aspects of the present invention may include one or more of the following features, and configurational and/or operational variations and/or modifications of the above methods also fall within the scope of the present invention.

Such countering may include the step of: countering the harmful waves but preserving audible sound waves. The countering may include at least one of the steps of: suppressing at least a portion of the harmful waves from propagating toward the target space by the counter waves; canceling the portion of the harmful waves by the counter waves in the target space, and the like. The countering may also include at least one of the steps of: countering the harmful waves of frequencies less than about 50 Hz to 60 Hz; countering the harmful waves defining frequencies less than about 300 Hz; and countering the harmful waves of frequencies less than about 1 kHz. The countering may also include at least one of the steps of: countering such harmful waves with frequencies less than about 10 kHz; countering the harmful waves of frequencies less than about 100 kHz; countering the harmful waves with frequencies less than about 1 MHz, 10 MHz, 100 MHz, 1 GHz, 10 GHz, 100 GHz, 1 THz, and the like. The countering may include at least one of the steps of: countering the harmful waves in only a portion of a preset frequency range while preserving the rest thereof; countering magnetic waves of the harmful waves; countering an entire portion of the harmful waves, and the like.

The affecting may include at least one of the steps of: including a permanent magnet; applying the electric voltage; flowing the electric current, and the like. Such extending may include one of the steps of: lengthening the counter unit along its length; widening the counter unit along its width, and the like. The providing may include at least one of the steps of: forming the counter unit into a shape of at least one of a wire, a strip, a sheet, a tube, a coil, a spiral, and a mesh; forming the counter unit into one of a mixture of the shapes, a combination of the shapes, and an array of the shapes, and the like. The forming may include at least one of the steps of: enclosing at least a portion of such a base unit by an array (or bundle) of multiple wires of the counter unit; enclosing the portion of the base unit by an array (or bundle) of multiple strips of the counter unit; enclosing the portion of the base unit by an array (or bundle) of multiple sheets of the counter unit; enclosing the portion of the base unit by an array (or bundle) of multiple tubes of the counter unit; winding with at least one coil of the counter unit about the portion of the base unit; winding the portion of the base unit with an array (or a bundle) of multiple coils; and enclosing the portion of the base unit with at least one annular mesh of the counter unit. Such forming the counter unit may further include at least one of the steps of: extending a single wire for at least a portion of the counter unit; extending an array (or bundle) of multiple wires for the portion; extending a single strip for the portion; extending an array (or bundle) of multiple strips for the portion; extending a single sheet for the portion; extending an array (or bundle) of multiple sheets for the portion; extending a single tube therefor; extending a bundle (or array) of multiple tubes therefor; winding a single coil therefor; winding a bundle (or array) of multiple coils therefor; extending a single annular mesh therefor; and extending an array (or bundle) of multiple annular meshes therefor.

The providing may include one of the steps of: exposing the counter unit through the base unit; hiding the counter unit under (or inside) the base unit, and the like. The providing may include at least one of the steps of: fixedly disposing the counter unit; movably disposing the counter unit, and so on. The providing may include one of the steps of: forming the base and counter units of a same material; forming the base and counter units of different materials; including at least one but not all of materials in the base and counter units, and the like. The providing may include one of the steps of: arranging the base and counter units to have similar (or identical) resonance frequencies; arranging the base and counter units to define different resonance frequencies, and the like.

The disposing may include at least one of the steps of: disposing the counter unit laterally (or side by side) with the base unit; enclosing at least one of the counter and base units with another of the units; axially aligning the base and counter units, and the like. Such enclosing may include one of the steps of: disposing the counter unit indirectly over (or around) the base unit (or source); disposing the counter unit directly on (or around) the base unit (or source), and the like. The enclosing may also include at least one of the steps of: arranging at least two of the counter units concentrically; coupling the counter units electrically in one of a series mode, a parallel mode, and a hybrid mode, and the like. The aligning may include one of the steps of: aligning the counter unit with the longitudinal axis of the base unit; aligning the counter unit with the short axis of the base unit; aligning the counter unit in the direction of the current flowing in (or voltage applied across) the base unit, aligning the counter unit with the direction of propagation of the harmful waves, and the like.

The configuring the counter unit may include at least one of the steps of controlling a shape of the counter unit; controlling a size of the counter unit; controlling an arrangement of the counter unit, and the like. The disposing may include at least one of the steps of: controlling an orientation of such a counter unit with respect to the base unit (or target space); controlling an alignment of the counter unit with respect thereto; controlling a first distance between the counter unit and base unit (or target space); controlling a second distance between the counter units, and the like.

The emitting may have one of the steps of: controlling the phase angles of the counter waves to be at least similar to those of the harmful waves when the counter and harmful waves propagate along at least partially opposite directions; controlling the phase angles of the counter waves to be at least opposite to those of the harmful waves when the counter and harmful waves propagate along at least similar directions; and controlling the phase angles of the counter waves to be transverse to those of the harmful waves when the counter and harmful waves propagate in directions transverse to each other. Such emitting may include at least one of the steps of: manipulating amplitudes of the counter waves to be greater (or less) than those of the harmful waves when measured in the target space; manipulating the amplitudes of the counter waves to be similar (or identical) to those of the harmful waves when measured at the base unit, and the like. The emitting may include at least one of the steps of: propagating the counter waves in the same direction as the harmful waves; propagating the counter waves in a direction different from that of the harmful waves irradiated by each of such base units but in the same direction as that of a sum of the harmful waves from the base units, and the like. The emitting may include the step of: manipulating phase angles of the counter waves to be at least partially (or substantially) opposite to those of the harmful waves.

The method may also include one of the steps of: flowing the current in an entire portion of the base unit; flowing the current in only a portion of the base unit; applying such voltage across an entire portion of the base unit; and applying such voltage across only a portion of the base unit. The method may include one of the steps of: flowing the current in a single direction through the base (or counter) unit; flowing such current along different directions in different portions of the base (or counter) unit; applying such voltage in a single direction through the base (or counter) unit; applying such voltage in different directions along different portions of the base (or counter) unit, and the like. The method may include the step of: providing multiple base units for the harmful waves, and the flowing may include one of the steps of flowing the currents with the same amplitudes along a same direction in all of the base (or counter) units; flowing the currents of the same amplitudes in different directions along the base (or counter) units; flowing the currents of different amplitudes in the same direction in all of the base (or counter) units; flowing the currents of different amplitudes in different directions in the base (or counter) units, and the like. The method may include the step of: providing multiple base units for the harmful waves, and the applying may include one of the steps of: applying the voltages with the same amplitudes along a same direction in all of the base (or counter) units; applying the voltages of the same amplitudes in different directions along the base (or counter) units; applying the voltages of different amplitudes in the same direction in all of the base (or counter) units; applying the voltages of different amplitudes in different directions in the base (or counter) units, and the like.

Such flowings may include one of the steps of: flowing the currents of the same (or different) amplitudes in the counter unit; flowing in the counter unit another current which may not be derived from the current supplied to the base unit but may have a temporal pattern at least partially similar to that of the current supplied to the base unit; flowing along the counter unit another current which may be derived not from the current to the base unit and may have a temporal pattern different from that of the current to the base unit, and the like. Such flowing the currents may include one of the steps of: flowing such currents in the base unit and then in the counter unit; flowing the currents in the counter unit and then in the base unit; flowing such currents at least simultaneously in the base and counter units, and the like.

In another aspect of the present invention, a system may be provided for countering harmful electromagnetic waves irradiated from at least one base unit of at least one wave source by emitting counter electromagnetic waves, by controlling a shape of such a counter unit, and by at least one of suppressing the harmful waves from propagating toward a target space by the counter waves and canceling the harmful waves in the target space by the counter waves, where such a base unit is configured to include only portions of the source responsible for irradiating the harmful waves and for affecting paths of the harmful waves therethrough and where the target space is defined between the system and an use.

In one exemplary embodiment of this aspect of the invention, such a system may be made by a process including the steps of arranging at least one counter unit to have a width longer than that of the base unit; disposing the counter unit between the wave source and user while aligning its width with at least a portion of a wavefront of the harmful waves; configuring the counter unit to emit such counter waves defining wave characteristics similar to the harmful waves but having at least partially opposite phase angles thereto; and aligning the counter unit to propagate the counter waves toward the target space, thereby countering the harmful waves by the counter waves therein (to be referred to as the "first aligning" hereinafter). Such arranging and disposing may be replaced by the steps of: arranging at least one counter unit to define a width narrower than the base unit; and disposing the counter unit on an opposite side of the target space with respect to the wave source while aligning its width with at least a portion of a wavefront of the harmful waves.

In another exemplary embodiment of this aspect of the invention, a system may be made by a process including the steps of identifying multiple wavefronts of the harmful waves; configuring a single counter unit to emit the counter waves defining multiple wavefronts which have phase angles at least partially opposite to those of the harmful waves and which are also capable of matching the wavefronts of the harmful waves when disposed at a preset distance from the base unit; disposing the counter unit in the distance from the base unit; and the first aligning.

In another exemplary embodiment of this aspect of the invention, a system may be made by a process including the steps of: providing at least two counter units; configuring such counter units to emit the counter waves which define similar (or identical) phase angles and have a first set of multiple wavefronts each corresponding to a sum of at least two wavefronts generated by the counter units; finding a relationship between a distance between such counter units and an increase in a radius of curvature of each of the wavefronts of the first set; identifying a second set of multiple wavefronts of the harmful waves; configuring the counter units to match the radii of curvature of the wavefronts of the first set with those of the wavefronts of the second set when disposed at preset distances from the base unit; disposing the counter units in the distances; and then the first aligning. The above configuring and finding may also be replaced by the steps of: configuring the counter units to emit the counter waves defining at least partially opposite phase angles and a first set of multiple wavefronts each corresponding to a sum of at least two wavefronts generated by the counter units; and finding a relationship between a distance between the counter units and a decrease in a radius of curvature of each of the wavefronts of the first set.

In another aspect of the present invention, a system may be provided for countering harmful electromagnetic waves irradiated from at least one base unit of at least one wave source by emitting counter electromagnetic waves, by matching at least one feature of the base unit thereby, and by at least one of canceling the harmful waves with the counter waves in a target space and suppressing the harmful waves from propagating toward the target space by such counter waves, where such a base unit is configured to include only portions of the source which are responsible for irradiating the harmful waves and for affecting paths of the harmful waves therethrough, while the target space is defined between the system and an user.

In one exemplary embodiment of this aspect of the invention, such a system may be made by a process including the steps of: arranging at least one counter unit to match such a feature of the base unit; configuring the counter unit to emit the counter waves similar (or identical) to the harmful waves due to the arranging but having phase angles at least partially opposite to those of the harmful waves (to be referred to as the "second countering" hereinafter); and the first aligning. The above arranging may be replaced by one of the steps of: arranging at least one counter unit to define a configuration simpler than that of the base unit while at least minimally maintaining the feature; arranging at least one counter unit to define a configuration more complex than that of the base unit while at least minimally maintaining such a feature; arranging at least one counter unit to have a dimension defined by a less number of unit axes than the base unit while at least minimally maintaining the feature; and arranging at least one counter unit to have a dimension which is defined by a greater number of unit axes than that of the base unit while at least minimally maintaining the feature.

In another exemplary embodiment of this aspect of the invention, a system may be made by a process including the steps of: arranging a single counter unit to define a configuration simpler than that of a single base unit while maintaining the feature; the second countering; and the first aligning. The above arranging may be replaced by one of the steps of: arranging a single counter unit to define a configuration similar (or identical) to an arrangement of multiple base units while maintaining such a feature; arranging a single counter unit to define a dimension formed by less mutually orthogonal unit axes than an arrangement of multiple base units while maintaining the feature; and arranging a single counter unit to define a dimension formed by more mutually orthogonal unit axes than a dimension of multiple base units while maintaining the feature.

In another exemplary embodiment of this aspect of the invention, a system may be made by a process including the steps of: providing multiple counter units; arranging at least two of the counter units in a configuration simpler than that of a single base unit while maintaining the feature; configuring the counter units to emit the counter waves similar to (or identical to) the harmful waves due to such arranging but to defining phase angles at least partially opposite to those of such harmful waves; and aligning the counter units to propagate the counter waves to the target space, thereby countering the harmful waves by the counter waves therein. The above arranging may also be replaced by one of the steps of: arranging at least two of the counter units in a configuration which is similar (or identical) to an arrangement of multiple base units while maintaining such a feature; arranging the counter units in an arrangement defining a dimension which is formed by less mutually orthogonal unit axes than a dimension of a single base unit while maintaining such a feature; and arranging the counter units in an arrangement defining a dimension formed by more mutually orthogonal unit axes than a dimension of multiple base units while maintaining the feature.

In another exemplary embodiment of this aspect of the invention, a system may be made by a process including the steps of: providing less counter units than such base units; approximating an arrangement of the base units by the counter units while maintaining such a feature; configuring such counter units to emit the counter waves which are similar to (or identical to) the harmful waves due to the approximating but define phase angles at least partially opposite to those of the harmful waves; and aligning the counter units to propagate the counter waves to the target space, thereby countering the harmful waves by the counter waves therein. The above providing and approximating may also be replaced by the steps of: providing more counter units for less base units; and approximating an arrangement of the base units by the counter units while disposing at least two of the counter units around at least one of the base units and maintaining the feature.

In another exemplary embodiment of this aspect of the invention, a system may be made by a process including the steps of: arranging at least one counter unit to move with respect to the base unit; configuring the counter unit to emit the counter waves similar (or identical) to the harmful waves but defining phase angles at least partially opposite to those of the harmful waves; finding a relation between a distance from the counter unit to the base units and an extent of matching between such counter and harmful waves; and then moving the counter unit a location where the extent attains its maximum, thereby countering the harmful waves by the counter waves in the target space.

In another aspect of the present invention, a system may be provided for countering harmful electromagnetic waves irradiated from at least one base unit of at least one wave source by emitting counter electromagnetic waves and then matching the harmful waves thereby, and by at least one of canceling the harmful waves with the counter waves in a target space and suppressing the harmful waves from propagating to the target space by the counter waves. Such a base unit is configured to include only portions of the source responsible for irradiating the harmful waves and for affecting their paths therethrough, while the target space is defined between the system and an user thereof.

In one exemplary embodiment of this aspect of the invention, such a system may be made by a process including the steps of: identifying a first set of multiple wavefronts of such harmful waves; disposing at least one counter unit along at least one of the wavefronts; configuring the counter unit to emit the counter waves forming a second set of multiple wavefronts similar to (or identical to) the first set of the wavefronts in the target space due to the disposing; and the first aligning.

In another exemplary embodiment of this aspect of the invention, a system may be made by a process including the steps of: identifying multiple wavefronts of such harmful waves; configuring at least one counter unit to emit the counter waves defining multiple wavefronts similar to a shape and/or an arrangement of the counter unit; disposing the counter unit along at least one of the wavefronts of the harmful waves; and arranging the counter unit to emit such counter waves of which wavefronts are aligned with those of the harmful waves in the target space based upon the configuring, thereby countering the harmful waves by the counter waves therein. The above configuring and disposing may be replaced by the steps of: configuring at least one counter unit to emit the counter waves with multiple wavefronts different from at least one of a shape and an arrangement of the counter unit; and disposing such a counter unit across (or along) at least two of the wavefronts of the harmful waves based on the configuring.

In another exemplary embodiment of this aspect of the invention, such a system may be made by a process including the steps of: identifying multiple wavefronts of the harmful waves; disposing multiple counter units in an arrangement along at least one of the wavefronts; configuring the counter units to emit such counter waves with multiple wavefronts similar to the arrangement of the counter units; and arranging the counter units to emit such counter waves of which wavefronts are aligned with those of the harmful waves in the target space based on the configuring, thereby countering the harmful waves by the counter waves therein. The above disposing and configuring may be replaced by the steps of disposing multiple counter units in an arrangement across (or along) at least two of the wavefronts; and configuring the counter units to emit the counter waves with multiple wavefronts different from the arrangement of the counter units.

In another exemplary embodiment of this aspect of the invention, a system may be made by a process including the steps of: identifying multiple wavefronts of such harmful waves; configuring at least one counter unit to emit such counter waves with multiple wavefronts each defining a radius of curvature; locating the counter unit between the base unit and target space; comparing shorter radii of curvature of the wavefronts of such counter waves with longer radii of curvature of the harmful waves; and configuring the counter unit to be disposed in a location where the radii of curvature of the wavefronts of the counter waves are configured to match those of the wavefronts of the harmful waves in the target space, thereby countering the harmful waves by the counter waves therein. The above locating and comparing may further be replaced by the steps of: locating the counter unit on an opposite side of the target space relative to the base unit; and comparing longer radii of curvature of the wavefronts of the counter waves to shorter radii of curvature of the harmful waves.

In another exemplary embodiment of this aspect of the invention, a system may be made by a process including the steps of: arranging at least one counter unit to move with respect to the base unit; configuring the counter unit to emit the counter waves similar (or identical) to the harmful waves but have phase angles at least partially opposite to those of the harmful waves; finding a relationship between a distance between the counter and base units and matching between radii of curvature of the counter waves and those of the harmful waves; assessing a location in which the wavefronts of the counter and harmful waves best match each other, and moving the counter unit to the location for best matching the harmful waves in the target space by such counter waves, thereby countering the harmful waves by the counter waves therein.

In another aspect of the present invention, a system may be provided for countering harmful electromagnetic waves irradiated by a base unit of at least one wave source through at least one of canceling the harmful waves in a target space and suppressing the harmful waves from propagating toward the target space, where such a base unit is configured to include only portions of the wave source which are responsible for irradiating the harmful waves and for affecting paths of the harmful waves therethrough and where the target space is defined between the system and an user.

In one exemplary embodiment of this aspect of the invention, such a system may be made by a process including the steps of: arranging at least one counter unit to have a shape which is identical (or similar) to the base unit and to emit counter electromagnetic waves, and configuring such counter waves to have phase angles at least partially opposite to those of the harmful waves, to define wave characteristics at least partially similar to those of the harmful waves due to the shape and, therefore, to counter the harmful waves due to the opposite phase angles in the target space (to be referred to as the "third configuring" hereinafter).

In another exemplary embodiment of this aspect of the invention, a system may be made by a process including the steps of: arranging a single counter unit to define a shape of an 1-D (or 2-D, 3-D) analog of the base unit and to emit counter electromagnetic waves; and the third countering. Such arranging may be replaced by the step of: arranging a single counter unit to define a shape of an 1-D (or 2-D, 3-D) analog of at least two of multiple base units and to emit counter electromagnetic waves.

In another exemplary embodiment of this aspect of the invention, a system may be made by a process including the steps of: arranging multiple counter units at least two of which are configured to define shapes of 1-D (or 2-D, 3-D) analogs of such a base unit and to emit counter electromagnetic waves; and the third countering. The above arranging may also be replaced by one of the steps of: arranging multiple counter units at least two of which are configured to define shapes of 1-D (or 2-D, 3-D) analogs of at least two but not all of multiple base units and then to emit counter electromagnetic waves; and arranging multiple counter units at least two of which are configured to define shapes of 1-D (or 2-D, 3-D) analogs of each of multiple base units and to emit counter electromagnetic waves.

More product-by-process claims may be constructed by modifying the foregoing preambles of the apparatus and/or method claims and by appending thereonto such bodies of the apparatus and/or method claims. In addition, such process claims may include one or more of the above features of the apparatus and/or method claims of the present invention.

As used herein, the term "units" collectively refers to both of a "base unit" and a "counter unit" of an electromagnetically-countered system of this invention, where such a system is abbreviated as the "EMC system" or simply as the "system" hereinafter. Such a classification between the "units" is primarily based upon their intended functions. That is, the "base unit" represents various parts of the EMC system which are to perform intended functions of the system such as, e.g., generating audible sounds from source signals (speakers and devices including such) or vice versa (microphones and devices including such), generating electromotive force by converting electric energy (electric motors and devices including such) or vice versa (generators), producing visible images from source signals (display elements such as a CRT, LED, OLED, and PDP, and devices including such), generating heat from electric energy (straight or coiled heating elements and devices including such), and the like. All of such "base units" irradiate the harmful waves while performing their intended functions, and these "base units" are always incorporated in the above devices. In contrary, the "counter unit" represents those parts of the EMC system which are to perform countering functions such as, e.g., canceling at least a portion of the harmful waves in the target space and/or suppressing or preventing the portion of such harmful waves from propagating toward the target space. When desirable, the "counter unit" may also be arranged to perform the functions intended for the "base unit" and, accordingly, serve as an extra "base unit" which also performs the countering function. This unit, however, is to be deemed as the "counter unit" within the scope of this invention unless otherwise specified. Within the scope of this invention, the "base unit" is therefore omnipresent in any prior art devices, while the "counter unit" is neither physically not functionally present in the prior art devices.

The "base unit" is to be distinguished from a "wave source" within the scope of this invention. More particularly, the "wave source" collectively refers to portions of the EMC system irradiating such harmful waves, whereas the "base unit" specifically refers only to the portions of the "wave source" which are directly responsible for irradiating the harmful waves and/or affecting propagation paths of such waves. For example, a speaker of a mobile phone is the "wave source" and the "base units" of such a phone includes a voice coil and a permanent magnet, where a cone and a bracket coupling to such a coil and magnet are portions of the "wave source" but not portions of the "base unit" because the cone and/or bracket neither generate the harmful waves nor affect the propagation paths thereof. Similarly, a motor of an actuating device is the "wave source," while the "base units" of the motor are permanent magnets and/or electromagnets incorporated to a rotor and/or a stator of the motor, where a shaft and a case of the motor are portions of the "wave source" but not portions of the "base units" because the shaft and/or case neither generate the harmful waves not affect the propagation paths thereof. Similarly, a heater of a heating device is the "wave source" and the "base unit" of the heating device is a straight or coiled heating element, where an insulative support and an external coating are portions of the "wave source" but not portions of the "base unit" because the support and/or coating neither generate such harmful waves nor affect their propagation paths. Accordingly, a shape of the "wave source" is generally different from a shape of the "base unit," where the "base unit" may have the shape simpler or more complex than that of the "wave source." However, the "base unit" may be deemed as a subset of the "wave source" and, therefore, such a "base unit" almost always defines a size which is smaller than or at most equal to that of the "wave source."

As used herein, the term "configuration" collectively refers a shape, size, and/or arrangement, while the term "disposition" collectively includes orientation, alignment, and/or distance. Accordingly, the "configuration" of the (counter or base) unit may refer to the shape of the unit, the size of the unit, and/or arrangement of the unit with respect to the other of the base and counter units. Similarly, the "disposition" of the unit may refer to the orientation and/or alignment of such a unit with respect to the other of the base and counter units, to the target space, to a direction of propagation of the harmful or counter waves, to a direction of the electric current flowing in or voltage applied across such a unit or the other of the base and counter units, and the like. The "disposition" of the unit may also refer to the distance to the other of the base and counter units therefrom, to the target space, and the like. When the system include multiple counter units, the "disposition" thereof may include the distance between at least two of such counter units.

Within the scope of the present invention, the term "wire" collectively refers to an article with a shape of a wire, a fiber, a filament, a rod, and/or a strand, and shapes of any other similarly elongated articles each of which may be straight or curved (i.e., curvilinear), and each of which may be formed into a loop, a coil, a roll, a spiral, a mesh, and the like. The term "strip" collectively refers to an article with a shape of a strip, a bar, a pad, and/or a tape, and shapes of any other planar or curved articles with large aspect ratios (i.e., ratios of lengths to widths or heights), each of which may be arranged straight or curved, each of which may be arranged in a two- or three-dimensional configuration, each of which may be arranged into a loop, a coil, a roll, a spiral, a mesh, and the like. In addition, the term "sheet" collectively refers to an article with a shape of a sheet, a slab, a foil, a film, a plate, and/or a layer, and shapes of any other articles which are wider than the "strip," each of which may be planar (i.e., two-dimensional or 2-D) or curved (i.e., three-dimensional or 3-D), each of which may be formed in a segment, a roll, and the like. The term "tube" collectively refers to an article which may define any of the shapes described hereinabove and to be described hereinafter and forming at least one lumen therethrough. Such a "tube" may be arranged straight or curved, may be arranged into a loop, a coil, a roll, a spiral, a mesh, and the like. The term "coil" collectively refers to an article defining a shape of a helix and/or a spring, and shapes of any other articles winding around an object along a longitudinal or short axis of such an object at a constant distance from the object, and the like. The "coil" may be arranged straight or curved, may also be arranged into a loop (such as a toroid), a coil, a roll, a spiral, a mesh, and the like. The term "spiral" collectively refers to an article defining a shape of another helix and/or spring which may, however, expand or shrink along the longitudinal oe short axis of an object, and shapes of any other articles winding around such an object at varying distances, and the like. It is appreciated that a planar "spiral"

may be formed on a single curvilinear plane which is normal to the longitudinal or short axis of the object. The term "mesh" collectively refers to an article with a shape a mesh, a net, a screen, a quilt, a fabric, and/or a garment, and shapes of any other articles which may be formed into a networking structure, a woven structure, an interwoven structure, and the like. The term "bundle" collectively refers to an article defining a shape of two or more of the same or different elongated shapes which are aligned side by side or laterally in such a manner that a cross-section of the "bundle" or a "bundled article" may include at least two of such shapes therein. The term "braid" collectively refers to an article with a shape of two or more of the same of different elongated shapes which are braided in such a manner that the "braid" or a "braided article" may consist of at least two of such shapes in a cross-section normal to a longitudinal and/or short axis thereof, where examples of such articles may include, but not be limited to, a thread, a yarn, any other articles made by prior art braiding techniques, and the like. It is to be understood that at least a portion of each of such articles formed according to the above terms in this paragraph may be arranged to be solid, hollow or porous such as, e.g., a foam, a sponge, and the like. It is also appreciated that each of such articles formed according to the foregoing terms of this paragraph may be arranged to include (or define) at least one hole, gap or opening.

Similarly and as used herein, the term "mixture" collectively refers to a liquid, a solution, a sol, a gel, an emulsion, a suspension, a slurry, and/or a powder, each of which may include therein multiple particles, particulates, grains, granules, filings, fragments, and/or pellets each of which may also have shapes of spheres, ellipsoids, cylinders, flakes, "wires," "strips," and the like, and each of which may be in a range of millimeters, microns or nanometers. When appropriate, such a "mixture" may include at least one solvent, at least one chemically, electrically, and/or magnetically inert filler for the purpose of providing mechanical strength and/or integrity thereto, and so on.

In addition, the term "combination" refers to a collection of different shapes examples of which may include, but not be limited to, the above wire, strip, sheet, tube, coil, spiral, mesh, their braid, and their bundle. The term "array" similarly refers to the collection of such shapes. However, the "array" refers to the "collection" which in addition forms multiple holes or openings therethrough.

As used herein, the terms "axial," "radial," and "angular" will be used in reference to a center axis of the system. Based thereupon, the term "axial direction" refers to a direction along the center axis of the system, while the term "radial direction" means another direction which is normal to such an "axial direction" and, therefore, which represents a direction extending away and outwardly from the center of the system. It is appreciated that such a "radial direction" may be other directions which extend away and outwardly from the center of the system and may be transverse but not necessarily perpendicular to the "axial direction." The term "angular direction" refers to another direction revolving about the "axial direction" in a clockwise or counterclockwise manner.

It is appreciated that definitions related to various electric and magnetic shields of this invention are similar to those as have been provided in the aforementioned co-pending Applications. Therefore, such definitions are deleted herein for simplicity of illustration.

Unless otherwise defined in the following specification, all technical and scientific terms used herein have the same meaning as commonly understood by one of ordinary skill in the art to which the present invention belongs. Although the methods or materials equivalent or similar to those described herein can be used in the practice or in the testing of the present invention, the suitable methods and materials are described below. All publications, patent applications, patents, and/or other references mentioned herein are incorporated by reference in their entirety. In case of any conflict, the present specification, including definitions, will control. In addition, the materials, methods, and examples are illustrative only and not intended to be limiting.

Other features and/or advantages of the present invention will be apparent from the following detailed description, and from the claims.

BRIEF DESCRIPTION OF THE DRAWING

FIGS. 6A to 6H are schematic perspective views of exemplary speakers which have counter units and electromagnetic (or magnetic) shields according to the present invention.

DETAILED DESCRIPTION OF THE PREFERRED EMBODIMENTS

Figure 1A:
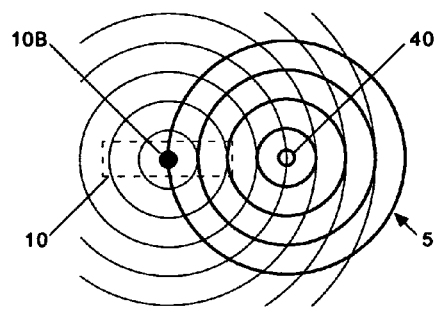
FIGS. 1A to 1F are top schematic views of exemplary electromagnetic countering mechanisms in each of which a single counter unit emits counter waves to counter harmful waves irradiated by a single base unit of a single wave source according to the present invention.

The present invention relates to an electromagnetically-countered system including at least one wave source irradiating harmful electromagnetic waves and at least one counter unit emitting counter electromagnetic waves for countering the harmful waves by the counter waves, e.g., by canceling at least a portion of the harmful waves by the counter waves, by suppressing the harmful waves from propagating to a target space, and the like. More particularly, the present invention relates to generic counter units of the electromagnetically-countered systems and to various mechanisms for countering the harmful waves which are irradiated from various base units of the wave sources by the counter units. Accordingly, the counter unit may be shaped, sized, and/or arranged to match its configuration with configuration of the base unit of the wave source, thereby emitting such counter waves which automatically match characteristics of such harmful waves. In the alternative, the counter unit may be shaped, sized, and/or disposed in an arrangement which is defined along one or more wavefronts of the harmful waves, thereby emitting the counter waves which automatically match characteristics of the harmful waves. The present invention also relates to various counter units which are provided as analogs of the base unit of the wave source, where the analog may approximate the base unit which is more complex than such a counter unit, where the three- or two-dimensional base unit may also be approximated as the two- or one-dimensional analog, and the like. The present invention also relates to multiple simple counter units which are simpler than the base unit but disposed in an arrangement approximating such a shape and/or arrangement of the base unit. The present invention also relates to the counter unit which may be shaped and/or sized according to the configuration of the base unit and disposition thereof. In addition, the present invention relates to various countering modes where a single counter unit may counter a single base unit, at least two but not all of multiple base units or all of multiple base units, where multiple counter units may counter a single base unit, more base units or less multiple units, and the like. The present invention then relates to various electric and/or magnetic shields which may be used alone or in conjunction with the counter units to minimize irradiation of the harmful waves from the system.

The present invention also relates to various methods of countering the harmful waves by the counter waves by such source matching or wave matching. More particularly, the present invention relates to various methods forming the counter unit as an analog of the base unit and then emitting the counter waves matching such harmful waves, various methods of approximating the base unit by the simpler counter unit for the countering and various methods of approximating the base unit by multiple simpler counter units. The present invention also relates to various methods of disposing the counter unit along the wavefronts of the harmful waves and then emitting the counter waves for automatically matching such wavefronts of the harmful waves, various methods of disposing multiple counter units along the wavefronts of the harmful waves and then emitting the counter waves by the counter units for automatically matching such wavefronts, and the like. In addition, the present invention relates to various methods of manipulating the wavefronts of the counter waves by disposing the counter unit closer to and/or farther away from the target space with respect to the base unit, various methods of controlling radii of curvature of the wavefronts of the counter waves by incorporating one or multiple counter units emitting such counter waves of the same or opposite phase angles, various methods of adjusting the wavefronts of the counter waves by disposing one or multiple counter units defining the shapes similar to or different from the shapes of the base units, and the like. The present invention also relates to various methods of countering the harmful waves from one or multiple base units with the counter waves emitted by the single or multiple counter units. Accordingly, the present invention relates to various methods of emitting such counter waves from a single counter unit for the harmful waves irradiated by one or more base units, various methods of emitting such counter waves by two or more counter units for the harmful waves irradiated by a single or multiple base units, and the like. In addition, the present invention relates to various methods of minimizing irradiation of such harmful waves by incorporating such electric shields, by incorporating the magnetic shields, by incorporating one or both of such shields in conjunction with the above counter units, and the like.

The present invention further relates to various processes for providing various counter units and various systems incorporating one or multiple counter units therein. More particularly, the present invention relates to various processes for forming the counter units to emit the counter waves having the wavefronts similar to (or different from) such shapes of the counter units, various processes for forming the counter units as the above analogs of the base units, various processes for providing the counter units emitting such counter waves which define the similar or opposite phase angles, various processes for providing such counter units with the wavefronts shaped similar to the harmful waves, various processes for disposing the counter units in a preset arrangement and emitting therefrom the counter waves which have the wavefronts similar to such an arrangement, and the like. The present invention also relates to various processes for assigning the single counter unit to counter the harmful waves irradiated by the single base unit for a local countering or to counter such harmful waves from multiple base units for a global countering, various processes for assigning multiple counter units to counter the harmful waves irradiated by the single base unit for the global countering or to counter the harmful waves from multiple base units for the local or global countering depending on numbers of the counter and base units. The present invention further relates to various processes for incorporating the electric and/or magnetic shields for minimizing the irradiation of such harmful waves, and various processes for minimizing the irradiation of such harmful waves by employing such shields as well as the above counter units.

The basic principle of the counter units of the generic electromagnetically-countered systems of this invention is to emit the counter waves which form the wavefronts similar (or identical) to those of the harmful waves but define the phase angles at least partially opposite to those of such harmful waves. Therefore, by propagating such counter waves to the target space, the counter waves can effectively counter the harmful waves in the target space by, e.g., canceling at least a portion of such harmful waves therein and/or suppressing the harmful waves from propagating theretoward. To this end, the counter units are arranged to emit the counter waves which define the wavefronts matching those of the harmful waves by various mechanisms. In one example, such counter units are shaped similar (or identical) to the base units of the waves sources, or arranged similar (or identical) to such base units and, therefore, emit the counter waves which can counter the harmful waves in the target space. In another example, such counter units are disposed along one or more of the wavefronts of the harmful waves and emit the counter waves which are similar (or identical) to the harmful waves and, accordingly, counter the harmful waves in the target space. In these two examples, the counter units are to emit the counter waves with the wavefronts which are similar (or identical) to the shapes of such counter units themselves, and such counter waves are to define the phase angles which are at least partially opposite to the phase angles of the harmful waves. In another example, the counter units are shaped differently from the base units, but are rather disposed in an arrangement in which the counter waves emitted therefrom may match such harmful waves in the target space. In another example, the counter units are disposed across different wavefronts of the harmful waves but are to emit the counter waves which are similar (or identical) to the harmful waves and, therefore, counter the harmful waves in the target space. In the last two examples, the counter units may be arranged to emit the counter waves with the wavefronts may or may not be similar (or identical) to the shapes of the counter units themselves, while the counter waves are to define the phase angles which are at least partially opposite to those of the harmful waves.

The basic principle of the counter units of the generic electromagnetically-countered system of this invention may be implemented into various prior art devices for minimizing irradiation of the harmful waves therefrom. For example, the counter units may be implemented to any base units of electrically conductive wires, coils, and/or sheets or, in the alternative, into any electrically semiconductive and/or insulative wires, coils, and/or sheets for minimizing the irradiation of the harmful waves by countering such harmful waves by the counter waves, e.g., by canceling at least a portion of the harmful waves in the target space and/or suppressing the harmful waves from propagating toward the target space, where the counter units may be made of and/or include at least one electrically conductive, insulative or semiconductive material. The counter units may be implemented into any of such base units which define the shapes which may be formed by incorporating one or multiple wires, coils, and/or sheets, by modifying the shapes of one or multiple wires, coils, and/or sheets, where a few examples of the modified shapes may include a solenoid and toroid each formed by modifying the shape of such a coil. Therefore and in one example, such counter units may be implemented into various speakers such as cone-drive speakers, electrostatic speakers, and piezoelectric speakers for minimizing the irradiation of the harmful waves. Accordingly, any prior art devices including the electromagnetically-countered speakers such as earphones, headphones, wired phones, mobile phones, and audiovisual devices may be converted into the electromagnetically countered systems. Similarly, the counter units may be implemented into various microphones which are inverse examples of such speakers, and any prior art devices including such electromagnetically-countered microphones such as wired phones, mobile phones, audio and/or audiovisual sound systems, and an assembly of the earphone and microphone may be converted into the electromagnetically countered systems. In another example, such counter units may be implemented into various motors such as DC motors, universal motors, AC synchronous motors, AC induction motors, linear motors, and the like, for minimizing the irradiation of such harmful waves. Therefore, any prior art actuator devices including the electromagnetically-countered motors such as kitchen appliances (e.g., a food processor, a mixer, a juicer, a grinder, a blender, a squeezer, a can opener, a dish washer, a refrigerator, a freezer, a cooler, and so on), cooking appliances (e.g., an electric grill, an electric oven, an electric stove, an electric range, an electric toaster, an electric fan for such, and the like), household appliances (e.g., a cloth washer, a cloth dryer, an air conditioner, a garage opener, a dry or wet vacuum cleaner, and so on), tools (e.g., an electric drill, an electric saw, an electric screwdriver, an electric nail or staple gun, an electric sander, and the like), and personal hygiene devices (e.g., an electric razor, an electric toothbrush, an electric hair dryer, and the like) may be converted into the electromagnetically countered systems. Similarly, the counter units may also be implemented to various generators, and any prior art generating devices with the electromagnetically-countered generators such as AC generators, DC generators, and (automobile) alternators may also be converted into the electromagnetically countered systems. In another example, such counter units may be implemented into various transformers which include therein at least two coils, and any prior art devices including the electromagnetically-countered transformers such as step-up transformers, step-down transformers, and AC/DC adaptors of various electric devices may be converted into the electromagnetically countered systems. In another example, such counter units may be implemented to various heating unit including at least one resistive heating wire, heating strip, heating sheet, and/or heating coil for minimizing the irradiation of the harmful waves during heating. Accordingly, any prior art heating devices such as personal heating appliances (e.g., an electric mattress or mat, an electric blanket, an electric heating pad, and so on), cooking appliances (e.g., an electric grill, an electric oven, an electric stove, an electric range, an electric toaster, an electric toaster oven, and the like), and/or beauty-related appliances (e.g., a hair dryer, a hair setter, a hair curler, a hair steamer, and the like), may be converted into the electromagnetically countered systems. In another example, such counter units may be implemented into various light emitting units for minimizing the irradiation of such harmful waves during lighting. Accordingly, any prior art display devices such as a cathode ray tube, a light emitting device, an organic light emitting device, an inorganic light emitting device, and a plasma display panel may be converted into the electromagnetically countered systems.

It is to be understood that various counter units of such generic electromagnetically-countered systems (to be abbreviated as "EMC systems" or simply "systems" hereinafter) of this invention may be incorporated to any electrical and/or electronic devices each of which may have at least one base unit and, accordingly, may irradiate the harmful waves including electric waves (to be abbreviated as "EWs" hereinafter) and magnetic waves (to be abbreviated as "MWs" hereinafter) having frequencies of about 50 to 60 Hz and/or other EWs and MWs of higher frequencies. It is also appreciated that the generic EMC systems of this invention may also be incorporated into any portable or stationary electric and/or electronic devices which include at least one base unit detailed examples of which have been provided heretofore and will be provided hereinafter. It is further appreciated that such counter units may be provided in a micron-scale and incorporated to semiconductor chips and circuits such as LSI and VLSI devices and that such counter units may be provided in a nano-scale and incorporated into various nano devices including at least one base unit which in this case may be a single molecule or a compound or may be a cluster of multiple molecules or compounds.

Various aspects and/or embodiments of various systems, methods, and/or processes of this invention will now be described more particularly with reference to the accompanying drawings and text, where such aspects and/or embodiments thereof only represent different forms. Such systems, methods, and/or processes of this invention, however, may also be embodied in many other different forms and, accordingly, should not be limited to such aspects and/or embodiments which are set forth herein. Rather, various exemplary aspects and/or embodiments described herein are provided so that this disclosure will be thorough and complete, and fully convey the scope of the present invention to one of ordinary skill in the relevant art.

Unless otherwise specified, it is to be understood that various members, units, elements, and parts of various systems of the present invention are not typically drawn to scales and/or proportions for ease of illustration. It is also to be understood that such members, units, elements, and/or parts of various systems of this invention designated by the same numerals may typically represent the same, similar, and/or functionally equivalent members, units, elements, and/or parts thereof, respectively.

In a generic aspect of this invention, an EMC system includes at least one wave source and at least one counter unit and counters harmful electromagnetic waves (to be abbreviated as the "harmful waves" hereinafter) which are irradiated from the wave source with counter electromagnetic waves (to be abbreviated as the "counter waves" hereinafter) which are emitted from the counter units. The wave source always includes at least one base unit which is the real source of such harmful waves, i.e., irradiating the harmful waves, affecting propagation paths of the harmful waves while maintaining or altering their amplitudes and/or phase angles, and so on, where examples of such a base unit may include, but not be limited to, a conductive or semiconductive article such as a wire, a strip, a plate, a ring thereof, a coil thereof, a spiral thereof, and a mesh thereof all of which emit such harmful waves when electric current flows therein, an insulative article such as a wire, a strip, a plate, a ring thereof, a coil thereof, a spiral thereof, and a mesh thereof all of which can not carry such electric current but emit the harmful waves when electric voltage is applied thereacross, a permanent magnet which can affect the direction, paths, and/or amplitudes of such harmful waves, and the like. The wave source further includes at least one optional part which mechanically supports or retains such a base unit but which neither irradiates nor affects the propagation paths of the harmful waves, where examples of the optional part may include, but not be limited to, a case enclosing the base unit, a protective cover, a coupler, any parts in which such current does not flow, any parts across which the voltage is not applied, and the like. The counter unit is arranged to emit such counter waves capable of countering the counter waves, e.g., by canceling the harmful waves and/or by suppressing the harmful waves from propagating along a specific direction. The counter unit may be arranged to counter the harmful waves in every direction from the base unit of the wave source, e.g., above, below and around such a base unit. However, such an embodiment may be costly to implement, may not be feasible, and may not be necessary, particularly when the EMC system is to be used in a specific orientation by an user who is to be protected from such harmful waves. In such a case, the counter is arranged to counter the harmful waves only around a specific target space (or area) which is generally defined between the base unit and the user (or a specific body part thereof).

In order for the counter waves to counter (i.e., cancel and/or suppress) such harmful waves, there are a few prerequisite which the counter waves must satisfy. The first is the phase angles of the counter waves. In general, such counter waves preferably define the phase angles which are at least partially or substantially opposite to those of the harmful waves so that the counter waves may cancel and/or suppress the harmful waves when propagated to the target space from the same side as the base unit. In the alternative, the counter waves may have the phase angles which are at least partially similar (or identical) to those of the harmful waves so that such counter waves cancel and/or suppress the harmful waves when propagated to the target space from an opposite side of the base unit. When the system includes multiple counter units, each counter unit may emit the counter waves having the same, similar or different phase angles. The next is the amplitudes of the counter waves. In contrary to the phase angles, such counter waves may define various amplitudes which, however, effectively counter the harmful waves in the target space. When disposed closer to the target space than the base unit, the counter unit has only to emit the counter waves with the amplitudes less than those of the harmful waves. By the same token, the counter unit disposed farther from the base unit has to emit the counter waves with the amplitudes greater than those of the harmful waves, while the counter unit disposed flush with the base unit with respect to the target space has to emit the counter waves with the similar or same amplitudes as the harmful waves. When the system includes multiple counter units, all of such counter units may be disposed at similar distances from the base unit and/or target space or, alternatively, at least two of the counter units may be disposed at different distances from the base unit and/or target space. In addition to the distances and/or dispositions thereof, such counter waves may have various intensities depending upon whether the counter waves counter the harmful waves throughout an entire portion of the target space or only at preset positions inside such a target space. For example, the counter unit preferably emits the counter waves which are capable of countering the harmful waves throughout the target space as the user may be situated anywhere across the target space. When the user is to be situated only in preset positions of the target space, however, the counter may be shaped, sized, arranged, and then disposed to emit the counter waves which best counter the harmful waves in such positions but not with such an efficiency in other parts of the target space.

Once the counter unit is arranged to emit the counter waves defining proper phase angles and amplitudes, such a counter unit may be shaped, sized, arranged, and disposed in order to counter the harmful waves depending on detailed countering mechanisms.

In one example, the counter unit may be shaped, sized, and/or arranged similar (or identical) to the base unit, which is to be referred to as a "source matching" hereinafter. The basic concept of the "source matching" is that the counter unit may emit the counter waves defining wavefronts similar to a configuration (i.e., a shape, a size, and an arrangement) of the counter unit and that such wavefronts of the counter waves automatically match wavefronts of the harmful waves, and the counter waves counter the harmful waves due to the similarity between the configurations of the counter and base units. When the system includes multiple base units, the single counter unit may then be arranged to emit the counter waves capable of countering the harmful waves irradiated by one of such base units or countering a sum of the harmful waves irradiated by at least two or all of such base units. When the system includes multiple counter units, such counter units may emit the counter waves capable of countering the harmful waves emitted by the single base unit or multiple base units. When the system includes multiple counter and base units, such counter waves from each counter unit may counter the harmful waves by each base unit, a sum of such counter waves from at least two counter units may counter the harmful waves from one of the base units, the counter waves from a single counter unit may counter a sum the harmful waves from at least two base units, a sum of the counter waves from all of such counter units may then counter a sum of the harmful waves from all of the base units, and the like. It is preferred in this "source matching" that the counter unit emit the counter waves with the wavefronts of the configuration similar to that of the counter unit. It is, however, possible that such a counter unit emits the counter waves with the wavefronts with the configuration different from that of the counter unit, that the wavefronts of a sum of the counter waves emitted by multiple counter units may have the configuration different from the configuration of each counter unit or the arrangement of the counter units, and the like, as long as the counter waves may counter the harmful waves in such a target space.

In another example, the counter unit may be disposed (i.e., oriented, aligned, and/or positioned) in such a manner that at least one wavefront of the counter waves may match at least one wavefront of the harmful waves, where such a mechanism will be referred to as a "wave matching" hereinafter. The basic concept of the "wave matching" lies in the that the counter waves may counter the harmful waves when the counter unit is disposed in such a position to match the wavefronts of such counter waves with the wavefronts of the harmful waves as far as the configuration of the counter unit may be properly adjusted to satisfy such "wave matching." When the system includes multiple base units, a single counter unit may be arranged to emit the counter waves capable of matching and countering the harmful waves irradiated by one of the base units or, alternatively, matching and countering a sum of the harmful waves irradiated by at least two or all of the base units. When such a system includes multiple counter units, the counter units may emit the counter waves capable of countering the harmful waves emitted by a single base unit or multiple base units. When the system includes multiple counter and base units, such counter waves from each counter unit may counter the harmful waves by each base unit, a sum of the counter waves emitted by at least two counter units may counter the harmful waves from one of the base units, the counter waves from a single counter unit may counter a sum the harmful waves from at least two base units, a sum of the counter waves from all of such counter units may counter a sum of the harmful waves irradiated by all of the base units, and the like, as long as at least one of the wavefronts of the counter waves may match at least one of the wavefronts of the harmful waves in the target space.

Various counter units constructed based on the source matching and/or wave matching are to be disclosed hereinafter. It is appreciated in the source matching that there does not exist any one-to-one correlations between the configuration of such a counter unit and the configuration of the counter waves emitted thereby. That is, the counter waves of certain configuration (or wave characteristics) may be obtained by a single counter unit which defines a certain shape and size and is provided in a certain arrangement, by another counter unit which defines a similar shape and size but is provided in another arrangement, by another counter unit which has a different shape and size but is provided in a similar arrangement, by at least two counter units defining preset shapes and sizes and provided in a preset arrangement, by the same number of counter units defining different shapes and/or sizes or in a different arrangement, by a different number of counter units defining similar shapes and/or sizes or in a similar arrangement. It is similarly appreciated in the above wave matching that there does not exist an one-to-one correlation between the disposition of the counter unit and the wavefronts of the counter waves emitted by the counter unit. In other words, the wavefronts with certain shapes may be obtained by a single counter unit which defines a certain configuration and is disposed in a certain position with respect to the base unit and/or target space, by another single counter unit which forms another configuration and which is disposed in another position, by at least two counter units which have preset configurations and are disposed in preset positions, by the same number of counter units defining different configurations and disposed in different positions, by a different number of counter units which define different configurations and which are disposed in different positions, and the like. It is, accordingly, appreciated that such counter units may be embodied in many other different forms and should not be limited to the following aspects and/or their embodiments which are to be set forth herein. Rather, various exemplary aspects and/or embodiments described herein are provided so that this disclosure will be thorough and complete, and fully convey the scope of the present invention to one of ordinary skill in the relevant art.

In another aspect of the present invention, a single generic counter unit may be provided for a single generic base unit to counter the harmful waves from the base unit by the counter waves from the counter unit. FIGS. 1A to 1F show top schematic views of exemplary electromagnetic countering mechanisms in each of which a single counter unit emits the counter waves capable of countering the harmful waves which are irradiated from a single base unit of a single wave source according to the present invention, where the base unit is a point source in FIGS. 1A to 1C and 1F, while the base unit is an elongated source in FIGS. 1D and 1E. It is appreciated that these figures, however, may also be interpreted in different perspectives. For example, such figures may be interpreted as the top cross-sectional views, where the base units of FIGS. 1A to 1C and 1F are wires extending perpendicular to the sheet, and the base units of FIGS. 1D and 1E are strips or rectangular rods also extending normal to the sheet. In another example, the figures may be interpreted as sectional views of more complex articles, where the base units of FIGS. 1A to 1C and 1F may correspond to sections of coils, spirals, meshes, and the like, while the base units of FIGS. 1D and 1E may similarly correspond to sections of curvilinear rods or strips. It is also appreciated in these figures that such base units are enclosed in the wave sources which may be cases or other parts of such a system which do not irradiate such harmful waves. It is further appreciated in all of these figures that the EMC systems are disposed in such a way that the target space is formed to the right side of the counter and base units.

Figure 1D:
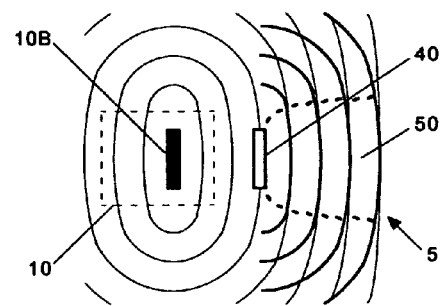

In one exemplary embodiment of such an aspect of the invention and as described in FIG. 1A, an EMC system 5 includes a single rectangular wave source 10 and a single counter unit 40, where the source 10 includes therein a single base unit 10B defining a shape of a point source. The counter unit 40 is similarly shaped as another point source and disposed to the right side of the base unit 10B. In this arrangement, the counter unit 40 emits the counter waves of which wavefronts are identical to those of the harmful waves irradiated by the base unit 10B. Because the counter unit 40 is disposed closer to a hypothetical target space on the right side of the figure, such counter wavefronts always define radii of curvature smaller than those of the harmful wavefronts. Accordingly, the counter unit 40 may counter (i.e., cancel or suppress) the harmful waves only along a line connecting the counter and base units 40, 10B or in its vicinity. It is appreciated that such an embodiment corresponds to the source matching which turns out to be ineffective due to a discrepancy in the radii of curvature of the wavefronts of the counter and harmful waves.

Figure 1B:
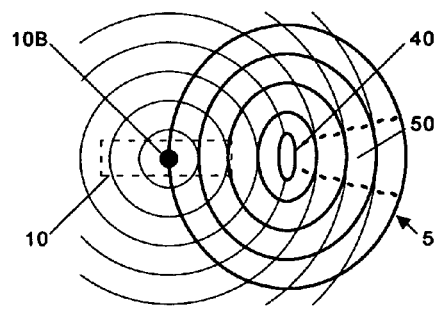
Figure 1E:
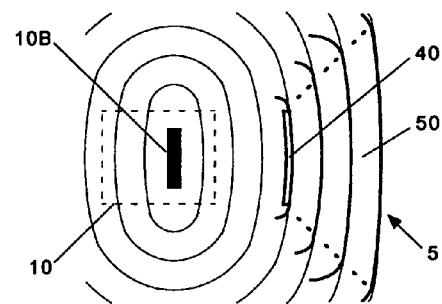

In another exemplary embodiment of this aspect of the invention and as depicted in FIG. 1B, an EMC system 5 includes a single counter unit 40 and a single rectangular wave source 10 with a single base unit 10B disposed therein. The base unit 10B is similar to that of FIG. 1A, however, the counter unit 40 is elongated, oriented vertically along its length, and disposed on the right side of the base unit 10B. Due to its elongated shape, the counter unit 40 emits the counter waves whose wavefronts are also elongated vertically and, therefore, define the radii of curvature which are greater than those of FIG. 1A and which match those of the harmful waves. Accordingly, such a counter unit 40 defines a target space 50 across which the counter waves counter the harmful waves to a preset extent. It is to be understood that such an embodiment corresponds to the wave matching mechanism in that the counter unit 40 is shaped similar to one of the harmful wavefronts.

Figure 1C:
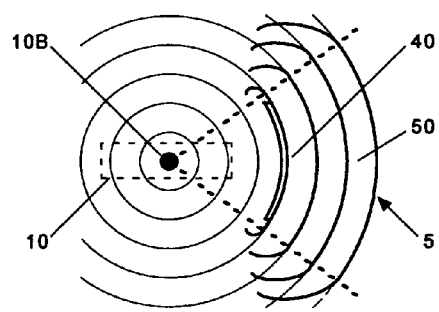

In another exemplary embodiment of this aspect of the invention and as depicted in FIG. 1C, an EMC system 5 includes a single counter unit 40 and a single rectangular wave source 10 with a single base unit 10B disposed therein. The base unit 10B is similar to that of FIG. 1A, however, the counter unit 40 is shaped and sized to conform to one wavefront of such harmful waves. That is, the counter unit 40 is shaped as an arc and disposed in an orientation concave to the right side of the figure or to the target space 50. Because of its arcuate shape, such a counter unit 40 emits the counter waves of which wavefronts are also arcuate and, therefore, define the radii of curvature which are similar or identical to those of the harmful waves. Therefore, the counter unit 40 defines a target space 50 across which the counter waves counter the harmful waves to a preset extent. It is appreciated that such an embodiment corresponds to another wave matching mechanism and that the counter waves emitted form this arcuate counter unit 40 better match such harmful wavefronts and define the target space 50 which expands over a wider angle around the base unit 10B than those of FIGS. 1A and 1B.

In another exemplary embodiment of this aspect of the invention and as depicted in FIG. 1D, an EMC system 5 includes a single counter unit 40 and a single rectangular wave source 10 with a single base unit 10B. Contrary to those of the above, this base unit 10B is rectangular and oriented vertically along its length or its long axis, and irradiates the harmful waves of which wavefronts define vertical and relatively straight portions which are attributed to the length or long axis of the base unit 10B. The counter unit 40 is shaped and sized similar or identical to the base unit 10B, and disposed in the same orientation as the base unit 10B. This orientation may be viewed to dispose the counter unit 40 along the vertical straight portions of the wavefronts of the harmful waves. The counter unit 40 also emits the counter waves whose wavefronts define vertical and relatively straight portions, similarly due to the length or long axis thereof. Because such portions of the counter wavefronts match those of the harmful wavefronts, the counter unit 40 forms the target space 40 to the right side. This embodiment corresponds to the source matching, wave matching or their combination. It is to be understood that the counter unit of FIG. 1A is shaped and sized as the base unit but ineffective due to a discrepancy in the radii of curvature between the wavefronts of the counter and source waves. The counter unit 40 of this embodiment is similarly shaped and sized as the base unit 10B but efficiently counter such harmful waves in the target space 50. The primary reason of this countering lies in the fact that both of the harmful and counter waves define along their wavefronts the vertical straight portions which generally do not depend upon the radii of curvature thereof. Otherwise, configuring the counter unit 40 similar to the base unit 10B and then disposing such a counter unit 10 between the base unit 10B and target space generally do not provide an efficient countering, where further details of this front arrangement are to be provided below. It is appreciated that such an embodiment corresponds to the source matching in which the counter unit 40 is shaped, sized, and/or arranged similar (or identical) to the base unit 10B.

In another exemplary embodiment of this aspect of the invention and as depicted in FIG. 1E, an EMC system 5 includes a single counter unit 40 and a single rectangular wave source 10 with a single base unit 10B which is similar to that shown in FIG. 1D. The counter unit 40, however, is shaped and sized to conform to one wavefront of such harmful waves. Similar to that of FIG. 1C, the counter unit 40 is shaped as an arc and disposed in an orientation concave to the right side of the figure or target space 50. Because of its arcuate shape, such a counter unit 40 emits such counter waves of which wavefronts are also arcuate and, therefore, define the radii of curvature which are similar or identical to those of the harmful waves, not only along their vertical straight portions but also along their curved portions, mainly due to the arcuate shape of the counter unit 40. Accordingly, such a counter unit 40 defines a target space 50 which also expands over a wide angle therearound and across which the counter waves effectively counter such harmful waves. It is to be understood that this embodiment corresponds to another wave matching mechanism.

Figure 1F:
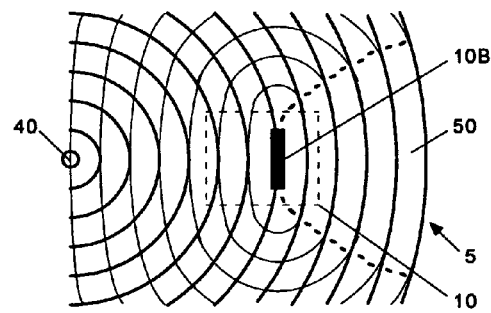

In another exemplary embodiment of this aspect of the invention and as depicted in FIG. 1F, an EMC system 5 includes a single counter unit 40 and a single rectangular wave source 10 which has a single base unit 10B therein. Both of the counter and base units 40, 10B are identical to those of FIG. 1A. However, the counter unit 40 is disposed on an opposite side of a target space 50 with respect to the base unit 10B and aligned with the base unit 10B as are the cases with the preceding figures. In this arrangement, the counter unit 40 emits the counter waves of which wavefronts are identical to those of the harmful waves irradiated by the base unit 10B. Because the counter unit 40 is disposed farther away from the target space 50, such counter wavefronts define the radii of curvature which approach and then match those of the harmful wavefronts when disposed at a proper distance from the base unit 10B. Accordingly, the counter unit 40 disposed in this rear arrangement may effectively counter the harmful waves and defines the target space 50 expanding over a wide angle around the base unit 10B. It is appreciated that the sole difference between the counter units of FIGS. 1A and 1F is their dispositions, i.e., one disposed in the "front arrangement" of FIG. 1A and another disposed in the "rear arrangement" of FIG. 1F. It is also appreciated that the rear arrangement is not necessarily superior to the front arrangement and that further details of selecting the proper arrangement are to be provided below. It is further appreciated that this embodiment corresponds to the wave matching in which the counter unit 40 is disposed at the position for matching the harmful wavefronts with the counter wavefronts.

Although not included in the figures, a single counter unit may be disposed in an arrangement flush with the base unit with respect to the target space, flush with a direction of propagation of the harmful waves, flush with another direction along which electric current flows in the base or counter unit, flush with another direction in which electric voltage is applied across the base or counter units, and so on. In this "lateral" arrangement, the radii of curvature of the counter wavefronts automatically match those of the harmful wavefronts and, therefore, the counter waves effectively match and then counter the harmful waves in the target space. For this arrangement, however, the wave source has to provide a space in which the counter unit may be incorporated. Therefore, the counter unit may be implemented inside the wave source and close to the base unit thereof when applicable. Otherwise, the counter unit may instead be disposed over, below or beside the wave source and as close to the base unit as possible. It is appreciated, however, that the counter unit disposed next to the base unit may propagate the counter waves onto the base unit and obstruct normal operation of the base unit. Accordingly, the lateral arrangement is preferably selected only when such an arrangement may not obstruct the normal operation of the base unit, wave source including such or EMC system including such. When the lateral arrangement does not affect the operation of the base unit but the counter unit may not be disposed close to the base unit due to space limitations, two or more counter units may be disposed on opposing sides (e.g., left and right, top and bottom, front and rear, and the like) of such a base unit and as close to the base unit as possible. Such counter units may also be arranged to emit the counter waves a sum of which may be symmetric or skewed toward a preset direction based on the wave characteristics of the harmful waves.

In another aspect of the present invention, multiple generic counter unit may be provided for a single generic base unit for countering the harmful waves irradiated by the base unit with the counter waves emitted by all of such counter units or emitted by at least two but not all of such counter units. FIGS. 2A to 2F are top schematic views of exemplary electromagnetic countering mechanisms in each of which multiple counter units emit counter waves to counter harmful waves irradiated from a single base unit of a single wave source according to the present invention, where the base unit is a point source in FIGS. 2A to 2E, while the base unit is an elongated source in FIG. 2F. It is appreciated that these figures, however, may also be interpreted in different perspectives. For example, such figures may be viewed as the top cross-sectional views, where the base units of FIGS. 2A to 2E are wires extending perpendicular to the sheet, and the base unit of FIG. 2F is a strip or a rectangular rod also extending normal to the sheet. In another example, the figures may be interpreted as sectional views of more complex articles, where the base units of FIGS. 2A to 2E may correspond to sections of coils, spirals, meshes, and the like, whereas the base unit of FIG. 2F may similarly correspond to sections of curvilinear rods or strips. It is also appreciated in these figures that such base units are enclosed in the wave sources which may be cases or other parts of such a system which do not irradiate such harmful waves. It is further appreciated in all of these figures that the EMC systems are disposed in such a way that the target space is formed to the right side of the counter and base units.

Figure 2A:
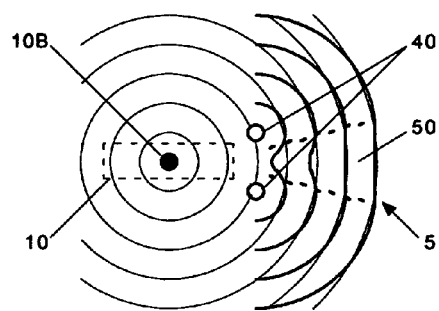
FIGS. 2A to 2F are top schematic views of exemplary electromagnetic countering mechanisms in each of which multiple counter units emit counter waves to counter harmful waves irradiated by a single base unit of a single wave source according to the present invention.
Figure 2D:
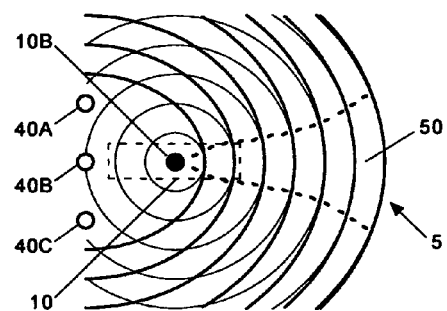

In one exemplary embodiment of such an aspect of the invention and as described in FIG. 2A, an EMC system 5 includes two counter units 40 and a single wave source 10 including a single base unit 10B. The base unit 10B is similar to those of FIGS. 1A to 1C, while a pair of counter units 40 are disposed between the base Ni 10B and a target space 50. Such counter units 40 are also disposed symmetric to the base unit 10B and flush with each other with respect thereto, i.e., the counter units 40 are disposed at an equal distance from the base unit 10B and/or target space 50. Such counter units 40 are arranged to emit the counter waves of the same phase angles so that the wavefronts of the counter waves from each counter unit 40 are superposed onto each other while increasing their amplitudes. As the counter waves propagate, their wavefronts which correspond to a sum of each set of wavefronts from each counter unit 40 increase their radii of curvature as if they are emitted by the elongated counter units of FIGS. 1B to 1E. Therefore, the counter wavefronts match the harmful wavefronts, and the pair of counter units 40 match and counter the base unit 10B while defining the target space 50 expanding over a limited angle therearound. It is to be understood that disposing two or more counter units 40 result in flattening the wavefronts of the counter waves and increasing the radii of curvature of the superposed portions of the counter wavefronts. It is further appreciated that this arrangement corresponds to the wave matching in which multiple counter units 40 are disposed along one wavefront of the harmful waves.

Figure 2B:
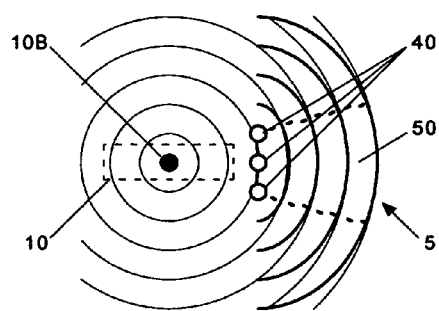
Figure 2E:
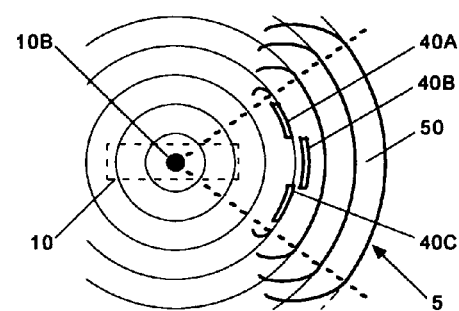

In another exemplary embodiment of this aspect of the invention and as depicted in FIG. 2B, an EMC system 5 includes three counter units 40 and a single wave source 10 enclosing therein a single base unit 10B. The base unit 10B is similar to those of FIGS. 1A to 1C, while the counter units 40 are similar to those of FIG. 2A such that all counter-units 40 are disposed between the base unit 10B and target space 50 and flush with the base unit 10B. However, the system 5 includes one more counter unit 40 so that an array of three counter units 40 approximate the wavefronts of such harmful waves better than those of FIG. 2A. Accordingly, the counter units 40 emit the counter waves which better counter the base unit 10B and define the target space 50 expanding over a wider angle therearound than those of FIG. 2A. It is appreciated that disposing three counter units 40 result in further flattening the superposed wavefronts of the counter waves and also result in increasing the radii of curvature of such portions of the wavefronts of the counter waves. It is also appreciated that this arrangement is another wave matching where all three counter units 40 are disposed along one wavefront of the harmful waves.

Figure 2C:
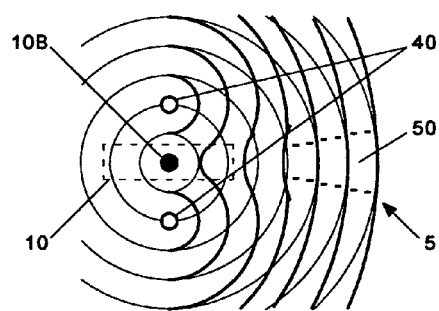
Figure 2F:
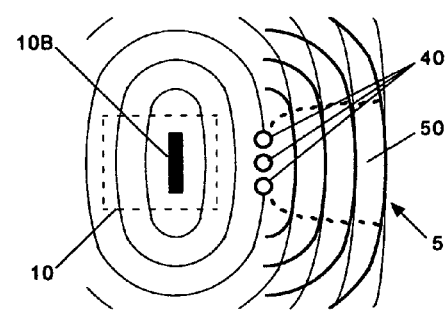

In another exemplary embodiment of this aspect of the invention and as depicted in FIG. 2C, an EMC system 5 includes two counter units 40 and a single wave source 10 including a single base unit 10B which is similar to those of FIGS. 1A to 1C. Two counter units 40 are disposed on opposite sides of the base unit 10B at an equal distance therefrom and also flush with the base unit 10B with respect to a target space 50. Similar to those of all of the preceding embodiments, such counter units 40 emit the counter waves defining the similar or identical phase angles so that the counter waves emitted by each of such counter units 40 superpose onto each other for not only increasing their amplitudes but also flattening the superposed portions of their wavefronts while increasing the radii of curvature of such wavefronts. Accordingly, the counter units 40 counter the harmful waves and define the target space 50 spanning around a rather limited angle therearound. It is appreciated that this arrangement is rather the source matching than the wave matching in that the counter units 40 are disposed in the symmetric arrangement and effect the elongated counter unit arranged flush with the base unit 10B.

In another exemplary embodiment of this aspect of the invention and as depicted in FIG. 2D, an EMC system 5 includes three counter units 40 and a single wave source 10 enclosing therein a single base unit 10B which is similar to those of FIGS. 1A to 1F. Contrary to those of FIG. 2B, three counter units 40 are disposed on an opposite side of a target space 50 with respect to the base unit 10B. The counter units 40 are arranged flush with each other relative to the base unit 10B and target space 50 and also spaced away from each other at an equal distance. Similar to those of FIGS. 2A to 2C, both of outer counter units 40A, 40C are arranged to emit the counter waves defining the phase angles at least partially opposite to those of the harmful waves so that superposed portions of the wavefronts of the counter waves are flattened while increasing their radii of curvature. Contrary to those of the preceding figures, a middle counter unit 40B is arranged to emit the counter waves defining the phase angles which are at least partially similar to those of such harmful waves and opposite to those of the counter waves emitted by the outer counter units 40A, 40C. Therefore, a net effect of incorporating the middle counter unit 40B is to sharpen the curvature of the superposed portions of the wavefronts of a sum of the counter waves and to define the target space 50 expanding around a narrower angle around the base unit 10B, as manifest in a comparison between the target spaces 50 of FIGS. 1F and 2D. That is, by incorporating multiple counter units 40A-40C emitting the counter waves of the phase angles opposite to each other, it is feasible to precisely manipulate the wavefronts of the sum of such counter waves and their radii of curvature for better matching the wavefronts of the harmful waves. It is appreciated that such an embodiment may corresponds to the source matching, wave matching or a combination thereof.

The counter units 40A-40C of this embodiment may be incorporated in different arrangements. For example, only two counter units may be included to emit the counter waves with opposite phase angles, where resulting wavefronts of the sum of the counter waves are not symmetric but skewed to one or an opposite side. In addition, the distances between the counter units may be manipulated to adjust the wavefronts of a sum of the counter waves regardless of the number of the counter units. Moreover, the counter units emitting the counter waves defining the phase angles similar to those of the harmful waves may be employed as the outer units to further sharpen the superposed portions of the counter waves.

In another exemplary embodiment of this aspect of the invention and as depicted in FIG. 2E, an EMC system 5 includes three counter units 40 and a single wave source 10 enclosing therein a single base unit 10B which is similar to those of FIGS. 1A to 1C. The counter units 40A-40C are also similar to those of FIG. 2B so that all of such counter units 40A-40C are disposed between the base unit 10B and target space 50 and similar to each other, that the counter units 40A-40C emit the counter waves of the same or similar phase angles, and so on. However, each counter unit 40A-40C is arranged to form an arcuate article shaped and sized to match a portion of a wavefront of the counter waves. In addition, both of upper and lower counter units 40A, 40C are spaced away from each other and also disposed along one wavefront of the harmful waves, whereas a middle counter unit 40B is disposed between the upper and lower counter units 40A, 40C and along an adjacent wavefront of the harmful waves in such a manner that superposed portions of the wavefronts of a sum of the counter waves are flattened while defining larger radii of curvature and match the wavefronts of the harmful waves, thereby forming a target space 50 which expands over a wide angle around the base unit 10B. It is to be understood that this arrangement is another wave matching where all three counter units 40A-40C are disposed along multiple wavefront of the harmful waves.

In another exemplary embodiment of this aspect of the invention and as depicted in FIG. 2F, an EMC system 5 includes three counter units 40 and a single wave source 10 enclosing therein a single base unit 10B. While the base unit 10B is similar to those of FIGS. 1D and 1E, the counter units 40 are similar to those of FIG. 2B and emit the counter waves which are flattened and define vertical straight portions therealong. Therefore, the counter waves match the vertical straight portions of the harmful waves and define a target space 50 similar to that of FIG. 1D. It is appreciated that this embodiment is another source matching in which three counter units 40 approximate the elongated base unit 10B.

In another aspect of the present invention, a single generic counter unit may also be provided for multiple generic base units for countering the harmful waves from such base units by the counter waves from the counter unit. In one example, such a counter unit may be arranged to counter a sum of the harmful waves irradiated by each base units, where detailed disposition of the counter unit may depend upon configurations and/or dispositions of the base units, amplitudes and/or directions of the harmful waves irradiated by such base units, and the like. Based thereupon, the counter unit may be disposed symmetrically to all or at least some of the base units, may be incorporated in the front, rear or lateral arrangement, and the like, where such arrangements are generally referred to an "global or overall countering" hereinafter. In another example, the counter unit is rather arranged to counter the harmful waves irradiated by only one of multiple base units, where such an arrangement is generally referred to as "local or individual countering" hereinafter. This local countering may only be effective when other uncountered base units irradiate negligible amounts of such harmful waves, when other uncountered base units irradiate non-negligible amounts of the harmful waves to other directions than the target space, and the like. Otherwise, it is preferred to manipulate the counter unit to counter the harmful waves of the uncountered base units, to include additional counter units for countering those harmful waves, and the like.

It is appreciated that various countering mechanisms described hereinabove for a single base unit may equally be applied to the system with multiple base units in the global countering mechanism. That is, the above countering mechanisms may be applied not to such harmful waves irradiated by the single base unit but to a sum of the harmful waves irradiated by multiple base units. When the system is to operate in the local countering mechanism, the aforementioned mechanisms may also be applied to each of multiple base units regardless of an exact number of such base units.

In another aspect of the present invention, multiple generic counter unit may also be provided for multiple generic base units for countering the harmful waves from such base units by the counter waves from the counter unit. In one example, multiple counter units are provided in the same number as the base units and each counter unit is arranged to counter only one of such base units in the local countering mechanism. Alternatively, at least one of such counter units may counter only one of such base units based upon the local countering mechanism, while at least one another of the counter units may counter at least two of the base units in the global countering mechanism. In another example, a less number of counter units are provided such that each counter unit is arranged to counter at least two of the base units based on the global countering mechanism, that at least one of the counter units counters one of the base units based on the local countering mechanism while at least one another of the counter units counters at least two of the base units in the global countering mechanism, and the like. In another example, a greater number of counter units are provided such that each base unit may be countered by at least two of the counter units, that at least one of the counter units counters one of the base units in the local countering mechanism and at least one another of the counter units may counter at least two of such base units in the global countering mechanism, and so on. In all of these examples, any of the above front, rear or lateral countering mechanisms may be used by the counter units, where such countering mechanisms may be same or different for each counter unit.

Configurational and/or operational variations of such EMC systems and their counter units as well as configurational and/or operational modifications of such EMC systems and their counter units as exemplified in FIGS. 1A to 1F and FIGS. 2A to 2F also fall within the scope of the present invention.

As described above, a typical EMC system includes at least one wave source and at least one counter unit, where the wave source in turn includes or encloses at least one base unit therein and where the counter unit may include at least one optional electric connector such as a lead wire and at least one optional coupler for coupling the counter unit to other parts of the system. The EMC system may also include at least one optional case member which encloses at least a portion of the base unit, at least a portion of the counter unit, and the like. Alternatively, an entire portion of the counter and/or base units may be exposed with or without such a case member.

More specifically, the counter unit consists of various parts such as at least one body, at least one optional support, and at least one insert. The body of the counter unit qualitatively corresponds to the base unit of the wave source in that such a body is the sole component of the counter unit which emits the counter waves when the electric current flows therein, when the electric voltage is applied thereacross, and the like. Therefore, such a body may preferably be made of and/or include at least one electric conductor when the electric current is to flow therein, may be made of and/or include any electrically conductive, semiconductive or insulative material when the electric voltage is to be applied thereacross, and the like. The support serves to mechanically support the above body and/or retain such a body therein for mechanical protection and/or electrical isolation. The insert is typically used to augment amplitudes of the counter waves, particularly when the counter unit includes at least one coil of conductive wire into which such an insert is disposed. The insert may be made of and/or include various magnetic materials such as, e.g., ferromagnetic materials, paramagnetic materials, diamagnetic materials, and ferrimagnetic materials, where the ferromagnetic materials are the preferred ones. It is appreciated that the counter unit is generally arranged to maintain its configuration while emitting such counter waves, where this fixed configuration may be embodied by forming the body of the counter unit of rigid materials, by fixedly coupling the body of the counter unit to the support, and so on. In the alternative, the counter unit may be arranged to change its shape while emitting such counter waves, where this variable configuration may be embodied by forming the body of the counter unit of elastic or deformable materials, by movably coupling the body of the counter unit to the support, and the like. It is appreciated that the counter unit emitting such counter waves is to be opposed by the base unit irradiating the harmful waves of an opposite magnetic polarity. Accordingly, such a counter unit tends to move while emitting the counter waves and a special provision may have to be implemented when it is desirable to fix the counter unit during its operation.

The counter may be provided in various configurations which typically refer to shapes, sizes, arrangements, and the like. In general, the configuration of the counter unit depends upon the above countering modes (such as the source matching and wave matching) and/or countering mechanisms (such as the front, rear or lateral arrangement, local or global matching, and the like) which generally depend on the configurational characteristics of the base units, wave characteristics of the harmful waves, and the like. In addition, the configuration of the counter unit also depends upon the shapes, sizes, orientation, and/or dispositions of the target spaces which are to be formed on one side of the counter unit.

The shape of the counter unit may be arranged to be identical to or similar to the shape of the base unit, where such a counter unit is to be constructed to emit the counter waves which match the harmful waves automatically. The shape of the counter unit may instead be arranged to be different from the shape of the base unit, where such a counter unit may be provided in other shapes, may be wound around the base unit, may enclose at least a portion of the base unit therein, may be enclosed by at least a portion of the base unit, and the like. Such a counter unit may define a shape of a wire, a strip, a sheet, a tube, a coil, a spiral, and/or a mesh, may define a combination of two or more of such shapes without defining any holes or openings therethrough, may define an array of two of more of such shapes while defining multiple holes and/or openings therethrough, and the like, where examples of the combinations and/or arrays may include, but not be limited to, a bundle including multiple identical or different shapes bundling each other, a braid of multiple identical or different shapes braided along each other, and the like. The counter unit may also be made of a mixture which includes at least two materials and which are also provided in any of the above shapes, combinations, and/or arrays. It is appreciated that the coil (including a solenoid or a toroid), the spiral, the mesh, and the arrays thereof may be particularly useful in the wave matching as will be described below. It is also appreciated that all of multiple counter units may define the same shape or that at least two but not all of such counter units may define the same shape. Alternatively, all of such counter units may define different shapes.

The counter unit may be shaped to conform to the base unit so that the counter waves by the counter unit better match the harmful waves, where such a counter unit may be conformed to such a base unit while approximating the base unit or providing further details to the base unit. Alternatively, the counter unit may be shaped to not conform to the base unit while manipulating the counter waves to match the harmful waves. This arrangement may be embodied when a single counter unit counters multiple base units or when multiple counter units counter a single base unit. It is appreciated in such an arrangement that the counter unit(s) may be provided with proper electrical energy (e.g., current or voltage) for emitting the counter waves capable of matching and countering the harmful waves in the target space. It is also appreciated that all of multiple counter units may conform to the base unit(s) or that at least two but not all of the counter units may conform to the base unit(s). In the alternative, all of the counter units may not conform to the base unit(s).

When one or multiple counter units are shaped similar or identical to one or multiple base units, the counter units are preferably arranged to approximate the base units. When the base unit forms a three-dimensional (or 3-D) shape, the counter unit may be constructed as a three-dimensional analog with a similar shape or simpler shape, a two-dimensional (or 2-D) analog or an one-dimensional (or 1-D) analog. When the base unit defines a 2-D shape, the counter unit may be fabricated as a 2-D of a similar or simpler shape or 1-D analog. When the base unit forms an 1-D shape, the counter unit may be provided as another 1-D analog defining a similar or simpler shape. When a single counter unit has to counter multiple base units, the counter unit may approximate only a major base unit as one of such analogs, may approximate at least two of such base units into one of the analogs, and the like. When multiple counter units counter a single base unit, each counter unit may approximate only a portion of the base unit. When multiple counter units are to counter multiple counter units, the counter units may approximate the base units into the analogs of the same dimension or into various analogs provided in different dimensions. It is appreciated that those analogs conform to the base units and, accordingly, that the analogs may define rather straight or curved shapes depending upon the shapes of the base units. It is also appreciated that the analogs preferably maintain similarity with the base units, where such similarity may be maintained in terms of lengths of such counter and base units, widths thereof, heights thereof, thicknesses thereof, diameters or radii thereof, radii of curvature thereof, numbers of revolutions or turns thereof, ratios of such lengths, ratios of such widths, ratios of such thicknesses or heights, ratios of such diameters or radii, ratios of such numbers, and the like. When a single base unit is countered by a single counter units, such configurational parameters are defined in each of the base and counter units. When a single counter unit counters multiple base units, such configurational parameters are defined in the counter unit, in an array of all of such base units, in an array of at least two but not all of such base units, and the like. When multiple counter units counter a single base unit, such configurational parameters are defined in the base unit, in an array of all of such counter units, in an array of at least two but not all of such counter units, and the like. When multiple counter units counter the same or different number of base units, such configurational parameters are also defined individually or in arrays as described above.

When the single or multiple counter units are shaped similar or identical to the single or multiple base units, the counter units are instead arranged to provide details to the base units, not in a sense of adding structures not existing in the base units but in a context of streamlining the wavefronts of the counter waves for the better purpose of matching the wavefronts of such counter waves with those of the harmful waves. For example, one or multiple small counter units may be disposed around (or inside) one or more major counter units for manipulating outer (or inner) edges of the wavefronts of a sum of the counter waves emitted by the major counter units. In another example, one or multiple small counter units may also be disposed closer to (or away from) one or more major counter units to manipulate the radii of curvature of the wavefronts of a sum of the counter waves which are emitted by the major counter units. Such small or minor counter units may be incorporated in various relations with respect to one or more major counter units for other purposes as well, as far as incorporation of such minor counter units may improve matching between the counter and harmful waves in the target space. Accordingly, when the system includes multiple counter units, all of the counter units may be arranged to approximate the base unit(s), all of such counter units may be arranged to provide details to the base unit(s), or some but not all of the counter units may approximate the base unit(s).

The counter unit may be arranged to define various cross-sections along a longitudinal or long axis thereof, its short axis which may be perpendicular or otherwise transverse to the long axis, and the like. In one example, the counter unit is arranged to define an uniform cross-section along at least one of such axes so that the counter waves emitted thereby also define the wavefronts defining the same shapes along such axes. In another example, the counter unit may be constructed to change its cross-section along at least one of such axes so that the counter waves emitted thereby also define the wavefronts varying their shapes along at least one of such axes. When the system has multiple counter units, all of such units may define the same shape or at least two of such counter units may define different shapes.

The counter unit may be arranged to have various sizes, where such a counter unit may emit the counter waves of proper amplitudes capable of effectively countering the harmful waves thereby. For example, the counter unit incorporated in the front arrangement may define a smaller size than the base unit due to its closer disposition toward the target space, whereas the counter unit incorporated in the rear arrangement may define a larger size than the base unit due to a greater distance toward the target space. However, the size of the counter unit may be determined by other factors such as, e.g., the shape of the counter unit, amplitudes of electric energy (i.e., electric current and/or voltage) supplied thereto, and the like. Therefore, the counter unit in the front arrangement may define a larger size than the base unit while emitting a less amount of the counter waves per an unit area, whereas the counter unit in the rear arrangement may define a smaller size than the base unit while emitting a greater amount of the counter waves per an unit area, and so on. That is, the size of the counter unit may be deemed as a secondary parameter which may be determined by other factors such as, e.g., the shape of the counter unit, amplitudes of the electric energy supplied thereto, distances to the base unit and/or target space, arrangement of the counter unit(s), orientation thereof, and the like.

The counter unit may be arranged to have various sizes along its longitudinal axis and/or short axis. In one example, the counter unit is arranged to define an uniform size along at least one of such axes so that the counter waves emitted thereby also define the wavefronts defining the same shapes along such axes, assuming that the same amount of the electric energy is supplied thereto. In another example, the counter unit may be constructed to change its size along at least one of the axes so that the counter waves emitted thereby also define the wavefronts varying their shapes along such axes. In addition, the counter unit may maintain the same size along at least one of such axes while varying its shapes therealong. When the system includes multiple counter units, such counter units may have the same size or at least two of such units may define different sizes.

Multiple counter units may also be incorporated in various arrangements, where such counter units are arranged to emit the counter waves capable of automatically matching such harmful waves due to the arrangement. In one example, such counter units may be incorporated into an arrangement which conform to the shape of a single base unit or conform to another arrangement of multiple base units such that the counter waves match the harmful waves in the target space. In another example, the counter units may be incorporated in an arrangement which does not conform to the shape of the single base unit or does not conform to the arrangement of multiple base units. This arrangement may be embodied when multiple counter units counter a single base unit or when multiple counter units are to counter a different number of multiple base units. It is appreciated in such an arrangement that the counter unit(s) may be provided with proper electrical energy (e.g., current or voltage) for emitting the counter waves which are capable of matching and countering the harmful waves in the target space. The counter units may be disposed in an arrangement symmetric to the base unit and/or target space so that the counter waves emitted thereby also match the symmetric harmful waves. Conversely, the counter units may also be disposed in an arrangement which is asymmetric to the base unit or target space such that the asymmetric counter waves counter the asymmetric harmful waves in the target space. The single counter unit or multiple counter units may be incorporated in an arrangement which encloses therein at least a portion of one or multiple base units. Conversely, the single counter unit or multiple counter units may be incorporated in another arrangement in which at least a portion of such a counter unit(s) may be enclosed by one or multiple base units. It is appreciated that the arrangement generally connotes a pattern of multiple counter units but that such an arrangement may also mean an orientation and/or alignment of a single counter unit.

The counter may also be provided in various dispositions which generally refer to orientations, alignments, distances, mobilities, and the like. In general, such disposition of the counter unit depends on such countering modes (such as the source matching or wave matching), countering mechanisms (such as the front, rear or lateral arrangement, local or global countering, and the like), configurations of the counter unit, and the like, each of which generally depend on the configurational characteristics of the base units, wave characteristics of the harmful waves, and so on. In addition, the dispositions of the counter unit also depend upon the shapes, sizes, orientation, and/or dispositions of the target spaces defined on one side of the counter unit. It is appreciated as rules of thumb that such counter unit(s) may be typically disposed closer to the base unit(s) in the local countering mechanism and that the counter unit(s) may be disposed away from the base unit(s) in the global countering mechanism.

The counter unit may be disposed in various orientations such that the counter waves emitted thereby may be properly oriented with and counter such harmful waves. In one example, the counter unit may be disposed in an orientation defined with respect to a direction of propagation of the harmful waves, e.g., by orienting its long axis normal to the direction of such propagation. In another example, the counter unit may be disposed in another orientation which is defined with respect to a direction of the electric current or voltage, e.g., by orienting its long axis parallel to, normal to or in a preset angle with respect to the direction of the electric energy. In another example, the counter unit may instead be disposed in another orientation which is defined with respect to the longitudinal and/or short axes of the base unit. It is appreciated that such orientations of the counter unit typically depend on other configurations of the base unit, particularly when such a base unit is arranged to irradiate the harmful waves in a direction different from at least one of its axes, different from a winding direction of its coil or other parts, and the like. When the system includes multiple counter units, all of such counter units may be disposed in the same orientation, each counter unit may be disposed in a different orientation, at least two but not all of the counter units may be disposed in the same orientation, and the like.

The counter unit may be disposed in various alignments such that the counter waves emitted thereby may be properly aligned with and counter such harmful waves. In one example, the counter unit may be aligned with one or more of the above directions and/or axes, may be wound in the same direction as the base unit, and the like. In another example, the counter unit may be misaligned with at least one of the above directions and/or axes, may be wound in a direction different from that of the base unit, and the like. When the system includes multiple counter units, all of such counter units may be aligned in the same direction and/or axis, each counter unit may be aligned in a different direction or axis, at least two but not all of such counter units may be aligned in the same direction or axis, and the like. When the system includes multiple counter units, all of such counter units may be disposed in the same alignment, each counter unit may be disposed in a different alignment, at least two but not all of the counter units may be aligned in the same orientation, and the like.

The counter unit may further be disposed in a lateral alignment, an axial alignment, a concentric alignment, and the like. In the lateral alignment, one or multiple counter units may be disposed side by side with respect to the base unit or between the base units along the long and/or short axes of such base unit(s). In the axial alignment, one or multiple counter units are disposed along a direction of one or more of such axes at a preset distance(s) from such base unit(s). In the concentric alignment, one or multiple counter units may be disposed inside the single base unit, may be surrounded with multiple base units, may enclose the single or multiple base units, and the like.

The counter unit may be disposed in various distances from the base unit and/or target space. In one example, such a counter unit may be fixedly coupled to the system at a preset distance from its base unit so as to emit the counter waves with the wavefronts matching those of the harmful waves. When desirable, the counter unit may receive variable electrical energy (i.e., current or voltage) such that the amplitudes of the counter waves may vary according thereto in order to counter the harmful waves of varying amplitudes, to define different target spaces, and the like. In another example, the counter unit may be movably coupled to the system and translate or rotate between two positions so as to emit the counter waves and dispose their wavefronts in different locations with respect to the harmful waves with or without varying the amplitudes of the counter waves. Therefore, the counter unit counters the harmful waves by the counter waves with the wavefronts of which characteristics vary according to the position of the counter unit with respect to the base unit and/or target space. In another example, the system may include therein multiple counter units and manipulate wave emitting operation of each of the counter units. By properly recruiting all or some of such counter units with or without manipulating the amplitudes of the counter waves emitted therefrom, the system may counter the harmful waves while defining the target space in various locations with respect to the base unit. When the system include multiple counter units, all of such units may be fixedly incorporated therein, all of such units may be movably incorporated therein, or at least two but not all of such units may be movable incorporated therein, and the like.

The disposition of the counter unit may be assessed in terms of the distances measured along the longitudinal axis of the base unit, along the short axis thereof, around at least one of the axes, and the like. The counter unit may be disposed closer to the target space than the base unit as in the front arrangement, farther away from the target space than the base unit as in the rear arrangement, flush with the target space as in the lateral arrangement, and the like. When the system includes multiple counter units, all of such units may be disposed in the same arrangement or at least two of such units may be disposed in different arrangements. In addition, all of the counter units may be disposed at an equal distance from the base unit or, alternatively, at least two of such counter units may be disposed at different distances therefrom. It is appreciated that the counter unit is preferably disposed on the same side of the base unit with respect to the target space. When the counter unit is disposed on an opposite side of the base unit with respect to the target space, however, the counter unit may still be able to counter the harmful waves, although such a disposition may not be the preferred embodiment.

The counter unit may be incorporated into various parts of the system and disposed in various exposures as well. When the system includes the case member, the counter unit may be disposed on or over an exterior surface of the case member, on or below an interior surface of the case member, embedded into the case member, and/or inside the case member. Such a counter unit may instead be disposed on or over an exterior surface of the wave source, on or below an interior surface of such a wave source, embedded between such surfaces of the wave source, inside the wave source, and the like. The counter unit may also be disposed on or over an exterior surface of the base unit, on or below an interior surface of the base unit, embedded between such surfaces of the base unit, inside the base unit, and the like. In addition, such a counter unit may be disposed and enclosed by at least a portion of the base unit. Similarly, at least a portion or an entire portion of the counter unit may also be exposed through the system, through the case member, through the wave source, through the base unit, and the like. Moreover, the counter unit may fixedly or movably couple with one or more existing parts of the system, wave source, and/or base unit or, in the alternative, may be coupled thereto by a coupler. Similarly, the counter unit may be spaced away from or may form an unitary article with such a system, wave source, and/or base unit.

The counter unit may be made of and/or include various materials in order to emit the counter waves having proper amplitudes in response to the electric energy supplied thereto and matching the harmful waves. In one example, the counter and base units may be made of and/or include the same materials so that such units may emit the same amount of the counter and harmful waves per an unit amount of such electric energy. In another example, the counter and base units may include at least one common material and at least one different material so that such units may emit the similar but not identical amount of the counter and harmful waves per the unit amount of the electric energy. In yet another example, the counter and base units may be made of and/or include different materials so that the counter and base units emit different amounts of waves per the unit amount of the electric energy. In general, various characteristics of the counter and base units determined by their compositions may be electric resistance or conductivity, magnetic permittivity, resonance frequency, and the like. Thus, the counter unit may be arranged to define the same, similar or different conductivity, permittivity, and resonance frequency based on its composition. An entire portion of the counter unit may be arranged to have an identical composition or, alternatively, various portions of the counter unit may be arranged to have different compositions which may vary along the long or short axis thereof. When the system includes multiple counter units, all of such counter units may have the same composition, at least two but not all of the counter units may have the same composition, or all of such counter units may have different compositions, thereby also maintaining or varying the above properties therealong.

As described hereinabove, precisely matching the phase angles (either opposite or similar) of the counter and harmful waves is a prerequisite for countering the harmful waves irradiated from the base unit by the counter waves emitted by the counter unit. This phase matching may be attained by supplying proper electric energy (i.e., electric current or voltage) to such base and counter units and optionally electrically coupling such counter and base units with each other. For illustration purposes, the electric energy supplied to the base unit is to be referred to as a "source energy" hereinafter, and the electric current and voltage of the "source energy" are to be referred to as "source current" and "source voltage" hereinafter, respectively. In one example, identical source current or voltage may be supplied to the base and counter units either sequentially or simultaneously so that such phase angles of the harmful and counter waves are properly synchronized. In another example, the counter unit is supplied with only a portion of the source current or voltage sequentially or simultaneously, where the phase angles of such harmful and counter waves are still synchronized as well. In another example, the base unit is first supplied with the source current or voltage, while the system thereafter modifies the amplitudes or directions of the source current or voltage and then supplies the modified current or voltage to the counter unit. As long as the phase angles of such source energy is maintained during modification, the counter and harmful waves are properly phase synchronized. In another example, the base unit is supplied with the source energy, and the system provides an analog of such source energy and supplies the analog energy to the counter unit with or without modifying the amplitudes and/or directions thereof, where such a system may employ various electronic components, circuits, and/or controllers to provide such an analog. As long as the phase angles of the electric energy is maintained in the analog energy, the counter and harmful waves are phase synchronized as well. In another example, the counter unit is electrically coupled to the base unit in a series mode, in a parallel mode or in a hybrid mode, where the counter unit is supplied with the source energy, modified source energy or analog energy as described above and where the counter unit may be supplied with such energy sequentially or simultaneously with the base unit. When the system includes multiple counter units, all of such counter units may be supplied with the same energy, at least two but not all of such units may be supplied with the same energy, each unit may be supplied with different energy, and the like. When the system includes multiple base units which are supplied with different source energies, the single counter unit may be supplied with only one of such energies, with a combination of at least two of such energies, and the like. When the system includes multiple counter units, such units may couple with the base unit by the same or different modes, may be supplied with the same or different energies sequentially or simultaneously, and the like. It is appreciated in all of the above examples that the phase matching also depends upon other configurations and/or dispositions of the counter unit so that a direction of winding of the counter unit, orientation of the counter unit, and/or alignment thereof may have to be considered to accomplish the proper phase matching.

Further details of such source and wave matching will be provided hereinafter. As described hereinabove, it has been understood in such a source matching that there does not exist any one-to-one correlations between the configuration of such a counter unit and the configuration of the counter waves emitted thereby. That is, the counter waves of certain configuration (or wave characteristics) may be obtained by a single counter unit which defines a certain shape and size and is provided in a certain arrangement, by another counter unit which defines a similar shape and size but is provided in another arrangement, by another counter unit which has a different shape and size but is provided in a similar arrangement, by at least two counter units defining preset shapes and sizes and provided in a preset arrangement, by the same number of counter units defining different shapes and/or sizes or in a different arrangement, by a different number of counter units defining similar shapes and/or sizes or in a similar arrangement. It has also been appreciated in such a wave matching that there does not exist an one-to-one correlation between the disposition of the counter unit and the wavefronts of the counter waves emitted by the counter unit. In other words, the wavefronts with certain shapes may be obtained by a single counter unit which defines a certain configuration and is disposed in a certain position with respect to the base unit and/or target space, by another single counter unit which forms another configuration and which is disposed in another position, by at least two counter units which have preset configurations and are disposed in preset positions, by the same number of counter units defining different configurations and disposed in different positions, by a different number of counter units which define different configurations and which are disposed in different positions, and the like. However, there are a few heuristic rules which may apply not only to the source matching but also to the wave matching. The first rule is that the counter unit disposed in the front arrangement preferably defines a characteristic dimension greater than that of the base unit when other things equal so as to increase the radii of curvature of the wavefronts of the counter waves and to attain better matching between the counter and harmful waves. The second rule is the reverse of the first rule and dictates that the counter unit disposed in the rear arrangement preferably has a characteristic dimension less than that of the base unit in order to decrease the radii of curvature of the wavefronts of the counter waves and to attain better matching between the counter and harmful waves. In order to match the amplitudes of the counter and harmful waves, however, the longer or wider counter unit in the front arrangement is arranged to emit the counter waves with the amplitudes less than those of the harmful waves. Similarly, the shorter or narrower counter unit in the rear arrangement is arranged to emit the counter waves defining the amplitudes greater than those of the harmful waves. The third rule is that disposing multiple counter units emitting the counter waves of the same or similar phase angles tends to flatten the wavefronts of a sum of the counter waves and to increase the radii of curvature of the wavefronts of the counter waves. The fourth rule is the reverse of the the third rule and dictates that disposing a less number of counter units tend to sharpen such wavefronts of the sum of the counter waves and to decrease the radii of curvature of the wavefronts of the counter waves. The fifth rule is that the wavefronts of the sum of the counter waves may be sharpened and the radii of curvature of such wavefronts may be decreased when at least one but not all of multiple counter units may be arranged to emit the counter waves with the phase angles opposite to those of other counter units. It is appreciated that these rules do not generally apply to the counter units emitting the counter waves with the wavefronts defining the shapes different from the shape of the counter unit, and that those rules do not generally apply to the counter units of the non-uniform emitting power either which will be described in greater detail below.

A main purpose of the source matching is to manipulate the configuration of the counter unit to match that of the base unit such that the counter waves emitted from the counter unit better match the harmful waves irradiated from the base unit. When a system preferentially depends upon the source matching to counter the harmful waves, its counter unit may preferably be disposed within a preset or reasonable distance from the base unit, for any advantages which may be obtainable by the similarly configured counter unit may be lost otherwise. It is to be understood that the source matching is most useful when the base unit has a simple or symmetric configuration or when it is reasonable feasible to construct a replica of a complex base unit. When the system includes a single wave source including multiple base units or includes multiple waves sources each including at least one base unit, the single counter unit may be arranged to attain the source matching with multiple base units or multiple counter units may be arranged to perform the source matching with multiple base units. The source matching may include a shape matching, a size matching, an arrangement matching, a disposition matching, an intensity matching, and other configurational matching.

Some details of the shape matching have been disclosed heretofore. For example, the counter unit may be formed as a 3-D (or bulk) analog which is a replica or an approximation of one or multiple 3-D base units, may be provided as a 2-D (or planar) analog which is an approximation of a single or multiple 3-D or 2-D base units or which is a replica of a single or multiple 2-D base units, may also be formed as an 1-D (or linear) analog which is an approximation of one or multiple 3-D, 2-D or 1-D base units or which is a replica of a single or multiple 1-D base units, and the like. Similarly, multiple counter units may be constructed as 3-D analogs which are the replica or approximation of one or multiple 3-D base units, may be formed as the 2-D analogs which are the approximation of one or multiple 3-D or 2-D base units or which are the replica of a single or multiple 2-D base units, may be provided as the 1-D analogs which are the approximation of a single or multiple 3-D, 2-D or 1-D base units or which are the replica of one or multiple 1-D base units, and the like. Such analogs may have continuous shapes or shapes with multiple holes or openings, may form solid shapes or deformable shapes, may define symmetric or asymmetric shapes, and the like. The shapes of the analogs may also be determined by the foregoing countering mechanisms or, conversely, such shapes may dictate the selection of other configurations of the analogs, proper countering mechanisms adopted thereby, and the like.

The size matching may be embodied by defining the counter unit to be larger than, similar to or smaller than the base unit whether or not maintaining the similarity between the configurations of such counter and base units. Whether or not the counter unit may emit the counter waves which have the wavefronts of the similar shapes as the counter unit itself, the size of the counter unit determines an extent of dispersion or flattening of the counter waves, edge characteristics of the wavefronts, and the like. As described hereinabove, the size of the counter unit is also dictated by various countering mechanisms adopted thereby, disposition thereof, amplitudes of the electrical energy supplied thereto, and the like. Conversely, the size of the counter unit may dictate the selection of other configurations thereof, proper countering mechanisms, and the like.

The disposition matching may be embodied by manipulating the orientation of the counter unit, alignment thereof, distance to the base unit and/or target space therefrom, its mobility, and the like. As described herein, the counter unit may be oriented in the preset relations with respect to various axes and/or various directions, may be disposed in the front, rear or lateral arrangement, may be aligned or misaligned with such directions and/or axes, may be aligned or misaligned with the base unit axially, radially, angularly, concentrically, laterally, and the like. The disposition of the counter unit may also be dictated by various countering mechanisms adopted thereby, shapes and sizes thereof, amplitudes of the electrical energy supplied thereto, and the like. Conversely, the disposition of the counter unit may dictate the selection of other configurations thereof, proper countering mechanisms, and the like.

The intensity matching may be embodied by manipulating the amplitudes of the counter waves emitted by the counter unit. For example, the counter waves may define the amplitudes greater than, similar to or less than those of the harmful waves when measured at a certain distance from the base unit, when measured across the target space or at a preset position in the target space, and the like. The amplitudes of the counter waves are further dictated by various countering mechanisms adopted thereby, shapes and sizes thereof, disposition thereof, amplitudes of such electrical energy supplied thereto, and the like. Conversely, the amplitudes of the counter waves may determine the selection of other configurations thereof, proper countering mechanisms, and the like.

A main purpose of the wave matching is to dispose the counter unit along at least one of such wavefronts of the harmful waves and to emit the counter waves defining the wavefronts capable of matching and countering those of the harmful waves. When a system preferentially depends on the wave matching to counter the harmful waves, its counter unit may be disposed anywhere around the base unit in any distance as long as the counter wavefronts may match the harmful wavefronts. It is appreciated that the wave matching is most powerful when the base unit defines a rather complex or asymmetric configuration or when it is impossible to construct a replica or approximation of a complex base unit. When such a system includes a single wave source having multiple base units or includes multiple waves sources each including at least one base unit, the single counter unit may be arranged to attain the wave matching with multiple base units or multiple counter units may instead be arranged to perform the wave matching with multiple base units. The only one disadvantage or complication as to the wave matching is that detailed shapes and distribution of the wavefronts of the harmful waves have to be assessed a prior.

In one type of the wave matching, the counter waves are emitted by at least one counter unit defining an uniform emitting capacity in which amplitudes per an unit configuration of the counter unit such as, e.g., its length, its width, its radius or diameter, its area, and/or its weight is maintained to be uniform thereacross. Therefore, such a counter unit emits the counter waves having the wavefronts which are similarly shaped as the counter unit itself and, when disposed along the wavefront of the harmful waves, counters the counter waves while defining the target space. In another type of the wave matching, such counter waves are emitted by another counter unit with a non-uniform emitting capacity in which amplitudes per the unit configuration of the counter unit vary thereacross. In such an arrangement, the counter unit emits the counter waves of the wavefronts which are not similar to the shape of the counter unit. Therefore, the counter unit of this non-uniform capacity are disposed not along a single wavefront of the harmful waves but across at least two of such wavefronts so as to emit the counter waves capable of matching the harmful waves and defining the target space.

It is appreciated that the counter units with the uniform emitting capacity may also be disposed along at least two wavefronts of the harmful waves as exemplified in FIG. 2E. When multiple counter units are disposed in different wavefronts of the harmful waves, such units may also be arranged to emit the counter waves of different amplitudes in order to compensate discrepancies in the distances to the base unit therefrom. Such compensation may be attained by various means, e.g., by adjusting the shapes and sizes of the counter units, by manipulating the amount of the electric energy supplied thereto, by controlling the orientations and/or alignments of such counter units, and the like. As far as a sum of the counter waves defines the wavefronts which match those of the harmful waves in the target space, such counter units may be disposed along adjacent or space-apart wavefronts of the harmful waves in various configurations and/or dispositions.

Similar to their counterparts in the case of the source matching, the counter unit for the wave matching may similarly define a shape of a wire, a strip, a sheet, a tube, a coil, a spiral, and/or a mesh, may also define a combination of two or more of such shapes without defining any holes or openings therethrough, may define an array of two of more of such shapes while defining multiple holes and/or openings therethrough, and so on, where examples of such combinations and/or arrays may include, but not be limited to, a bundle of multiple identical or different shapes bundling each other, a braid of multiple identical or different shapes braided along each other, and the like. Such a counter unit may then be disposed along the single or multiple wavefronts of the harmful waves.

The EMC systems of the present invention are specifically intended to counter various harmful waves in a carrier frequency range or an extremely low frequency range from about 50 Hz to about 60 Hz or another frequency range of less than about 300 Hz. Therefore, in the preferred embodiment of this invention, various counter units of the EMC systems are arranged to emit the counter waves in the carrier frequency range or extremely low frequency range of from about 50 Hz to about 60 Hz or another frequency range of less than about 30 Hz, thereby effectively countering the harmful waves in the comparable frequency ranges. Considering various medical findings and/or presumptions that a main culprit of the EM waves are those in these frequency ranges, these counter units are believed to effectively eliminate those harmful frequency components from the harmful waves irradiated from the base units of various electric and electronic devices.

Although not preferred, various counter units of the EMC systems of the present invention may also be arranged to emit the counter waves in an ultra low frequency range of less than about 3 kHz, the counter waves in a very low frequency range of less than about 30 kHz, and the counter waves in a low frequency range of less than about 300 kHz for countering those harmful waves in the same or similar frequency ranges. The counter units may also be arranged emit the counter waves in other frequency ranges such as, e.g., the radio waves of frequencies which range from about $5 \times 10^2$ Hz to about $10^8$ Hz, microwaves of frequencies which range from about $10^8$ Hz to about $10^{12}$ Hz, and so on, in order to counter the harmful waves of similar frequency ranges. When desirable, the counter units may also be arranged to emit the counter waves defining higher frequencies such as, e.g., ultraviolet rays of frequencies ranging from about $7.5 \times 10^{14}$ Hz to about $10^{17}$ Hz, X-rays of frequencies ranging from about $7 \times 10^{16}$ Hz to about $10^{19}$ Hz, gamma rays in a frequency range beyond $5 \times 10^{18}$ Hz, and the like, for countering the harmful waves of similar frequency ranges.

Such counter units may further be arranged to selectively counter specific components of the harmful waves or, alternatively, to specifically preserve specific components of such harmful waves while countering (i.e., canceling and/or suppressing) the rest of the harmful waves. For example and particularly when the harmful waves include higher frequency components, the counter units may be specifically arranged to preserve beneficial waves such as, e.g., infrared rays including far infrared rays in a frequency range from about 300 gHz to about 10 tHz, medium infrared rays in a frequency range from about 10 tHz to about 100 tHz, near infrared rays in a frequency range from about 100 tHz to about 700 tHz, and the like, while countering the rest of the harmful waves including those of the carrier frequency range and extremely low frequency ranges. Conversely, the counter units may be arranged to emit the infrared rays including such far-, medium-, and/or near-infrared rays as well.

In another aspect of the present invention, various counter units may also be implemented into the base units of various devices and convert such devices to the EMC systems in which the harmful device EM waves irradiated by their base units may be countered (i.e., canceled and/or suppressed) by the counter waves emitted by their counter units.

In one exemplary embodiment of this aspect of the present invention, the counter units may be implemented into any base units shaped as electrically conductive wires, strips, sheets, tubes, coils, spirals, and/or meshes or, in the alternative, to any electrically semiconductive and/or insulative wires, strips, sheets, tubes, coils, spirals, and/or meshes for minimizing the irradiation of the harmful waves by countering such harmful waves by the counter waves, e.g., by canceling at least a portion of the harmful waves in the target space and/or suppressing the harmful waves from propagating to such a target space. Such counter units may be made of and/or include at least one material which may then be electrically conductive, insulative or semiconductive. The counter units may be implemented to any of the base units which have the shapes formed by one or multiple wires, strips, sheets, tubes, coils, spirals, and/or meshes, by modifying the shapes of one or multiple wires, strips, sheets, tubes, coils, spirals, and/or meshes, where a few examples of the modified shapes may be a solenoid and a toroid each formed by modifying the shape of the coil. In general, the counter units of this embodiment may be disposed in any of the foregoing arrangements and may counter the harmful waves by any of the foregoing mechanisms. Accordingly, a similarly or identically shaped and/or sized counter unit may be disposed lateral or side by side to one or more base units, may be axially, radially or angularly aligned with one or more base units, may enclose therein one or more base units, may be enclosed by one or more base units, may wind around one or more base units, may be wound by one or more base units, and the like, based on the source matching. In the alternative, a similarly or differently shaped and/or sized counter unit may be disposed along one or more wavefronts of the harmful waves irradiated by one or more base units for the wave matching. In addition, such counter units may be employed in a proper number and/or arrangement to counter the harmful waves according to the local countering or global countering.

In another exemplary embodiment of this aspect of the present invention, the counter units may also be implemented into any conventional electric and/or electronic elements such as, e.g., resistors, inductors, capacitors, diodes, transistors, amplifiers, and other signal processors and/or regulators in order to counter the harmful waves which are irradiated by the elements, where such electric and/or electronic elements function to manipulate at least one input signal supplied thereto and to produce at least one output signal at least partially different from the input signal. All of the above electric and/or electronic elements may qualify as the base units within the scope of the present invention when the unsteady current flows therein or when the unsteady voltage is applied thereacross. In addition, the above elements may also qualify as the base units within the scope of this invention when any of the elements produces the unsteady output signal (i.e., the electric current or voltage) in response to the input signal which may be steady or unsteady. Therefore, any of the above prior art elements and/or devices including such elements may be converted into the EMC elements by incorporating thereinto various counter units having any of the above configurations in any of the above dispositions and/or arrangements, thereby countering the harmful waves in any of the above mechanisms. It is noted that such counter units may be provided in any dimension so that such EMC elements may be provided in a range of microns or nanometers.

In another exemplary embodiment of this aspect of the invention, the counter units may also be incorporated into various speakers to counter the harmful waves irradiated by their base units, where examples of the speakers may include, but not limited to, cone-drive speakers, electrostatic speakers, and piezoelectric speakers. Therefore, any conventional devices including these EMC speakers such as earphones, headphones, wired phones, mobile phones, and audiovisual devices may be converted into various EMC systems such as EMC earphones, EMC headphones, EMC wired phones, EMC mobile phones, and EMC audiovisual systems. FIGS. 3A to 3I are schematic perspective views of exemplary counter units implemented to speakers including various base units according to the present invention, where FIGS. 3A to 3D exemplify various counter units implemented into prior art cone-drive speakers and countering their base units, while FIGS. 3E to 3I represent various counter units implemented into conventional piezoelectric speakers and countering their base units. It is to be understood in FIGS. 3A to 3D that permanent magnets disposed around or inside speaker cones are omitted in the figures for simplicity of illustration or, in the alternative, that the cone-drive speakers are the magnetless speaker systems disclosed in the co-pending Application of U.S. Ser. No. 60/815,826 entitled "Electromagnetically-Countered Speaker Systems and Methods." It is to be similarly understood in FIGS. 3E to 3I that only piezoelectric plate and electrodes are selected as representative base units of prior art piezoelectric speakers. It is therefore appreciated that other conductive, semiconductive, and/or insulative parts of such speakers which may emit the harmful waves are to be omitted from all of these figures and that, when necessary, such parts may be properly countered by resorting to any of such counter units as described above. It is also appreciated in FIGS. 3A to 3I that various speakers and their counter units are disposed in order to define the target spaces on top of each figures.

Figure 3A:
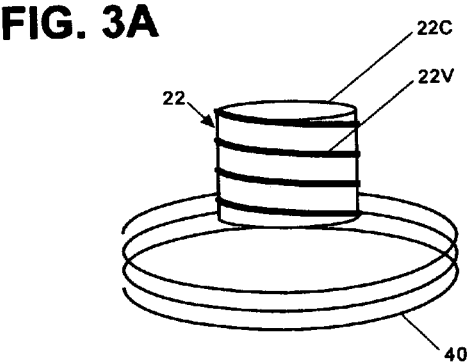
FIGS. 3A to 3I are schematic perspective views of exemplary counter units incorporated into speakers including various base units according to the present invention.

In one example of FIG. 3A, a cone-drive speaker 22 typically includes a cone 22C and at least one voice coil 22V wound around the cone 22C. As well known in the art, the voice coil 22V defines dynamic magnetic fields therearound when supplied with source current, and interaction between the dynamic magnetic fields of the voice coil 22C and static magnetic fields formed by permanent magnets (not included in this figure) vibrates the cone 22C while generating audible sounds in response to the source current. In order to counter the harmful waves irradiated by the voice coil 22V (i.e., the base unit of this speaker 22), at least one counter unit 40 is disposed according to a preset relation to the voice coil 22V. In this example, the counter unit 40 is formed as another coil defining a greater radius of curvature than the voice coil 22V. In this context, this counter unit 40 is to preferentially operate in the mode of the source matching, more particularly, the shape matching. In addition, the counter unit 40 is disposed below the target space and voice coil 22V in the rear arrangement so that the counter unit preferably emits such counter waves of amplitudes greater than those of the harmful waves due to a greater distance to the target space than the voice coil 22V. The counter unit 40 is further aligned with a longitudinal axis of the voice coil 22V so that centers of the wavefronts of the counter waves coincide with those of the wavefronts of the harmful waves. In order to ensure such counter waves to have the phase angles at least partially opposite to those of the harmful waves, the source current or an analog thereof may be supplied to the counter unit 40 in a direction which is identical or opposite to that of the source current flowing in the voice coil 22V depending on a winding direction of the wire in the counter unit 40. Accordingly, the counter unit 40 may emit the counter waves which are aligned with the harmful waves and which define the phase angles opposite to those of such harmful waves, thereby matching and countering the harmful waves in the target space. As mentioned above, such a counter unit 40 may be viewed as a 3-D analog of the voice coil 22V which defines the shape similar to that of the voice coil 22V but a configuration larger or wider than that of the voice coil 22V. When desirable, the counter unit 40 may be disposed at a preset distance from the voice coil 22V in which the wavefronts of the counter waves from the counter unit 40 may match those of the harmful waves from the voice coil 22V as have been mentioned in the wave matching. In all of these examples, such a speaker 22 is converted into the EMC speaker system of this invention by the counter unit 40.

The above counter unit 40 may be modified into other configurations, may be implemented into other dispositions, and/or may counter the harmful waves in other mechanisms. For example, such a counter unit may have a different radius of curvature which may be smaller than that of the voice coil, which may be constant or may change along its longitudinal axis, and the like. In another example, the counter unit may be disposed in the front arrangement while defining a radius of curvature which may be greater than, similar to or less than that of the voice coil. In another example, two or more similarly or differently shaped counter units may be disposed in various arrangements for such local or global countering.

Figure 3B:
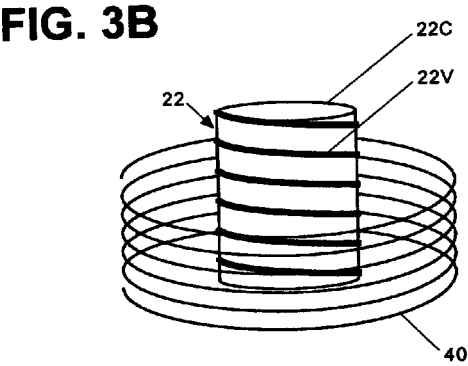

In another example of FIG. 3B, a cone-drive speaker 22 also includes a cone 22C and at least one voice coil 22V wound around the cone 22C. In order to counter the harmful waves irradiated by the voice coil 22V, at least one counter unit 40 is shaped similar to the voice coil 22V and is disposed according to a preset relation to the voice coil 22V. In this example, this counter unit 40 is to operate based on the source matching, more particularly, the shape matching. In addition, the counter unit 40 is disposed around at least a portion of the voice coil 22V in the lateral and concentric arrangements so that the counter unit preferably emits the counter waves of the amplitudes similar to or slightly less than those of the harmful waves due to a similar or slightly greater distance to the target space than the voice coil 22V. The counter unit 40 is also aligned with the longitudinal axis of the voice coil 22V such that centers of the wavefronts of the counter waves align with those of the wavefronts of the harmful waves. The source current or an analog thereof may also be supplied to the counter unit 40 in a direction which is identical or opposite to that of the source current flowing in the voice coil 22V based on a winding direction of the wire in the counter unit 40 in order to ensure the counter waves to define the phase angles at least partially opposite to those of the harmful waves. Accordingly, the counter unit 40 emits the counter waves which are aligned with the harmful waves and define such phase angles opposite to those of the harmful waves, thereby matching and countering the harmful waves in the target space. When desirable, the counter unit 40 may be disposed at a preset radial or axial distance from the voice coil 22V in which the wavefronts of the counter waves from the counter unit 40 may match those of the harmful waves from the voice coil 22V as have been mentioned in the wave matching. In all of these examples, the speak 22 is converted into such an EMC speaker system of this invention by the counter unit 40. Other configurational and/or operational characteristics of the counter unit 40 of FIG. 3B are similar or identical to those of the counter unit of FIG. 3A.

The above counter unit 40 may be modified into other configurations, may be implemented into other dispositions, and/or may counter the harmful waves in other mechanisms. For example, such a counter unit may have a different radius of curvature which may be smaller than that of the voice coil and may be disposed inside the cone, which may be constant or may vary along its longitudinal axis, and the like. In another example, such a counter unit may be disposed to enclose a different portion of the voice coil or to enclose an entire portion thereof while defining a radius of curvature greater than, similar to or less than that of the voice coil. In another example, multiple similarly or differently shaped counter units may be disposed in various arrangements for such local or global countering. It is to be understood in FIGS. 3A and 3B that the voice coils and counter units may be replaced by each other. That is, each figure may be interpreted such that an outer coil represents the larger voice coil and that an inner coil is a counter unit which is enclosed by the outer voice coil, where other features of FIGS. 3A and 3B also apply thereto.

Figure 3C:
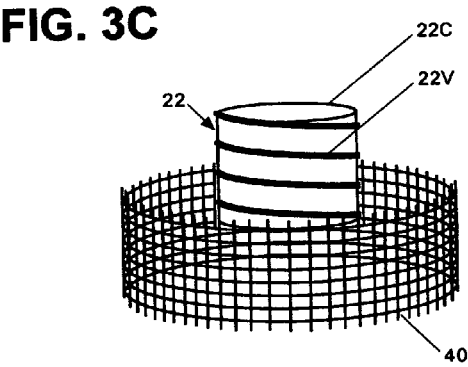

In another example of FIG. 3C, a cone-drive speaker 22 also includes a cone 22C and at least one voice coil 22V wound around the cone 22C. In order to counter the harmful waves irradiated by the voice coil 22V, a counter unit 40 is made of a mesh having multiple openings therein and wrapped into an annular tube in an arrangement similar to that of the voice coil 22V. The counter unit 40 is then disposed around at least a portion of the voice coil 22V in the lateral and concentric arrangements so that the counter unit 40 emits the counter waves of the amplitudes similar to or slightly less than those of the harmful waves due to a similar or slightly greater distance to the target space than the voice coil 22V. The counter unit 40 is further aligned with the longitudinal axis of the voice coil 22V so that centers of the wavefronts of the counter waves align with those of the wavefronts of such harmful waves. The source current or an analog thereof may be supplied to the counter unit 40 in a direction which ensures the counter waves to have the phase angles at least partially opposite to those of the harmful waves. Accordingly, the counter unit 40 emits the counter waves which are aligned with the harmful waves and have the phase angles opposite to those of the harmful waves, thereby matching and countering such harmful waves in the target space. When desirable, the counter unit 40 may be disposed at a preset radial or axial distance from the voice coil 22V in which the wavefronts of such counter waves by the counter unit 40 may match those of the harmful waves from the voice coil 22V as described in the wave matching. In all of these examples, the speak 22 is converted into the EMC speaker system of this invention by including the counter unit 40 therein. Other configurational and/or operational characteristics of such a counter unit 40 of FIG. 3C are similar or identical to those of the counter units of FIGS. 3A and 3B.

The above counter unit 40 may be modified into other configurations, may be implemented into other dispositions, and/or may counter the harmful waves in other mechanisms. For example, such a counter unit may be formed as a solid annular tube of other shapes without any openings, an annular porous tube of other shapes, and the like. In another example, the counter unit may define a different radius of curvature which may be smaller than that of the voice coil and may be disposed in the cone, which may be constant or may vary along its longitudinal axis, and the like. In another example, such a counter unit may be disposed to enclose a different portion of the voice coil or to enclose an entire portion thereof while having a radius of curvature greater than, similar to or less than that of the voice coil. In another example, multiple similarly or differently shaped counter units may also be disposed in various arrangements for such local or global countering.

Figure 3D:
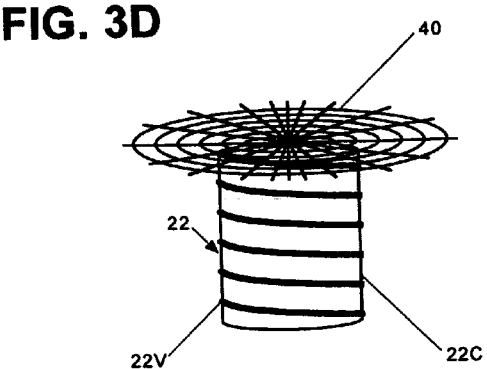

In another example of FIG. 3D, a cone-drive speaker 22 also includes a cone 22C and at least one voice coil 22V wound around the cone 22C. In order to counter the harmful waves irradiated by the voice coil 22V, a counter unit 40 is provided as a sheet of a mesh having multiple openings therein. This counter unit 40, however, is made of a mesh which is slightly different from that of FIG. 3C. For example, the mesh of FIG. 3D defines multiple openings formed between concentric and radial wires of the counter unit 40, while the mesh of FIG. 3C defines multiple openings formed between horizontal and vertical wires of its counter unit. Such a counter unit 40 is disposed over the voice coil 22V in the front arrangement so that the counter unit 40 emits the counter waves of amplitudes less than those of the harmful waves due to a shorter distance to the target space than the voice coil 22V. A center of the counter unit 40 is also aligned with the longitudinal axis of the voice coil 22V so that centers of the wavefronts of the counter waves align with those of the wavefronts of the harmful waves. The source current or its analog may also be supplied to the counter unit 40 in a direction which ensures the counter waves to have the phase angles at least partially opposite to those of the harmful waves. Accordingly, the counter unit 40 emits the counter waves which are aligned with the harmful waves and have the phase angles opposite to those of the harmful waves, thereby matching and countering such harmful waves in the target space. When desirable, the counter unit 40 may also be disposed at a preset radial or axial distance from the voice coil 22V, where the wavefronts of the counter waves by the counter unit 40 may match those of the harmful waves from the voice coil 22V as described in the wave matching. In all of these examples, the speak 22 is converted into the EMC speaker system of this invention by including such a counter unit 40 therein. Further configurational and/or operational characteristics of such a counter unit 40 of FIG. 3D are similar or identical to those of the counter units of FIGS. 3A to 3C.

The above counter unit 40 may be modified into other configurations, may be implemented into other dispositions, and/or may counter the harmful waves in other mechanisms. For example, such a counter unit may be formed as a solid sheet of other shapes without any openings, a porous sheet of other shapes, and the like. More particularly, the counter unit may further be contoured to be concave upward (or downward) for better matching the wavefronts of such counter waves with those of the harmful waves. In another example, the counter unit may be disposed at a different distance from the base unit, may be disposed over a different portion of the voice coil, and the like. In another example, multiple similarly or differently shaped counter units may also be disposed in various arrangements for such local or global countering.

In another example of FIG. 3E, a piezoelectric speaker 22 includes a piezoelectric plate 22P, a pair of electrodes 22E, and a metal plate 22M, where each of the electrodes 22E is fixedly coupled to each of opposite sides of the piezoelectric plate 22P (to be referred to as a "piezo plate" hereinafter), while the metal plate is fixedly attached to one of such electrodes 22E. As well known in the art, the piezo plate 22P is arranged to vibrate when alternating source voltage is applied thereacross by such electrodes 22E, where the metal plate 22M mechanically supports the piezo plate 22P and electrodes 22E but is generally arranged not to vibrate with the piezo plate 22P, where an assembly of the piezo plate 22P and electrodes 22E are frequently referred to as a "piezoelectric element." Accordingly, the piezoelectric speaker 22 generates audible sounds in response to the source voltage while irradiating the harmful waves by its base units 22P, 22E in the piezoelectric element. The metal plate 22M may be included in the base unit as well depending on whether or not the metal plate 22M may affect paths of the harmful waves therealong. In order to counter the harmful waves irradiated from such base units, at least one counter unit 40 is preferably disposed in a preset relation to various base units 22P, 22E of the piezoelectric speaker 22. In this example, the counter unit 40 is provided as a 3-D replica of the the base units 22P, 22E which similarly includes a piezo plate, two electrodes attached to the sides of the piezo plate, and a metal plate. In this context, this counter unit 40 is to preferentially operate on the source matching or, more specifically, the shape matching. In order to prevent such a counter unit 40 from generating any audible sounds, however, the piezo plate of this counter unit 40 may be fixedly coupled to a metal plate thereof or otherwise arranged to not vibrate in response to source voltage or an analog thereof supplied thereto. In addition, the counter unit 40 is disposed below the piezoelectric speaker 22 in the rear arrangement such that the counter unit 40 preferably emits the counter waves of amplitudes greater than those of such harmful waves due to a greater distance to the target space than the base units 22P, 22E. The counter unit 40 is aligned with a longitudinal axis of the speaker 22 so that centers of the wavefronts of the counter waves coincide with those of the wavefronts of the harmful waves. To ensure such counter waves to define the phase angles at least partially opposite to those of the harmful waves, the source current or its analog may be supplied to the counter unit 40 in a direction opposite to that of the source current flowing in the speaker 22. Therefore, the counter unit 40 may emit the counter waves which are aligned with the harmful waves and which define the phase angles opposite to those of such harmful waves, thereby matching and countering the harmful waves in the target space. As mentioned above, the counter unit 40 may be viewed as a 3-D analog of the piezoelectric speaker 22 defining the similar shape but a configuration larger or thicker than that of the speaker 22. When desirable, the counter unit 40 may be disposed at a preset distance from the speaker 22 in which the wavefronts of the counter waves from the counter unit 40 may match those of the harmful waves from the speaker 22 as have been mentioned in the wave matching. In all of the examples, the speaker 22 is converted into the EMC speaker system of this invention by including the counter unit 40 therein.

The above counter unit 40 may be modified into other configurations, may be implemented into other dispositions, and/or may counter the harmful waves in other mechanisms. For example, such a counter unit may have a different radius and/or height while maintaining an aspect ratio of the speaker or varying such a ratio. In another example, such a counter unit may have a shape defining the similar aspect ratio but include the plates and electrodes of thicknesses which are different from those of the speaker. In another example, the counter unit may also be disposed in the front arrangement in which an upper article of the figure may be viewed as the counter unit and a lower article may be interpreted as the speaker. In another example, two or more similarly or differently shaped counter units may be disposed in various arrangements for the local or global countering. It is appreciated that the counter unit may have the shape similar to that of the piezoelectric speaker but may be made of and/or include different materials. For example, the counter unit may have a plate made of and/or including insulative or semiconductive materials which are not piezoelectric but define an electric resistivity similar to that of the piezo plate of the speaker. In another example, the electrodes and/or metal plate may be made of and/or include materials different from those of the speaker but cheaper. As far as the counter unit may emit the counter waves capable of countering the harmful waves in the target space, the counter unit may define various configurations and may be made of and/or include various materials.

It is also appreciated that the counter unit itself may also operate as an additional piezoelectric speaker which is supplied with the source voltage and generate the audible sounds identical to those produced by the speaker. However, the counter unit speaker is arranged to emit the counter waves having the phase angles at least partially opposite to those of the harmful waves, thereby countering the harmful waves by the counter waves while generating the same audible sounds as the speaker. Such a counter unit may be embodied in various arrangements. For example, the speaker and counter unit may be axially or angularly aligned with each other, while the source voltage is supplied thereto in opposite directions. In another example, the source voltage may be supplied to both the speaker and counter unit in the same direction, but the counter unit is configured and/or oriented in such a manner that the counter waves define the phase angles which are opposite to those of the harmful waves. As long as the piezo plate of the counter unit vibrates in the same direction as that of the speaker and as long as the counter unit as a whole emits the counter waves matching and countering the harmful waves, the counter unit may define various configurations, may be disposed in various orientations or alignments, and/or may be supplied with the source voltage along various directions.

Figure 3E:
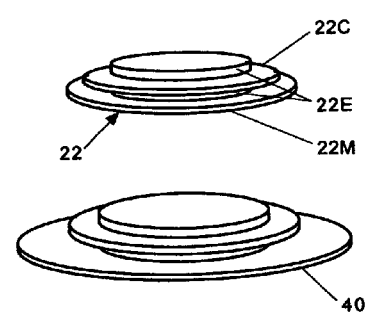
Figure 3F:
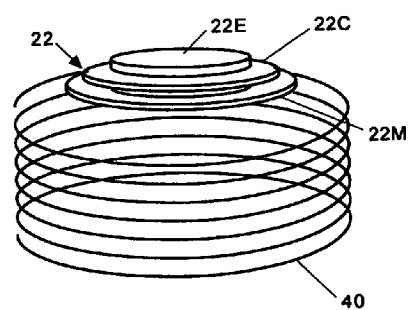

In another example of FIG. 3F, a piezoelectric speaker 22 similarly includes a piezoelectric plate 22P, a pair of electrodes 22E, and a metal plate 22M as that of FIG. 3E. In order to counter the harmful waves irradiated from such base units, at least one counter unit 40 is preferably disposed in a preset relation to the base units 22P, 22E of the speaker 22. In this example, the counter unit 40 is formed as a coil of conductive wire similar to that of FIG. 3B. In this context, such a counter unit 40 is to operate on the wave matching. The counter unit 40 is disposed below the piezoelectric speaker 22 in the rear arrangement so that the counter unit 40 emits the counter waves of amplitudes greater than those of the harmful waves due to a greater distance to the target space than the base units 22P, 22E. Such a counter unit 40 is aligned with a longitudinal axis of the speaker 22 so that centers of the wavefronts of the counter waves coincide with those of the wavefronts of the harmful waves. To ensure such counter waves to have the phase angles at least partially opposite to those of the harmful waves, the source current or its analog may be supplied to the counter unit 40 in a direction opposite to that of the source current flowing in the speaker 22. Therefore, the counter unit 40 may emit the counter waves aligned with the harmful waves and having the phase angles opposite to those of the harmful waves, thereby matching and countering the harmful waves in the target space. When desirable, the counter unit 40 is disposed at a preset distance from the speaker 22 in which the wavefronts of such counter waves by the counter unit 40 may match those of the harmful waves by the speaker 22 as have been mentioned in the wave matching. In all of the examples, the piezoelectric speaker 22 is converted into the EMC speaker system of the present invention by incorporating the counter unit 40 therein. Further configurational and/or operational characteristics of the counter unit 40 shown in FIG. 3F are similar or identical to those of the counter units of FIG. 3E.

The above counter unit 40 may be modified into other configurations, may be implemented into other dispositions, and/or may counter the harmful waves in other mechanisms. For example, such a counter unit may be disposed in a different distance from the base units or may enclose one or more of the base units therein. In another example, the counter unit may define a radius of curvature which may be smaller than that of the speaker. In another example, such a counter unit may have the radius which may be constant or may change along its longitudinal axis. In another example, multiple similar or different counter units may be disposed in various arrangements for the local or global countering.

Figure 3G:
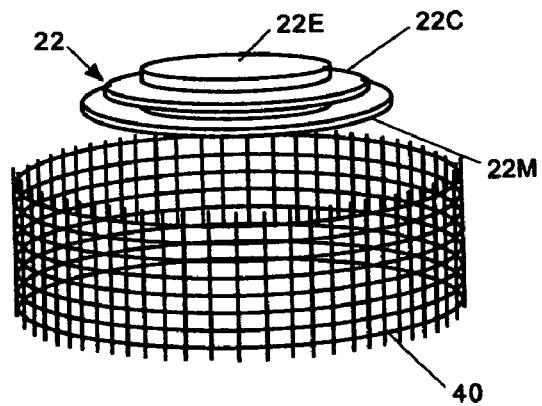

In another example of FIG. 3G, a speaker 22 similarly includes a piezoelectric plate 22P, a pair of electrodes 22E, and a metal plate 22M as that described in FIG. 3E. In order to counter the harmful waves irradiated from such base units, at least one counter unit 40 is preferably disposed in a preset relation to the base units 22P, 22E of the speaker 22. In this example, the counter unit 40 is formed as a mesh of conductive wire similar to that of FIG. 3C. In this context, the counter unit 40 is to operate on the wave matching. The counter unit 40 is disposed below the piezoelectric speaker 22 in the rear arrangement so that the counter unit 40 emits the counter waves of amplitudes greater than those of the harmful waves due to a greater distance to the target space than the base units 22P, 22E. Such a counter unit 40 is aligned with a longitudinal axis of the speaker 22 so that centers of the wavefronts of the counter waves coincide with those of the wavefronts of the harmful waves. To ensure such counter waves to have the phase angles at least partially opposite to those of the harmful waves, the source current or its analog may be supplied to the counter unit 40 in a direction opposite to that of the source current flowing in the speaker 22. Therefore, the counter unit 40 may emit the counter waves aligned with the harmful waves and having the phase angles opposite to those of the harmful waves, thereby matching and countering the harmful waves in the target space. When desirable, the counter unit 40 is disposed at a preset distance from the speaker 22 in which the wavefronts of such counter waves by the counter unit 40 may match those of the harmful waves by the speaker 22 as have been mentioned in the wave matching. In all examples, such a piezoelectric speaker 22 is converted to the EMC speaker of the present invention by the counter unit 40. Other configurational and/or operational characteristics of the counter unit 40 of FIG. 3G are similar or identical to those of the counter units of FIGS. 3E and 3F.

The above counter unit 40 may be modified into other configurations, may be implemented into other dispositions, and/or may counter the harmful waves in other mechanisms. For example, such a counter unit may be formed as a solid annular tube of other shapes without any openings, an annular porous tube of other shapes, and the like. In another example, the counter unit may define a different radius of curvature which may be smaller than those of the base units and may be disposed therein, which may be constant or may vary along its longitudinal axis, and the like. In another example, such a counter unit may be disposed to enclose therein at least a portion or entire portion of the base units while having a radius of curvature which is greater than, similar to or less than that of the base units. In another example, multiple similarly or differently shaped counter units may be disposed in various arrangements for such local or global countering.

Figure 3H:
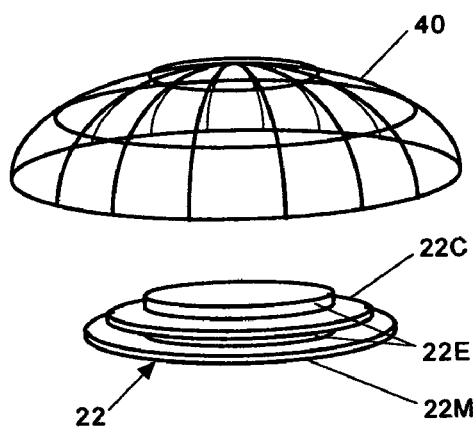

In another example of FIG. 3H, a speaker 22 similarly includes a piezoelectric plate 22P, a pair of electrodes 22E, and a metal plate 22M as that described in FIG. 3E. In order to counter the harmful waves irradiated from such base units, at least one counter unit 40 is preferably disposed in a preset relation to the base units 22P, 22E of the speaker 22. In this example, the counter unit 40 is formed as a 3-D analog of the base units 22P, 22E, where such an analog corresponds to an approximation of the base units 22P, 22E, and consists of a preset number of concentric rings of wire interconnected by another preset number of arcuate wires. In this context, such a counter unit 40 is to preferentially operate on the source matching. The counter unit 40 is disposed above the piezoelectric speaker 22 in the front arrangement so that the counter unit 40 emits the counter waves of amplitudes less than those of the harmful waves due to a shorter distance to the target space. Such a counter unit 40 is aligned with a longitudinal axis of the speaker 22 such that centers of the wavefronts of the counter waves coincide with those of the wavefronts of the harmful waves. To ensure such counter waves to have the phase angles at least partially opposite to those of the harmful waves, the source current or its analog may be supplied to such a counter unit 40 along a direction opposite to that of the source current flowing through the speaker 22. Accordingly, the counter unit 40 may emit the counter waves aligned with the harmful waves and having the phase angles opposite to those of the harmful waves, thereby matching and countering the harmful waves in the target space. In this respect, this counter unit 40 similar to that of FIG. 3D, except that this counter unit 40 defines a contour which is concave downward. When desirable, the counter unit 40 is disposed at a preset distance from the speaker 22 where the wavefronts of such counter waves by the counter unit 40 may match those of the harmful waves by the speaker 22 as have been mentioned in the wave matching. In all of the examples, such a piezoelectric speaker 22 is converted into the EMC speaker of this invention by the counter unit 40. Other configurational and/or operational characteristics of the counter unit 40 of FIG. 3H are similar or identical to those of the counter units of FIGS. 3E to 3G.

The above counter unit 40 may be modified into other configurations, may be implemented into other dispositions, and/or may counter the harmful waves in other mechanisms. For example, such a counter unit may be formed as a solid concave sheet of other shapes without any openings, a porous sheet of other shapes, and the like, in which the counter unit may include different number of rings or arcs and define the openings of different shapes. In another example, the counter unit may consists of multiple sections each of which may be supplied with the electric voltages of different amplitudes and/or directions for better approximating the base units. Such sections may be formed concentrically so that different voltages may be applied in a radial direction or, alternatively, may be formed angularly so that different voltages may be applied in an angular direction. In another example, multiple similarly or differently shaped counter units may be disposed in various arrangements for such local or global countering.

Figure 3I:
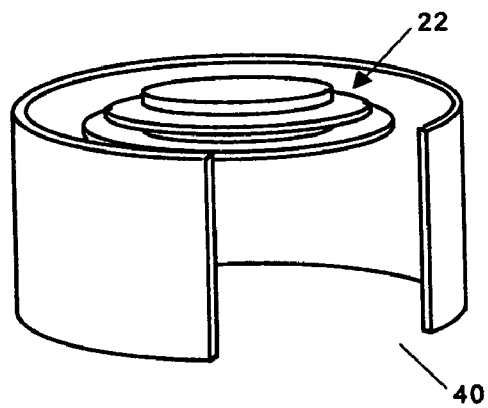

In another example of FIG. 3I, a speaker 22 similarly includes a piezoelectric plate 22P, a pair of electrodes 22E, and a metal plate 22M as that described in FIG. 3E. In order to counter such harmful waves irradiated from such base units, at least one counter unit 40 is preferably disposed in a preset relation to the base units 22P, 22E of the speaker 22. In this example, the counter unit 40 is formed as an annular tube. In this context, the counter unit 40 is to operate on the source matching. The counter unit 40 is disposed around the piezoelectric speaker 22 in the flush or concentric arrangement so that the counter unit 40 emits the counter waves defining amplitudes similar to those of the harmful waves due to a distance to the target space similar to that from the base units 22P, 22E. The counter unit 40 is aligned with a longitudinal axis of the speaker 22 so that centers of the wavefronts of the counter waves coincide with those of the wavefronts of the harmful waves. To ensure such counter waves to have the phase angles at least partially opposite to those of the harmful waves, the source current or its analog may be supplied to the counter unit 40 in a direction opposite to that of the source current flowing in the speaker 22. Accordingly, the counter unit 40 may emit the counter waves aligned with the harmful waves and defining the phase angles opposite to those of such harmful waves, thereby matching and countering the harmful waves in the target space. When desirable, the counter unit 40 is disposed at a preset distance from the speaker 22 in which the wavefronts of such counter waves by the counter unit 40 match those of the harmful waves by the speaker 22 as have been mentioned in the wave matching. In all examples, the piezoelectric speaker 22 is converted to the EMC speaker of this invention by the counter unit 40. Other configurational and/or operational characteristics of the counter unit 40 of FIG. 3G are similar or identical to those of the counter units of FIGS. 3E and 3F.

The above counter unit 40 may be modified into other configurations, may be implemented into other dispositions, and/or may counter the harmful waves in other mechanisms. For example, such a counter unit may be formed as a porous annular tube of other shapes, an annular solid tube of other shapes, and the like. In another example, the counter unit may define a different radius of curvature which may be smaller than that of the base units and disposed therein, which may be constant or may vary along its longitudinal axis, and the like. In another example, such a counter unit may be disposed to enclose therein a different portion of the base units while having a radius of curvature greater than, similar to or less than that of the base units. In another example, multiple similarly or differently shaped counter units may be disposed in various arrangements for the local or global countering. In all of the examples, the speaker 22 is converted into the EMC speaker of this invention by the counter unit 40. Other configurational and/or operational characteristics of the counter unit 40 of FIG. 3I are similar or identical to those of the counter units of FIGS. 3E and 3G.

The above counter units exemplified in FIGS. 3A to 3I as well as those described hereinabove may be disposed in any of the above arrangements and may counter the harmful waves by any of the foregoing mechanisms. Accordingly, the counter unit which may be shaped similar or identical to one or more of the base units of various speakers may be disposed lateral or side by side to one or more base units, may be axially, radially, and/or angularly aligned with one or more base units, may enclose therein one or more base units, may be enclosed by one or more base units, may wind around one or more base units, may be wound by one or more base units, and so on, when such a counter unit is to operate based on the source matching. Alternatively, the counter unit which may be shaped similar to or different from one or more of the base units may be disposed along one or more wavefronts of the harmful waves irradiated by one or more base units for the wave matching. In addition, such counter units may be employed in a proper number and/or arrangement to counter such harmful waves based on the local countering or global countering.

As described hereinabove, further details of various EMC speakers and various counter units of such EMC speakers have already been provided in various co-pending Applications one of which is entitled "Electromagnetically-Shielded Actuator Systems and Methods" and carrying a U.S. Ser. No. 11/440,135 and another of which is entitled "Electromagnetically-Countered Speaker Systems and Methods" and carrying a Ser. No. 60/815,826. Accordingly, various conventional devices with such EMC speakers can be converted into the EMC systems capable of performing their intended functions while countering such harmful waves irradiated by their motors by such counter units.

In another exemplary embodiment of this aspect of the invention, the counter units may also be incorporated into various microphones which are inverse examples of such speakers and which also have various base units which are similar to those of the speakers, where examples of the base units may include, but not be limited to, electromagnets, permanent magnets, any parts of such microphones through which the unsteady current flows, and any of such parts across which the unsteady voltage is applied. Therefore, any prior art devices which include such EMC microphones such as standalone microphones, wired phones, mobile phones, audio devices, audiovisual devices, and assemblies of an earphone and microphone may be converted into various EMC systems such as, e.g., EMC standalone microphones, EMC wired or mobile phones, EMC audio systems, EMC audiovisual systems, and such EMC assemblies, where various counter units of any of the above configurations may be incorporated thereinto in any of the above dispositions and/or arrangements and may counter the harmful waves in any of the above mechanisms.

In another exemplary embodiment of this aspect of the invention, the counter units may also be incorporated into various motors to counter such harmful waves irradiated by their base units, where such motors function to convert the electric energy into mechanical energy or electromotive force and where examples of the motors may also include, but not be limited to, DC motors, universal motors, AC synchronous motors, AC induction motors, linear or step motors, and the like. Therefore, any prior art devices (or actuators) including these EMC motors such as kitchen appliances (e.g., food processors, mixers, juicers, grinders, blenders, squeezers, dish washers, refrigerators, freezers, ice makers, can openers, food dryers, coolers, food steamers, garbage compactors, garbage disposals, and the like), cooking appliances (e.g., electric grills, electric ovens, electric stoves, electric ranges, electric toast ovens, electric toasters, their electric fans, coffee makers, espresso makers, heating bottles, and the like), household appliances (e.g., cloth washers, cloth dryers, air conditioners, garage openers, dry or wet vacuum cleaners, and the like), tools (e.g., electric drills, electric saws, electric grinders, electric screwdrivers, electric nail guns, electric staple guns, electric sanders, electric grinders, and the like), and/or personal hygiene devices (e.g., electric toothbrushes, electric razors, electric hair dryers, and the like) may all be converted into various EMC systems such as EMC kitchen appliances, EMC cooking appliances, EMC household appliances, EMC tools, EMC hygiene systems, and the like. In general, the DC motor includes at least one stator with at least one permanent magnet and at least one rotor with at least one electromagnet, the universal motor has at least one stator with at least one electromagnet and at least one rotor with at least one electromagnet, the synchronous AC motor includes therein at least one stator with at least one electromagnet and a rotor having at least one permanent magnet, an induction AC motor includes at least one stator with at least one electromagnet and at least one rotor with at least one electric conductor, a linear motor includes therein at least one stator with at least one electromagnet and at least one rotor with at least one permanent magnet, and the like. Therefore, the base units of the motors may include the rotors, stators, permanent magnets, any parts of the motors in which the unsteady current flows, any of such parts across which the unsteady voltage applies, and the like. FIGS. 4A to 4F show schematic perspective views of exemplary counter units which are implemented into motors with various base units according to the present invention, where FIGS. 4A to 4C exemplify various counter units implemented into prior art rotors of such motors, whereas FIGS. 4D to 4F describe various counter units implemented into various conventional stators of the motors. It is appreciated that detailed configurations of the stators are omitted in FIGS. 4A to 4C, while only stators are included and the matching rotors are omitted in FIGS. 4D to 4F both for simplicity of illustration. It is, accordingly, appreciated that other conductive, semiconductive, and/or insulative parts of the motors which may emit the harmful waves are to be omitted in all of these figures and that, when necessary, such parts may be properly countered by resorting to any of such counter units as described above. It is also appreciated in FIGS. 4A to 4F that various motors and their counter units are disposed so as to define the target spaces therearound, in the front of such motors (i.e., top of the figures) or in the rear thereof (i.e., bottom of the figures). It is further appreciated that details of various counter units of this embodiment have been disclosed in the co-pending Application of U.S. Ser. No. 60/818,627 entitled "Electromagnetically-Countered Actuator Systems and Methods."

Figure 4A:
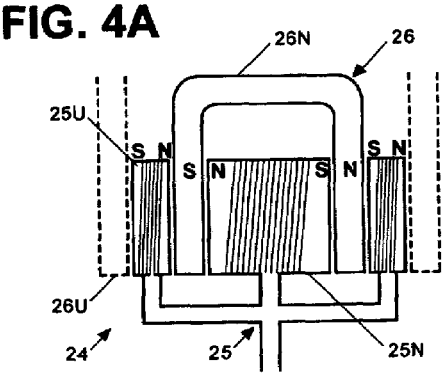
FIGS. 4A to 4F are schematic perspective views of exemplary counter units incorporated into motors including various base units according to the present invention.

In one example of FIG. 4A, a motor 24 includes a rotor unit 25 and a stator unit 26, where such a rotor unit 25 is rotatably disposed inside or enclosed by the stator unit 26. The rotor unit 25 includes a single inner base rotor 25N of an electromagnet, while the stator unit 26 includes a single inner base stator 26N of a permanent magnet. As well known in the art, such a base rotor 25N defines dynamic magnetic fields as the source current flows therein, and an interaction between the dynamic magnetic fields of the base rotor 25 and static magnetic fields of the base stator 26N rotates the rotor unit 25 in a clockwise or counterclockwise direction, while reversing the direction of the source current to the base rotor 25N to maintain rotation of the rotor unit 25 in every 180°. During its rotation, the rotor unit 25 irradiates the harmful waves as the source current flows therein, while the stator unit 26 receives and then transmits such harmful waves therethrough while affecting propagation paths of the harmful waves depending upon polarities of the harmful waves. In this context, both the rotor and stator units 25, 26 or, more specifically, the base rotor and stator 25N, 26N serve as the base units for this motor 24. In order to counter the harmful waves irradiated by the base units 25N, 26N, at least one counter unit 40 is preferably disposed in a preset relation to such base units 25N, 26N of the motor 25. In this example, the counter unit 40 includes a pair of outer counter rotors 25U and an optional outer stator 26U, where each of the counter rotors 25U is shaped as another electromagnet similar to that of the base rotor 25N and where the counter stator 26U is shaped as another permanent magnet similar to that of the base stator 26N. In this context, the counter rotors 25U operate on the source matching. More specifically, the counter rotors 25U are disposed laterally to the base rotor 25N and oriented to abut the same magnetic poles of the base rotor 25N. In addition, the counter units 25U mechanically couple with the base rotor 25N such that the above lateral arrangement and abutting orientation may be maintained during the rotation of the rotor unit 25. Therefore, the counter rotors 25U may emit such counter waves which are aligned with the harmful waves and which define the phase angles at least partially opposite to those of the harmful waves, thereby matching and countering the harmful waves in the target space. Similar to the counter rotors 25U, the counter stator 26U is disposed in the lateral and concentric arrangements to the base stator 26N and abuts the same magnetic poles of the base stator 26N. Accordingly, the counter stator 25N may emit such counter waves which are aligned with the harmful waves and which also defines the phase angles at least partially opposite to those of the harmful waves, thereby matching and countering such harmful waves in the target space. Because both of the counter rotors 25U and stator 26U counter the harmful waves irradiated by the base rotor 25N and stator 26N, this EMC motor 24 effectively minimizes irradiation of the harmful waves from the base units 25N, 26N thereof.

Figure 4D:
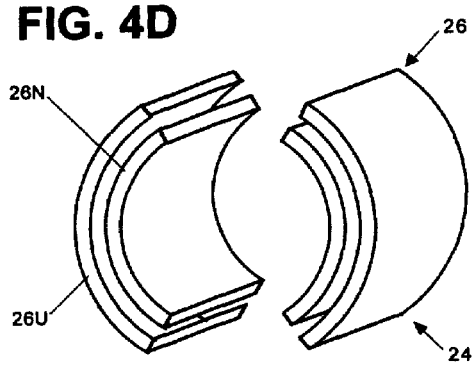
Figure 4B:
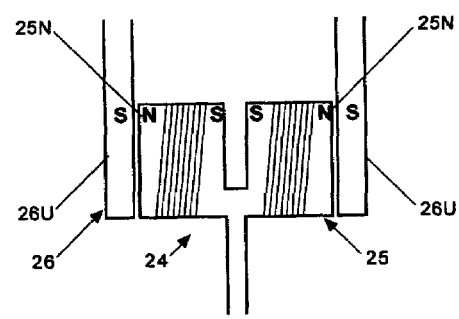

In another example of FIG. 4B, a motor 24 similarly includes a rotor unit 25 and a stator unit 26, where the rotor unit 25 is rotatably disposed inside or enclosed by the stator unit 26. The stator unit 26 includes two outer base stators 26U which are permanent magnets or electromagnets, disposed on opposite sides of the rotor unit 25, and arranged to define the same magnetic polarity. This rotor unit 25 includes a pair of inner rotors 25N of electromagnets which define the same shape and size, which are disposed symmetrically with respect to a rotation axis of the rotor unit 25, and which abut each other by the same magnetic poles. In this context, the rotor unit 25 is to operate preferentially on the source matching. These inner rotors 25N may be interpreted in various ways. For example, one of the inner rotors 25N may be deemed to serve as a base rotor, while the other of such is arranged to function as a counter rotor. Therefore, one of the rotors 25N irradiates the harmful waves, while the other thereof emits the counter waves aligned with the harmful waves, having the phase angles at least partially opposite to those of the harmful waves and, therefore, countering the harmful waves in the target space. In another example, both of such inner rotors 25N may be regarded as the base (or counter) rotors which irradiate the harmful waves but are also arranged to cooperate each other through canceling such harmful waves and/or suppressing the harmful waves irradiated by the other from propagating outwardly. The stator unit 26, which encloses such inner rotors 25N receives and transmits the harmful waves therethrough while affecting propagation paths of such harmful waves depending upon polarities of the harmful waves. When desirable, additional stator units may also be incorporated between the inner rotors 25N and/or around the outer stator 26U in order to counter the harmful waves transmitting through the outer stator 26U. Further configurational and/or operational characteristics of the motor 24 of FIG. 4B are similar or identical to those of the motor of FIG. 4A.

Figure 4E:
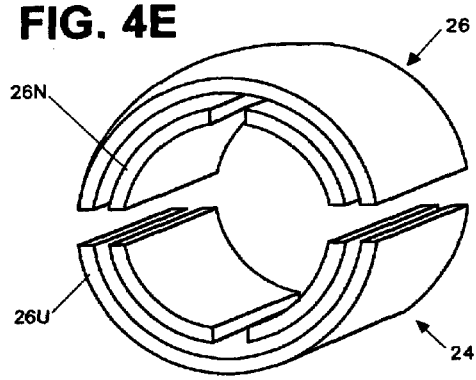
Figure 4C:
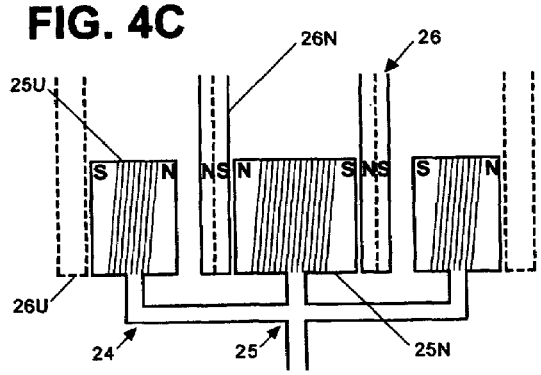

In another example of FIG. 4C, a motor 24 similarly includes a rotor unit 25 and a stator unit 26, where the rotor unit 25 is rotatably disposed inside the stator unit 26 or is enclosed thereby. Each of the rotor and stator units 25, 26 are similar to those of FIG. 4A, so that an inner rotor 25N serves as a base rotor, that a pair of outer rotors 25U function as counter rotors, that a pair of inner stators 26N serve as base stators, and that an optional pair of outer stators 26U function as counter stators. It is appreciated, however, that each inner stator 26N defines a pair of opposite poles while abutting the adjacent pole of the inner rotor 25N by an opposite pole. Accordingly, the outer rotor 25U is abutted by another pole of the inner stator 26N which is also opposite to to the adjacent pole of the outer rotor 25U. Such an arrangement may be more effective for countering the harmful waves but may instead decrease an efficiency in generating the electromotive force. Other configurational and/or operational characteristics of the motor 24 of FIG. 4C may be similar or identical to those of the motors of FIGS. 4A and 4B.

In another example of FIG. 4D, a motor 24 includes a rotor unit (not included in this figure) and a stator unit 26, where the stator unit 26 includes two sets of stators 26N, 26U and where any of the above rotor units and other rotor units disclosed in the above co-pending Application may be used in conjunction with the stator unit 26. More specifically, a first set of the stator unit 26 includes a pair of C-shaped inner stators 26N, while a second set of the stator unit 26 includes another pair of larger C-shaped outer stators 26U. In addition, each pair (i.e., a right pair and a left pair) of the inner and outer stators 26N, 26U are arranged to physically abut each other and also magnetically abut each other by their poles of opposite polarities. Accordingly, one of such stators 26N, 26U may counter the harmful waves transmitting through the other. In this embodiment, various rotor units may be disposed inside such inner stators 26N, between the inner and outer stators 26N, 26U, outside the outer stators 26U, and the like. Accordingly, whether a specific stator serves as a basic stator or a counter stator may depend on the disposition of the basic and/or counter rotors. Other configurational and/or operational characteristics of the motor 24 of FIG. 4D may be similar or identical to those of the motors of FIGS. 4A through 4C.

In another example of FIG. 4E, another motor 24 has a rotor unit (not included in this figure) and a stator unit 26, where the stator unit 26 includes two sets of stators 26N, 26U and where any of the above rotor units and other rotor units disclosed in the above co-pending Application may be used in conjunction with the stator unit 26. More specifically, a first set of the stator unit 26 includes therein four identical inner stators 26N angularly disposed around an axis of rotation of the rotor unit, while a second set of the stator unit 26 includes a pair of larger C-shaped outer stators 26U. Similar to that of FIG. 4D, the stator unit 26 of this embodiment may include various rotor units inside such inner stators 26N, between the inner and outer stators 26N, 26U, and/or outside the outer stators 26U. Therefore, whether a specific stator serves as a basic stator or a counter stator may depend on the disposition of such basic and/or counter rotors. Further configurational and/or operational characteristics of the motor 24 of FIG. 4E are similar or identical to those of the motors of FIG. 4A to 4D.

Figure 4F:
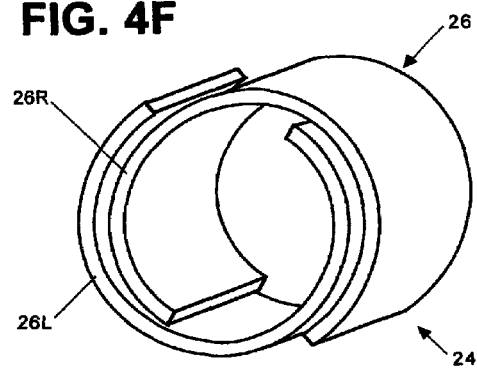

In another example of FIG. 4F, another motor 24 has a rotor unit (not included in the figure) and a stator unit 26, where the stator unit 26 includes a pair of C-shaped stators 26L, 26R of the same or similar sizes. More specifically, each of the left stator 26L and right stator 26R spans about or beyond 270°. In addition, such stators 26L, 26R are disposed in the concentric arrangement while misaligning their gaps such that the stators 26L, 26R overlap each other along most side portions of the stator unit 26. Other configurational and/or operational characteristics of the motor 24 of FIG. 4F may be similar or identical to those of the motors of FIGS. 4A to 4E.

As described hereinabove, further details of such rotor and stator units of various EMC motors and various counter units for the EMC motors have been provided in the co-pending Application which is entitled "Electromagnetically-Countered Actuator Systems and Methods" and which has the Ser. No. 60/818,627. Therefore, various prior art devices including such EMC motors can be converted into the EMC systems capable of performing their intended functions while countering such harmful waves irradiated by their motors by such counter units.

In another exemplary embodiment of this aspect of the invention, the counter units may also be incorporated into various electric generators which are inverse examples of such motors and which include various base units which are similar to those of the motors, where examples of the base units may include, but not be limited to, electromagnets, permanent magnets, any parts of the generators in which the unsteady current flows, any parts of the generators across which the unsteady voltage is applied, and the like. Therefore, any conventional devices which include the EMC generators such as AC generators, DC generators, and (automobile) alternators may be converted into the EMC systems such as EMC AC generators, EMC DC generators, EMC alternators, and so on, where various counter units of any of such configurations may be incorporated thereinto in any of such dispositions and/or arrangements, and may counter the harmful waves in any of the above mechanisms.

In another exemplary embodiment of this aspect of the invention, the counter units may also be incorporated into various heating units for countering the harmful waves irradiated by their base units, where such heating units function to convert electric energy into heat (or thermal energy) and then to transfer the heat to an user by thermal conduction, convection, and/or radiation and where examples of such heating units may include, but not be limited to, resistive wires, resistive strips, resistive coils, resistive solenoids, resistive toroids, resistive sheets, and the like. Accordingly, any prior art heating devices including such heating units such as personal heating appliances (e.g., electric mattresses, electric mats, electric blankets, electric heating pads, and the like), cooking appliances (e.g., electric grills, electric ovens, electric stoves or ranges, electric toast ovens, electric toasters, coffee makers, espresso makers, heating bottles, and the like), beauty appliances (e.g., hair dryers, hair setters, hair curlers, hair steamers, and the like), may be converted into such EMC personal heating systems, EMC cooking systems, EMC beauty systems, and the like. In general, such heating units include the above resistive parts as well as other parts for supporting or retaining the resistive parts in fixed or variable positions, for insulating other articles, and the like. Therefore, the base units of the heating units may include such resistive parts, any parts of the heating units in which the unsteady current flows, any of such parts across which the unsteady voltage applies, any of such parts capable of affecting the propagation paths of the harmful waves irradiated from other parts of the heating units, and the like. FIGS. 5A to 5H show schematic perspective views of exemplary counter units which are implemented into heating units having various base units according to the present invention, where FIGS. 5A to 5C exemplify various counter units implemented into conventional wire-, strip- or sheet-type heating units, respectively, while FIGS. 5D to 5H depict various counter units implemented into various conventional coil-type heating units. It is appreciated in these figures that various heating units only include various resistive articles and counter units therefor and that other parts of the heating units are omitted therein for simplicity of illustration. Therefore, other conductive, semiconductive, and/or insulative parts of the heating units which may emit the harmful waves are omitted in the figures and that, when necessary, such parts may be properly countered by resorting to any of such counter units as described above. It is also appreciated in FIGS. 5A to 5H that various base units and counter units of such heating units are disposed in order to form the target spaces therearound, e.g., in the front of the heating units (i.e., above the sheet), in the rear thereof (i.e., below the sheet), in the top thereof (i.e., top of the figure), and the like. It is also appreciated that details of various counter units of this embodiment have been disclosed in the co-pending application of U.S. Ser. No. 11/289,693 entitled "Electromagnetically-Shielded Heat Generating Systems and Methods."

Figure 5A:
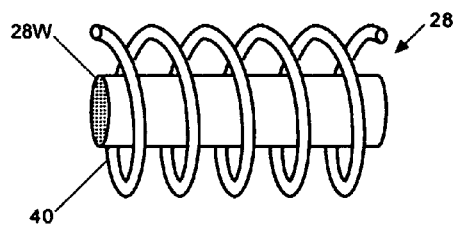
FIGS. 5A to 5H are schematic perspective views of exemplary counter units incorporated into heating units including various base units according to the present invention.

In one example of FIG. 5A, a heating unit 28 includes at least one resistive article and a counter unit 40, where the resistive article is formed as a resistive wire or resistive rod 28W which is capable of converting electric energy into heat when electric current flows therein while irradiating the harmful waves and where the resistive wire or rod 28W serves as the base unit of such a heating unit 28. In order to counter the harmful waves irradiated by the base unit 28W, the counter unit 40 is provided as a coil which is helically wound in a preset direction to the base unit 28W of the heating unit 28. In this context, the counter unit 40 is to preferentially operate on the wave matching. More specifically, such a counter unit 40 concentrically encloses the base unit 28W in its center and oriented symmetrically to the base unit 28W. In addition, the electric current is supplied to the base and counter units 28W, 40 in opposite directions. Therefore, the counter unit 40 emits such counter waves which are aligned with the harmful waves and also define the phase angles at least partially opposite to those of the harmful waves, thereby countering the harmful waves in the target space by matching the wavefronts of the harmful waves with those of the counter waves. Although seemingly similar to a conventional coaxial wire, the heating unit 28 of the example differs therefrom in a few major aspects. First of all, contrary to the coaxial wire in which multiple conductive elements are concentrically disposed, the heating unit 28 includes the resistive wire or rod 28W which defines a finite electric resistance and generates the heat when the current flows therein. Secondly, the heating unit 28 includes the counter unit 40 which encloses the base unit 28W in a sparse arrangement or, in other words, the counter unit 40 may form multiple openings or gaps therethrough, where characteristic dimensions of the openings or gaps may be tens or hundreds of times greater than a characteristic dimension of the base unit 28W. Therefore, such a counter unit 40 may be implemented at a less cost with a lesser amount of resistive material. It is appreciated in this example that such a counter unit 40 may be made of and/or include a conductive material or that the counter unit 40 itself may also be made of and/or include the resistive material and serve as another resistive article. It is also appreciated that the counter unit 40 may be wound around the base unit 28 in any direction as far as the electric current is supplied thereto in a direction opposite to that of the source current supplied to the resistive wire (or rod) 28W. It is to be understood in such an example that the heating unit 40 of this example may define the target space all around its length.

Figure 5E:
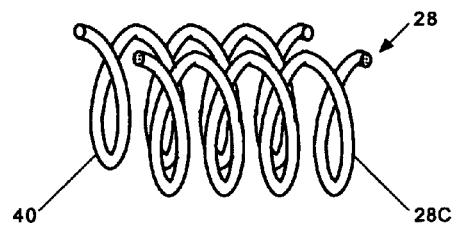
Figure 5B:
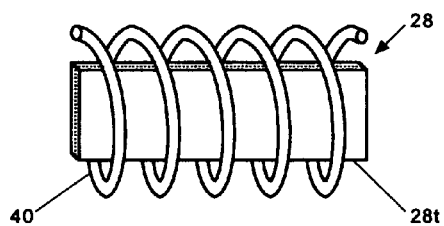

In another example of FIG. 5B, a heating unit 28 similarly includes at least one resistive article and at least one counter unit 40, where the resistive article is shaped as a resistive strip 28t which is capable of converting electric energy into heat as electric current flows therein while irradiating such harmful waves and where the counter unit 40 is provided as another coil of a conductive or resistive material. Similar to that of FIG. 5A, such a counter unit 40 may be wound along any direction and form multiple gaps or openings. When desirable, the coil 40 may also be collapsed to define an oval cross-section and oriented to receive a width or height of the resistive strip 28t along its long axis for better approximating the shape of the base unit 28t. Other configurational and/or operational characteristics of the heating unit 28 of FIG. 5B are similar or identical to those of the heating unit of FIG. 5A.

Figure 5F:
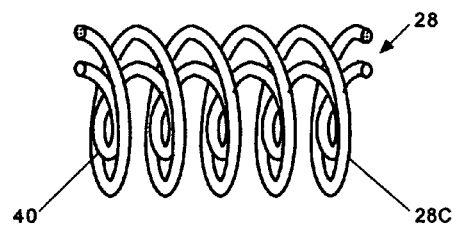
Figure 5C:
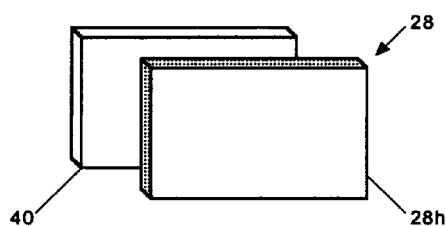

In another example of FIG. 5C, a heating unit 28 similarly includes at least one resistive article and at least one counter unit 40, where the resistive article is defined as a resistive sheet 28H which is capable of converting electric energy into heat as electric current flows therein while irradiating the harmful waves and where the counter unit 40 is formed as another sheet of a conductive or resistive material. More particularly, the counter unit 40 is oriented parallel to the base unit 28H and disposed at a preset distance therefrom such that the counter unit 40 operates on the shape matching. Therefore, the counter unit 40 emits such counter waves which is aligned with the harmful waves and define the phase angles at least partially opposite to those of the harmful waves, thereby capable of countering the harmful waves by the counter waves in the target space. It is appreciated that amplitudes of the electric current supplied to the counter unit 40 may be decided by on which side of the base unit 28H the target space is to be defined. When the target space is formed on the front of the heating unit 28 (or over the sheet), the counter unit 40 is to emit the counter waves with the amplitudes greater than those of the harmful waves, thereby countering such harmful waves at a greater distance than from the base unit 28H. When the target space is defined on the rear of the heating unit 28 (or below the sheet), the counter unit 40 is to emit the counter waves defining the amplitudes less than those of the harmful waves, thereby countering such harmful waves at a shorter distance than the base unit 28H. When the target space is defined on top of the heating unit 28, the counter unit 40 emits the counter waves with the amplitudes similar to those of the harmful waves, thereby countering such waves at a similar distance as such a base unit 28H. Other configurational and/or operational characteristics of the heating unit 28 of FIG. 5C are similar or identical to those of the heating units of FIGS. 5A and 5B.

Figure 5G:
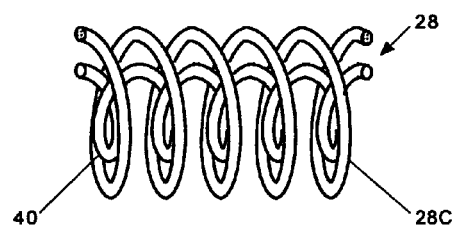
Figure 5D:
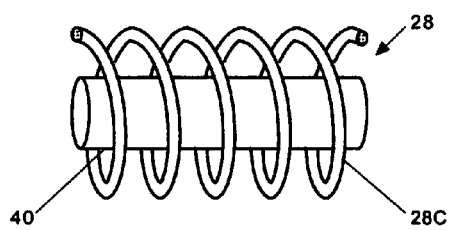

In another example of FIG. 5D, a heating unit 28 similarly includes at least one resistive article and at least one counter unit 40, where the resistive article is formed as a resistive coil 28C capable of converting electric energy into heat when electric current flows therein while irradiating the harmful waves and where the resistive coil 28C serves as the base unit of such a heating unit 28. In order to counter the harmful waves irradiated by the base unit 28C, the counter unit 40 is provided as a rod or a wire which is disposed inside the heating coil 28C and aligned with a center of the coil 28C. In this context, the counter unit 40 is to preferentially operate on the wave matching. More specifically, such a counter unit 40 is enclosed by the base unit 28W in its center and oriented symmetrically to the base unit 28W. In addition, the electric current is supplied to the base and counter units 28W, 40 in opposite directions. Therefore, the counter unit 40 emits the counter waves which are aligned with the harmful waves and define the phase angles at least partially opposite to those of the harmful waves, thereby countering the harmful waves in the target space by matching the wavefronts of such harmful waves by those of the counter waves. Although seemingly similar to a conventional coaxial wire, the heating unit 28 of the example similarly differs therefrom in a few major aspects as described in FIG. 5A. It is appreciated in this example that the counter unit 40 may also be made of and/or include a conductive material or that the counter unit 40 itself may also be made of and/or include the resistive material and serve as another resistive article. It is also appreciated that the counter unit 40 may be wound around the base unit 28 in any direction as far as the electric current is supplied thereto in a direction opposite to that of the source current supplied to the resistive coil 28C. It is appreciated in this example that the heating unit 40 of this example may define the target space all around its length. Other configurational and/or operational characteristics of the heating unit 28 of this example are similar or identical to those of the heating units of FIGS. 5A to 5C.

In another example of FIG. 5E, a heating unit 28 similarly includes at least one resistive article and at least one counter unit 40, where the resistive article is defined as a resistive coil 28C which is capable of converting electric energy into heat as electric current flows therein while irradiating such harmful waves and where the counter unit 40 is provided as another coil of a conductive or resistive material so that the counter unit 40 preferentially is to operate on the wave matching. In particular, the counter unit 40 is aligned parallel to the base unit 28C and also disposed at a preset distance from the base unit 28C. Accordingly, the counter unit 40 emits such counter waves which is aligned with the harmful waves and define the phase angles at least partially opposite to those of the harmful waves, thereby capable of countering the harmful waves in the target space. It is appreciated that amplitudes of the electric current supplied to such a counter unit 40 may depend on in which side of the base unit 28H the target space is defined. When the target space is to be formed on the front of the heating unit 28 or over the sheet, the counter unit 40 is to emit the counter waves with the amplitudes greater than those of the harmful waves, thereby countering such harmful waves at a greater distance than from the base unit 28H. When the target space is to be defined on the rear of the heating unit 28 (or below the sheet), the counter unit 40 is to emit the counter waves of the amplitudes less than those of such harmful waves, thereby countering the harmful waves at a shorter distance than from the base unit 28H. When the target space is to be formed on top of the heating unit 28, the counter unit 40 emits the counter waves of the amplitudes similar to those of the harmful waves, thereby countering the waves at a similar distance as such a base unit 28H. Other configurational and/or operational characteristics of the heating unit 28 of FIG. 5E are similar or identical to those of the heating units of FIGS. 5A to 5D.

In other examples of FIGS. 5F and 5G, each of such heating units 28 has at least one resistive article and at least one counter unit 40, where the resistive article is defined as a resistive coil 28C capable of converting electric energy into heat as electric current flows therein while irradiating such harmful waves and where the counter unit 40 is provided as another coil of a conductive or resistive material which is disposed inside the base unit 28C. Therefore, the counter unit 40 preferentially is to operate on the source matching. More particularly, the counter unit 40 is aligned parallel to a center of the base unit 28C and emit the counter waves which is aligned with the harmful waves and define the phase angles at least partially opposite to those of the harmful waves, thereby countering the harmful waves in the target space. It is appreciated that the counter units 40 may be wound in any directions, e.g., along the same direction as the heating coil 28C as in FIG. 5F or along a direction opposite to that of the heating coil 28C as in FIG. 5G. In either example, the counter unit 40 defines the target space at least substantially around the heating unit 28. Other configurational and/or operational characteristics of the heating units 28 of FIGS. 5F and 5G are similar or identical to those of the heating units of FIGS. 5A to 5E.

Figure 5H:
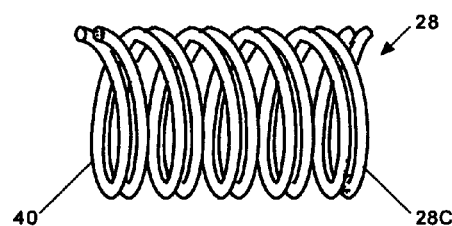

In another example of FIG. 5H, a heating unit 28 also includes at least one resistive article and at least one counter unit 40, where the resistive article is defined as a resistive coil 28C for converting electric energy into heat when electric current flows therein while irradiating such harmful waves and where the counter unit 40 is provided as another coil of a conductive or resistive material intertwined with the resistive coil 28C so that the resistive and counter coils 28C, 40 alternate each other in every pitch of the heating unit 28 In this context, the counter unit 40 operates on the source matching. More particularly, such a counter unit 40 is aligned parallel to a center line of the base unit 28C, disposed in a symmetric arrangement with respect to the resistive coil 28C, and emits the counter waves aligned with the harmful waves and having the phase angles at least partially opposite to those of the harmful waves, thereby countering such harmful waves in the target space. It is appreciated that the counter unit 40 may be wound in the same direction as the heating coil 28C while defining the target space at least substantially around the heating unit 28. Other configurational and/or operational characteristics of the heating unit 28 of FIG. 5H are similar or identical to those of the heating units of FIGS. 5A to 5G As described hereinabove, further details of such counter units of various EMC heating units have been provided in the co-pending Application which is entitled "Electromagnetically-Shielded Heat Generating Systems and Methods" and which has the U.S. Ser. No. 11/289,693. Therefore, various prior art devices with such EMC heating units can be converted into the EMC systems capable of performing their intended heating functions while countering such harmful waves irradiated by their resistive heating articles by such counter units.

In another exemplary embodiment of this aspect of the invention, the counter units may also be incorporated into various transformers which include therein at least two coils magnetically coupled to each other, where examples of the base units of such transformers may include, but not be limited to, electromagnets, inserts which may be made of and/or include the ferromagnetic, ferrimagnetic, and/or diamagnetic materials, any parts of the transformers in which the unsteady current flows, any parts of the transformers across which the unsteady voltage is applied, and the like. Accordingly, any prior art devices including such EMC transformers such as step-up transformers, step-down transformers, and AC/DC adaptors of various electric devices may be converted into the EMC transformer systems and EMC adaptor systems, where various counter units with any of the above configurations may be incorporated thereinto in any of such dispositions and/or arrangements, and may counter the harmful waves in any of the above mechanisms. It is appreciated that the EMC transformers may include one or more of such counter units disclosed in conjunction with those of FIGS. 5D to 5H, for the base units of those figures are essentially coils, with the provision that the counter units may be made of and/or include electric conductors, not resistive heaters. Similarly, various counter units disclosed in the co-pending Application entitled "Electromagnetically-Shielded Heat Generating Systems and Methods" and bearing the U.S. Ser. No. 11/289, 693 may further be incorporated to such EMC systems with the similar provision that such counter units are made of and/or include the conductive articles but not the resistive materials.

In another exemplary embodiment of this aspect of the invention, the counter units may also be incorporated into various light emitting units in order to counter the harmful waves which are irradiated by their base units, where these light emitting units function to convert electric energy into visible light rays, ultraviolet rays, and/or infrared rays and where examples of the light emitting units may include, but not be limited to, incandescent bulbs, fluorescent bulbs which include a CCFL (i.e., a cold cathode fluorescent lamp) as well as EEFL (i.e., an external electrode fluorescent lamp), CRT's (i.e., cathode ray tubes), LED's (i.e., light emitting devices), OLED's (i.e., organic light emitting devices), IOLED's and ILED's (i.e., inorganic light emitting devices), PDP's (i.e., plasma display panels), and any other devices capable of emitting such light rays. Accordingly, the base units of such light emitting units may include light emitting elements which convert the electric energy into such rays, any parts of the light emitting units through which the unsteady current flows, any parts of the light emitting units across which the unsteady voltage applies, and the like. Accordingly, any of these prior art devices may be converted into the EMC light emitting units each of which include at least one of the above light emitting units and at least one of the counter units, where various counter units of any of the above configurations may be incorporated thereinto in any of the above dispositions and/or arrangements, and may counter the harmful waves in any of the above mechanisms.

In another aspect of the present invention, any of the above EMC systems may include at least one electric shield and/or magnetic shield. In one example, the electric and/or magnetic shields (will be referred to as the "ES" and "MS" hereinafter, respectively) may be implemented into, on, over or below various portions of the EMC system. In another example, such ES and/or MS may also be implemented as above and also used in conjunction with any of the above counter units. In general, the ES may be made of and/or include at least one electrically conductive material such that the electric waves of the harmful waves may be absorbed thereinto and rerouted therealong. When desirable, the ES may also be grounded so that the absorbed and rerouted electric waves may be eliminated therefrom. The MS may be made of and/or include at least one magnetically permeable path member which may be able to absorb the magnetic waves of the harmful waves thereinto and then to reroute such magnetic waves therealong. When desirable, the MS may have a magnet member which may be magnetically coupled to the path member and terminate the absorbed and rerouted magnetic waves in at least one magnetic pole of the magnet member. The MS may include at least one optional shunt member which may also be magnetically permeable and shield its magnet member, thereby confining magnetic fields from such a magnet member closer thereto. Other details of such ES and MS have already been provided in the above co-pending Applications such as, e.g., "Shunted Magnet Systems and Methods" which bears a Ser. No. 11/213,703, "Magnet-Shunted Systems and Methods" which also bears a Ser. No. 11/213,686, and "Electromagnetic Shield Systems and Methods" which bears a U.S. Ser. No. 60/723,274. It is appreciated that the details of these co-pending Applications may be modified so that the heating elements of such co-pending Applications may be replaced by various counter units of the present invention and that the ES and/or MS may be incorporated to the counter units of this invention as such ES and/or MS have been incorporated into various heating elements of the above co-pending Applications. It is appreciated that the ES and/or MS may also be incorporated into various portions of the EMC systems of this invention as the counter units are incorporated into such portions of the EMC systems of this invention.

The ES and/or MS may be provided to define the configuration which is identical to or similar to those of various counter units of this invention. The ES and/or MS may also be disposed in, on, over, around, and/or through the base and/or counter units. The ES and/or MS may have the configuration at least partially conforming to that of such base and/or counter units or, in the alternative, may define the configuration at least partially different from those of the ES and/or MS.

The path member of the MS may define the relative magnetic permeability greater than 1,000 or 10,000, 100,000 or 1,000,000. The shunt member may be arranged to directly or indirectly contact the magnet member and to define a relative magnetic permeability greater than 1,000, 10,000, 100,000 or 1,000,000. The ES and/or MS described hereinabove or disclosed in the co-pending applications may further be incorporated into any of the prior art devices with or without any of the above counter units and define such EMC systems of this invention. The ES and/or MS may define the configuration which may be maintained to be uniform along the longitudinal or short axis of the base and/or counter units or which may vary therealong. Such configurations of the ES and/or MS may be identical to, similar to or different from those of the base and/or counters. The EMC system may include multiple ES and/or MS, where at least two of the MS and/or ES may shield against the magnetic waves and/or electric waves of the same or different frequencies in same or different extents. The ES and/or MS may be disposed over at least a portion (or entire portion) of the base and/or counter units. The EMC system may also include therein one or more of any of the above counter units as well as the ES and/or MS, where the base and/or counter units may operate on AC or DC.

As described above, the EMC systems of this invention may be provided with multiple defense mechanisms against the harmful waves which are irradiated by various base units of such a system. In one example, the counter unit may be incorporated into various portions of such an EMC system as described above. Accordingly, a single or multiple counter units may be provided in any of the above configurations and incorporated in any of the above dispositions. In another example, such ES and/or MS may be incorporated into various portions of the EMC system and shield against the electric and/or magnetic waves of such harmful waves, respectively, where dispositions of the ES and/or MS have been described in the above co-pending Applications. In another example, not only the counter units but also at least one of the ES and/or MS may be implemented into the EMC system so that the counter unit may counter at least a portion of such harmful waves and that the ES and/or MS may absorb and reroute the rest thereof. FIGS. 6A to 6H show schematic perspective views of exemplary speakers including the above counter units and MS and/or ES according to the present invention.

In the first set of examples, a coil-drive speaker 22 of FIG. 6A and a piezoelectric speaker 22 of FIG. 6B are incorporated with the counter units 40 which define the configurations similar to those of the base units of the speakers 22 according to the above source matching. The counter unit 40 of FIG. 6A is arranged greater than the base units, whereas the counter unit 40 of FIG. 6B is arranged smaller than the base units. Such counter units 40 are also disposed below the base units in the rear arrangement so that the counter units 40 generally emit the counter waves of the amplitudes greater than those of the harmful waves from the base units of the speakers 22. The MS (or ES) is provided in the shape of a planar mesh which is then disposed above the base units of the speakers 22 so that any residual harmful waves which are not properly counter by the counter units 40 may be absorbed thereinto, rerouted therealong, and terminated thereat. The MS (or ES) may also absorb, reroute, and then terminate any residual counter waves which are left over after countering the harmful waves. In another set of examples, a coil-drive speaker 22 of FIG. 6C and a piezoelectric speaker of FIG. 6D are also incorporated with the counter units 40 which are disposed along one or more wavefronts of the harmful waves according to the wave matching, where both counter units 40 are fabricated bigger or wider than the base units. Such counter units 40 are disposed above the base units of the speakers 22 in the front arrangement such that the counter units 40 generally emit the counter waves with the amplitudes less than those of the harmful waves by the base units of such speakers 22. The MS (or ES) is provided in the shape of an annular cylinder and encloses therein at least portions of the base units of the speakers 22 in order to absorb, reroute, and terminate the residual harmful waves and/or counter waves. Contrary to those of FIGS. 6A and 6B, the MS (or ES) of FIG. 6C or 6D is disposed away from the paths of propagation of audible sounds produced by the speakers 22 and, therefore, may be provided in such solid configurations. In another set of examples, a coil-drive speaker 22 of FIG. 6E and a piezoelectric speaker 22 of FIG. 6F are incorporated with the counter units 40 defining the configurations similar to those of the base units of the speakers 22 as are the cases of the source matching. The counter unit 40 of FIG. 6E is provided smaller than the base units, while the counter unit of FIG. 6F is fabricated bigger or wider than the base units. Such counter units 40 are also disposed below the base units in the rear arrangement such that the counter units 40 generally emit the counter waves of the amplitudes greater than those of the harmful waves from the base units of the speakers 22. The MS (or ES) is provided in the shape of a cylindrical mesh which is disposed around the base units of the speakers 22 such that any residual harmful or counter waves may be absorbed thereinto.

It is appreciated that any of the above counter units are provided while using the least amount of such electrically conductive, semiconductive, and/or insulative materials, while minimizing a volume, a size, and/or a mass of such counter units. Accordingly, such counter units may be fabricated with less materials at lower costs and may be easily implemented into various locations of the EMC system. It is also appreciated that any of the above counter units are provided to emit the counter waves while using the least amount of electrical energy, e.g., by drawing the least amount of the electric current or voltage. Therefore, such counter units are not only energy-efficient but also least affecting operation of other parts of the EMC systems and their intended functions. In addition, these requirements of this paragraph may minimize electric resistances of the counter units and, therefore, minimize voltage drop across the counter units.

Unless otherwise specified, various features of one embodiment of one aspect of the present invention may apply interchangeably to other embodiments of the same aspect of this invention and/or embodiments of one or more of other aspects of this invention. Therefore, any of the counter units of FIGS. 1A to 1F and FIGS. 2A to 2F may be implemented into various EMC speaker systems of FIGS. 3A to 3I, into various EMC motor systems of FIGS. 4A to 4F, into various heating units of FIGS. 5A to 5H, and other EMC systems disclosed herein without any accompanying figures. In addition, such counter units for the EMC speaker systems may be incorporated into other EMC systems of this invention, the counter units for the EMC motor systems may be incorporated to other EMC systems of this invention, the counter units for the EMC heating units may be applied to other EMC systems of this invention, and the like. Moreover, any of the counter units which operate on the source matching may be converted to operate on the wave matching or vice versa, where the source-matched counter units may then be disposed along one or more wavefronts of the harmful waves from the base unit or where the wave-matched counter units may be disposed in the preset relation to the base unit or may be incorporated in the arrangement similar to that of the base unit. In addition, any of the ES and/or MS exemplified in FIGS. 6A to 6F and disclosed in the co-pending Applications may be incorporated to any counter units disclosed in FIGS. 1A to 5H.

Various EMC systems of the present invention may operate on the AC power while countering the harmful EM waves with their counter units. When desirable, such EMC systems may also operate on the DC power while similarly countering the harmful waves. It is to be understood that the systems may also use any conventional modalities capable of shielding and/or canceling such harmful waves. Accordingly, it is preferable that any extra wires, strips, plates, sheets, and other parts of such EMC systems may be braided, bundled, concentrically fabricated or otherwise treated in order to minimize irradiation of the harmful waves.

It is to be understood that, while various aspects and/or embodiments of the present invention have been described in conjunction with the detailed description thereof, the foregoing description is intended to illustrate and not to limit the scope of the invention, which is defined by the scope of the appended claims. Other embodiments, aspects, advantages, and modifications are within the scope of the following claims as well.

What is claimed is:

1. A system capable of countering harmful electromagnetic waves irradiated thereby by at least one of canceling said waves in a target space and suppressing said waves from propagating to said target space, wherein said harmful waves have frequencies less than about 1 kHz and wherein said target space is defined between said system and an user thereof, said system comprising:
   at least one wave source which is configured to include at least one base unit, wherein said base unit is configured to include only those portions of said wave source which are responsible for at least one of irradiating said harmful waves thereby and affecting propagation paths of said harmful waves therethrough, wherein said base unit is configured to irradiate said harmful waves at least one of when an electric current flows therein and when an electric voltage is applied thereacross; and
   at least one counter unit which is configured to define configuration similar to that of said base unit and to be supplied with at least one of electric current and voltage in such a manner for emitting counter electromagnetic waves which define phase angles at least partially opposite to those of said harmful waves, wherein said counter waves are further configured to match wave characteristics thereof with those of said harmful waves due to said configuration and, accordingly, to counter said harmful waves due to said wave characteristics and phase angles in said target space.

2. The system of claim 1, wherein said wave source is one of an electrostatic speaker, a cone-drive speaker, and a piezoelectric speaker, wherein said base units of said electrostatic speaker are at least one vibratable diaphragm and at least two electric grids which are to be disposed on opposite sides of said diaphragm, wherein said base units of said cone-drive speaker are at least one voice coil and at least one permanent magnet magnetically coupled to said voice coil, and wherein said base units of said piezoelectric speaker include at least one piezoelectric plate and at least two electrodes coupled to opposite sides of said piezoelectric plates.

3. The system of claim 2, wherein said system is one of a wired telephone, a wireless telephone, an earphone, a headphone, and an assembly including at least one of said speakers and at least one microphone.

4. The system of claim 1, wherein said wave source is one of a DC motor, an universal motor, an AC synchronous motor, an AC induction motor, and a linear motor, wherein each of said motors have at least one rotor and stator, wherein said base units of said DC motor include at least one permanent magnet of said stator thereof and at least one electromagnet of said rotor thereof, wherein said base units of said universal motor include at least one electromagnet for said stator thereof and at least one electromagnet for said rotor thereof, wherein said base units of said AC synchronous motor include at least one electromagnet for its stator and at least one permanent magnet for its rotor, wherein said base units of said AC induction motor include at least one electromagnet for its stator and at least one electric conductor for its rotor, and wherein said base units of said linear motor include at least one electromagnet for its stator and at least one permanent magnet for its rotor.

5. The system of claim 4, wherein said system is one of a hair dryer, an electric toothbrush, an electric razor, a dish washer, a cloth washer, a cloth dryer, a microwave oven, a vacuum cleaner, a can opener, and an electric motorized tool.

6. The system of claim 1, wherein said wave source is a heating element and wherein said base unit of said wave source is at least one of a straight resistive wire and a coiled resistive wire.

7. The system of claim 6, wherein said system is one of a hair dryer, a hair curler, a hair setter, a heat gun, an electric blanket, an electric mattress, an electric heating pad, an electric grill, an electric oven, an electric range, and an electric toaster oven.

8. The system of claim 1, wherein said configuration is configured to be at least one of a shape, a size, and an arrangement and wherein said counter unit is configured to define at least one of said shape, size, and arrangement which are respectively similar to at least one of said shape, size, and arrangement of said base unit.

9. The system of claim 1, wherein said counter unit is configured to be an analog simplifying said configuration of said base unit.

10. The system of claim 1, wherein said counter unit is configured to define an analog providing details to said configuration of said base unit.

11. The system of claim 1, wherein said system is configured to include a plurality of said counter units at least two of which are configured to be disposed in an arrangement which is defined similar to said configuration of said base unit.

12. The system of claim 1, wherein said counter unit is configured to be disposed between said base unit and target space and then to emit said counter waves defining amplitudes which are less than those of said harmful waves for at least one of canceling and suppressing.

13. The system of claim 12, wherein said harmful waves define a plurality of wavefronts around said base unit and wherein said counter unit is configured to be extended along at least one of said wavefronts along a length which is configured to be greater than a length of said base unit.

14. The system of claim 1, wherein said counter unit is configured to be disposed on an opposite side of said target space with respect to said base unit and then to emit said counter waves defining amplitudes which are greater than those of said harmful waves for at least one of said canceling and suppressing.

15. The system of claim 14, wherein said counter unit is configured to be extended along a length which is configured to be less than a length of said base unit.

16. A system capable of countering harmful electromagnetic waves irradiated thereby by at least one of canceling said waves in a target space and suppressing said waves from propagating to said target space, wherein said harmful waves have frequencies less than about 1 kHz and wherein said target space is defined between said system and an user thereof, said system comprising:

at least one wave source which is configured to include at least one base unit, wherein said base unit is configured to include only those portions of said wave source which are responsible for at least one of irradiating said harmful waves thereby and affecting propagation paths of said harmful waves therethrough, wherein said base unit is configured to irradiate said harmful waves at least one of when an electric current flows therein and when an electric voltage is applied thereacross; and at least one counter unit which is configured to define configuration different from that of said base unit, to be incorporated in a preset arrangement, and to be supplied with at least one of electric current and voltage in such a manner for emitting counter electromagnetic waves which define phase angles at least partially opposite to those of said harmful waves, wherein said counter waves are also configured to match wave characteristics thereof with those of said harmful waves due to said arrangement and, accordingly, to counter said harmful waves due to said wave characteristics and phase angles in said target space.

17. A system capable of countering harmful electromagnetic waves irradiated thereby by at least one of canceling said waves in a target space and suppressing said waves from propagating to said target space, wherein said harmful waves have frequencies less than about 1 kHz and wherein said target space is defined between said system and an user thereof, said system comprising:

at least one wave source which is configured to include at least one base unit, wherein said base unit is configured to include only those portions of said wave source which are responsible for at least one of irradiating said harmful waves thereby and affecting propagation paths of said harmful waves therethrough, wherein said base unit is configured to irradiate said harmful waves at least one of as an electric current flows therein and as an electric voltage is applied thereacross, and wherein said harmful waves are configured to propagate toward said target space while defining a plurality of wavefronts around said base unit; and at least one counter unit which is configured to be disposed in an arrangement defined along at least one of said wavefronts and to be supplied with at least one of electric current and voltage in such a manner for emitting counter electromagnetic waves which have phase angles at least partially opposite to those of said harmful waves, wherein said counter waves are configured to propagate to said target space while defining another plurality of wavefronts around said counter unit due to said arrangement and, therefore, to counter said harmful waves due to said arrangement and said phase angles in said target space.

18. The system of claim 17, wherein said counter unit is incorporated in a preset distance from at least one of said base unit and target space such that said counter unit is configured to extend along a length greater than a length of said base unit when disposed closer to said target space than said base unit and that said counter unit is configured to extend along another length which is less than a length of said base unit when disposed farther away from said target space than said base unit.

19. The system of claim 17, wherein said system is configured to have a plurality of said counter units at least two of which are configured to be disposed in said arrangement for at least one of said canceling and suppressing.

20. The system of claim 17, wherein said system is configured to have a plurality of said counter unit, wherein each of said wavefronts is configured to define a radius of curvature, and wherein at least two of said counter units are configured to manipulate said phase angles of said counter waves in such a manner that said at least two of said counter units emit counter waves with identical phase angles for increasing said radii of said curvature of said counter waves and that said at least two of said counter units emit counter waves having at least partially opposite phase angles for decreasing said radii of said curvature of said counter waves.

* * * * *